(12) United States Patent
Rebek, Jr. et al.

(10) Patent No.: US 7,579,350 B2
(45) Date of Patent: Aug. 25, 2009

(54) SCAFFOLDS FOR α-HELIX MIMICRY

(75) Inventors: Julius Rebek, Jr., La Jolla, CA (US);
Shen Gu, Collegeville, PA (US);
Shannon Biros, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 466 days.

(21) Appl. No.: 11/368,302

(22) Filed: Mar. 3, 2006

(65) Prior Publication Data

US 2006/0205728 A1   Sep. 14, 2006

Related U.S. Application Data

(60) Provisional application No. 60/660,939, filed on Mar. 11, 2005.

(51) Int. Cl.
*C07D 403/14* (2006.01)
*C07D 413/14* (2006.01)
*A61K 31/501* (2006.01)

(52) U.S. Cl. ............. 514/247; 514/252.02; 514/252.03; 514/252.01; 514/252.05; 544/224; 544/238

(58) Field of Classification Search ................. 544/224, 544/238; 514/247, 252.02, 252.03, 252.01, 514/252.05
See application file for complete search history.

(56) References Cited

FOREIGN PATENT DOCUMENTS

JP   56005480   * 10/1981

OTHER PUBLICATIONS

Wolff Manfred E. "Burger's Medicinal Chemistry, 5ed, Part 1" John Wiley & Sons, 1995, pp. 975-977.*
Banker, G.S. et al. "Modern Pharmaceutics, 3ed." Marcel Dekker, New York, 1996, pp. 451 and 596.*
Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Englsih Translation of JP56005480.*
Boger, et al., "Preparation and Diels-Alder Reaction of a Reactive, Electron-Deficient Heterocyclic Azadiene: Dimethyl 1,2,4,5-Tetrazine-3,6-Dicarboxylate. 1,2-Diazine (Dimethyl 4-Phenyl-1,2-Diazine-3,6-Dicarboxylate) and Pyrrole (Dimethyl 3-Phenylpyrrole-2,5-dicarboxylate) Introduction", *Org. Synth.* 70: 79-88 (1992).
Rubin, et al., "The cell cycle and cell death", *Curr. Biol.* 3: 391-394 (1993).
Sattler, et al., "Structure of Bcl-$x_L$-Bak Peptide Complex: Recognition Between Regulators of Apoptosis", *Science* 275: 983-986 (1997).
Chao, et al., "BCL-2 Family: Regulators of Cell Death", *Annu. Rev. Immunol.* 16: 395-419 (1998).
Branchek, et al., "Molecular Biology and Pharmacology of Galanin Receptors", *Annals N.Y. Acad. Sci.* 863: 94-107 (1998).
Chin, et al., "Design and Evolution of a Miniature Bcl-2 Binding Protein", *Angew. Chem. Int. Ed.* 40: 3806-3809 (2001).
Hamuro, et al., "Functionalized Oligoanthranilamides: Modular and Conformationally Controlled Scaffolds", *Bioorg. Med. Chem.* 9: 2355-2363 (2001).
Ernst, et al., "Design of a Protein Surface Antagonist Based on α-Helix Mimicry: Inhibition of gp41 Assembly and Viral Fusion", *Angew. Chem. Int. Ed.* 41: 278-281 (2002).
Kutzki, et al., "Development of a Potent Bcl-$x_L$ Antagonist Based on α-Helix Mimicry", *J. Am. Chem. Soc.* 124: 11838-11839 (2002).
Ernst, et al., "Design and Application of an α-Helix-Mimetic Scaffold Based on an Oligoamide-Foldamer Strategy: Antagonism of the Bak BH3/Bcl-$x_L$ Complex", *Angew. Chem. Int. Ed.* 42: 535-539 (2003).
Kim, et al., "Therapeutic Potential of Antisense Bcl-2 as a Chemosensitizer for Cancer Therapy", *Cancer* 101: 2491-2502 (2004).

* cited by examiner

*Primary Examiner*—Kahsay T Habte
(74) *Attorney, Agent, or Firm*—Townsend and Townsend and Crew, LLP

(57)   ABSTRACT

Functionalized pyridazine derivatives having a low molecular weight and pharmaceutical compositions thereof are useful as alpha-helix mimetics and for treating conditions and/or disorders mediated by alpha-helix-binding receptors and proteins.

15 Claims, 1 Drawing Sheet

SCAFFOLDS FOR α-HELIX MIMICRY

GOVERNMENT RIGHTS

The invention described herein was supported in part by grant numbers GM27932, GM 50174 and AI50900 from the National Institutes of Health. The government has certain rights to this invention.

FIELD OF THE INVENTION

The present invention relates to compounds, intermediates and methods for the preparation and uses thereof, and pharmaceutical compositions comprising the compounds. The novel compounds are useful as ligands of natural receptors, in particular as alpha-helical ligands of natural receptors, such as those of the peptide galanin or the protein Bcl. Methods for treating diseases or conditions which are modulated through interactions between alpha helical proteins and their binding sites are other aspects of the invention.

BACKGROUND OF THE INVENTION

The alpha-helix constitutes one of the principal architectural features of peptides and proteins. It is a rod-like structure wherein the polypeptide chain coils around like a corkscrew to form the inner part of the rod and the side chains extend outward in a helical array. Approximately 3.6 amino acid residues make up a single turn of an alpha-helix; thus the side chains that are adjacent in space and make up a "side" of an alpha-helix occur every three to four residues along the linear amino acid sequence. The alpha-helix conformation is stabilized by steric interactions along the backbone as well as hydrogen bonding interactions between the backbone amide carbonyls and NH groups of each amino acid. Nearly a third of the residues in known proteins form alpha-helices and such helices are important structural elements in various biological recognition events, including ligand-receptor interactions, protein-DNA interactions, protein-RNA interactions, and protein-membrane interactions. Given the importance of alpha-helices in biological systems, it would be desirable to have available small organic molecules that act as mimics of alpha-helices. Such compounds would be useful not only as research tools, but as therapeutics to treat conditions mediated by alpha-helix binding enzymes and receptors. Yet, despite the wealth of research on other aspects of alpha-helices, relatively little research has been devoted to identifying small molecule alpha-helix mimetics and there remains a need in the art for such compounds.

Galanin is a peptide hormone of diverse biological effect found through out the nervous and endocrine systems of a number of species. It binds to at least three different G-protein coupled receptors (GalR1-3) and influences such processes as insulin secretion, gut secretion/motility, memory, sexual behavior, and pain regulation among others. Site-directed mutagenesis studies on a sixteen-amino acid fragment have shown that this peptide binds to galanin receptor type 1 (GalR1) through three amino acid residues (Trp$^2$, Asn$^5$, Tyr$^9$), thought to be in an alpha-helical conformation, as well as through the N-terminal residue. It is desirable to find low molecular weight molecules that function as potent agonists of GalR1 and possess extended in vivo stability; such compounds would be potential new analgesics. Similarly, agonists of GalR2 receptors may find also use in treating pain or dementia in Alzheimer's patients. See Branchek, T.; et al., *Ann. NY Acad. Sci.* 1998, 863, 94.

Bak and Bcl-$x_L$ belong to the Bcl-2 family of proteins, which regulate cell death through an intricate balance of homodimer and heterodimer complexes formed within this class of proteins. [M. C. Raff, *Science* 1994, 264, 668-669; D. T. Chao, S. J. Korsmeyer, *Annu. Rev. Immunol.* 1998, 16, 395-419; C. B. Thompson, *Science* 1995, 267, 1456-1462; L. L. Rubin, K. L. Philpott, S. F. Brooks, *Curr. Biol.* 1993, 3, 391-394]. Overexpression of anti-apoptotic proteins such as Bcl-$x_L$ and Bcl-2 prevent cells from triggering programmed death pathways and has been linked to a variety of cancers. Bcl-2 protein plays a critical role in inhibiting anticancer drug-induced apoptosis, which is mediated by a mitochondria-dependent pathway that controls the release of cytochrome c from mitochondria through anion channels. Constitutive overexpression of Bcl-2 or unchanged expression after treatment with anticancer drugs confers drug resistance not only to hematologic malignancies but also to solid tumors [R. Kim et al. *Cancer* 2004, 101, 2491-2502]. A current strategy for developing new anticancer agents is to identify molecules that bind to the Bak-recognition site on Bcl-$x_L$, disrupting the complexation of the two proteins and therefore antagonizing Bcl-$x_L$ function [O. Kutzki et al. *J. Am. Chem. Soc.* 2002, 124, 11,832-11,839]. The structure determined by NMR spectroscopy [M. Sattler et al. *Science* 1997, 275, 983-986] shows the 16 residue BH3 domain peptide from Bak (aa 72 to 87, $K_d \approx 300$ nM) bound in a helical conformation to a hydrophobic cleft on the surface of Bcl-$x_L$, formed by the BH1, BH2, and BH3 domains of the protein. The crucial residues for binding were shown by alanine scanning to be V74, L78, I81, and I85, which project in an i, i+4, i+7, i+11 arrangement from one face of the α-helix. The Bak peptide is a random coil in solution but adopts an α-helical conformation when complexed to Bcl-$x_L$. Studies utilizing stabilized helices of the Bak BH3 domain have shown the importance of this conformation for tight binding. [J. W. Chin, A. Schepartz, *Angew. Chem.* 2001, 113, 3922-3925; *Angew. Chem. Int. Ed.* 2001, 40, 3806-3809.]

Small molecule mimetics of alpha-helices are of immense pharmaceutical interest and would circumvent the problems associated with the use of peptidic agents. Accordingly, there is a need in the art for small molecule compounds that can modulate the activity of alpha-helix mediated interactions and therefore would be useful in the treatment of a variety of diseases mediated by these proteins.

SUMMARY OF THE INVENTION

The present invention provides low molecular weight compounds useful as alpha-helix mimetics, and compositions thereof. In one aspect, the present invention relates in part to compounds having Formula I; to processes for preparing compounds of Formula I; to pharmaceutical compositions including such compounds; and to methods for their use in treating conditions mediated by alpha-helix-binding receptors and proteins. More specifically, functionalized pyridazine derivatives are provided for use in the treatment of disorders mediated by alpha-helix interactions.

One aspect of the invention is directed to a compound having Formula I:

(Formula 1)

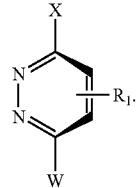

The pyridazine heterocycle of Formula I is optionally atropisomeric with respect to X and/or W. X is a radical selected from the group represented by the following structures:

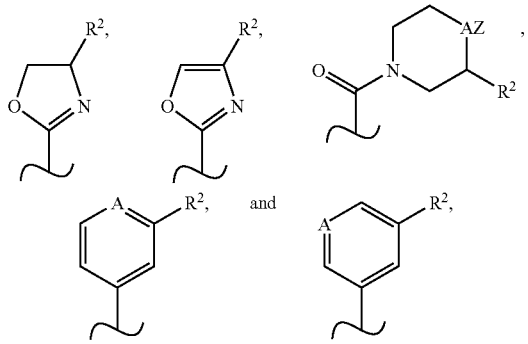

wherein A is either carbon or nitrogen, and Z is either hydrogen or (C1-C6) alkyl. W is a radical selected from the group represented by the following structures:

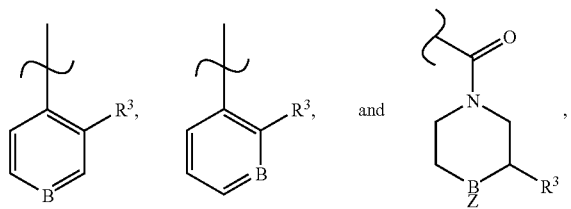

wherein B is either carbon or nitrogen. In the above structure, $R^1$ is selected from the group consisting of side chains of amino acids other than glycine; or a substituted or unsubstituted aralkyl or heterocyclylalkyl group; or a $C_{1-10}$ alkyl group, optionally comprising one or more unsaturated bonds within the alkyl chain, and optionally substituted with —$OR^4$, —$C(O)R^4$, —$COOR^4$, —$S(O)_qR^4$, —$NR^4R^5$, —$C(Y)NR^4R^5$, —$N(R^4)C(Y)OR^5$, —$NR^6C(Y)NR^4R^5$, —$NR^6C(NR^7)NR^4R^5$, —$C(NR^6)NR^4R^5$, —$C(Y)NR^4OR^5$, —$S(O)_2NR^4R^5$, or —$NR^4$—$SO_2$—$R^5$, wherein Y is O or S; $R^2$ and $R^3$ are independently selected from the group consisting of side chains of amino acids other than glycine; a substituted or unsubstituted aralkyl or heterocyclylalkyl group; a $C_{1-10}$ alkyl group, optionally comprising one or more unsaturated bonds within the alkyl chain, and optionally substituted with —$OR^4$, —$C(O)R^4$, —$COOR^4$, —$S(O)_qR^4$, —$NR^4R^5$, —$C(Y)NR^4R^5$, —$N(R^4)C(Y)OR^5$, —$NR^6C(Y)NR^4R^5$, —$NR^6C(NR^7)NR^4R^5$, —$C(NR^6)NR^4R^5$, —$C(Y)NR^4OR^5$, —$S(O)_2NR^4R^5$, or —$NR^4$—$SO_2$—$R^5$, wherein Y is O or S; —$C(O)$—$NH$—$R^8$; and —$NH$—$C(O)$—$R^9$; $R^4$, $R^5$, $R^6$, and $R^7$, at each occurrence, are independently hydrogen or a substituted or unsubstituted $C_{1-8}$ alkyl, $C_{2-6}$ alkenyl, $(C_{0-6}$ alkylene)$(C_{6-10}$ aryl), or $(C_{0-6}$ alkylene)$(C_{1-9}$ heterocyclyl) group; or $R^6$ and $R^7$, together with the N to which they are attached, form a substituted or unsubstituted heterocyclyl group; $R^8$ and $R^9$, at each occurrence, are independently a side chain of an amino acid other than glycine; a substituted or unsubstituted aralkyl or heterocyclylalkyl group; a $C_{1-10}$ alkyl group, optionally comprising one or more unsaturated bonds within the alkyl chain, and optionally substituted with —$OR^4$, —$C(O)R^4$, —$COOR^4$, —$S(O)_qR^4$, —$NR^4R^5$, —$C(Y)NR^4R^5$, —$N(R^4)C(Y)OR^5$, —$NR^6C(Y)NR^4R^5$, —$NR^6C(NR^7)NR^4R^5$, —$C(NR^6)NR^4R^5$, —$C(Y)NR^4OR^5$, —$S(O)_2NR^4R^5$, or —$NR^4$—$SO_2$—$R^5$, wherein Y is O or S; and each q is independently 0-2. The compound also comprises the stereoisomers, tautomers, solvates, prodrugs, and pharmaceutically acceptable salts of Formula I. In a preferred embodiment, $R^1$, $R^2$, and $R^3$ are independently a substituted or unsubstituted aralkyl or heterocyclylalkyl group; or a $C_{1-10}$ alkyl group, optionally substituted with —$OR^4$, —$C(O)R^4$, —$COOR^4$, —$S(O)_qR^4$, —$NR^4R^5$, —$C(Y)NR^4R^5$, —$N(R^4)C(Y)OR^5$, —$NR^6C(Y)NR^4R^5$, —$NR^6C(NR^7)NR^4R^5$, —$C(NR^6)NR^4R^5$, —$C(Y)NR^4OR^5$, —$S(O)_2NR^4R^5$, or —$NR^4$—$SO_2$—$R^5$, wherein Y is O or S. In another preferred embodiment, $R^1$, $R^2$, and $R^3$ are independently substituted or unsubstituted aralkyl or heterocyclylalkyl group; or a $C_{1-10}$ alkyl group, optionally substituted with —$OR^4$ or —$C(O)NR^4R^5$. In another preferred embodiment, $R^1$, $R^2$, and $R^3$ are independently —$CH_3$, —$CH_2CH_3$, —$(CH_2)_5C(O)OH$, —$(CH_2)_3NHC(NH)NH_2$, —$CH_2C(O)NH_2$, —$CH_2C(O)OH$, benzyl, —$(CH_2)_3NHC(O)NH_2$, —$CH_2$-cyclohexyl, —$CH_2SH$, —$(CH_2)_2C(O)OH$, —$(CH_2)_2C(O)NH_2$, —$CH_2$-imidazolyl, —$(CH_2)_2OH$, $CH(OH)CH_3$, —$CH(CH_3)CH_2CH_3$, —$CH_2CH(CH_3)CH_3$, —$(CH_2)_4NH_2$, —$(CH_2)_2SCH_3$, —$(CH_2)_3CH_3$, —$(CH_2)_2CH_3$, —$(CH_2)_3NH_2$, —$C(SH)(CH_3)CH_3$, —$CH_2OH$, —$CH_2$-thienyl, —$CH_2$-indole, —$CH_2$-phenol, or —$CH(CH_3)(CH_3)$. In another preferred embodiment, $R^1$, $R^2$, and $R^3$ are independently benzyl, methylnaphthyl, methylindolyl, or a $C_{1-10}$ alkyl group, optionally substituted with —$OH$ or —$C(O)NH_2$. In yet another preferred embodiment, $R^2$ and $R^3$ are independently —$C(O)$—$NH$—$R^8$ or —$NH$—$C(O)$—$R^9$. In some such preferred embodiments, $R^1$ is a substituted or unsubstituted aralkyl or heterocyclylalkyl group; or a $C_{1-10}$ alkyl group, optionally substituted with —$OR^4$, —$C(O)R^4$, —$COOR^4$, $S(O)_qR^4$, —$NR^4R^5$, —$C(Y)NR^4R^5$, —$N(R^4)C(Y)OR^5$, —$NR^6C(Y)NR^4R^5$, —$NR^6C(NR^7)NR^4R^5$, —$C(NR^6)NR^4R^5$, —$C(Y)NR^4OR^5$, —$S(O)_2NR^4R^5$, or —$NR^4$—$SO_2$—$R^5$, and wherein Y is O or S. In another preferred embodiment, one of $R^2$ and $R^3$ is —$C(O)$—$NH$—$R^8$, and the other of $R^2$ and $R^3$ is —$NH$—$C(O)$—$R^9$. In another preferred embodiment, $R^8$ and $R^9$ are independently —$CH_3$, —$CH_2CH_3$, —$(CH_2)_5C(O)OH$, —$(CH_2)_3NHC(NH)NH_2$, —$CH_2C(O)NH_2$, —$CH_2C(O)OH$, benzyl, —$(CH_2)_3NHC(O)NH_2$, —$CH_2$-cyclohexyl, —$CH_2SH$, —$(CH_2)_2C(O)OH$, —$(CH_2)_2C(O)NH_2$, —$CH_2$-imidazolyl, —$(CH_2)_2OH$, $CH(OH)CH_3$, —$CH(CH_3)CH_2CH_3$, —$CH_2CH(CH_3)CH_3$, —$(CH_2)_4NH_2$, —$(CH_2)_2SCH_3$, —$(CH_2)_3CH_3$, —$(CH_2)_2CH_3$, —$(CH_2)_3NH_2$, —$C(SH)(CH_3)CH_3$, —$CH_2OH$, —$CH_2$-thienyl, —$CH_2$-indolyl, —$CH_2$-phenol, or —$CH(CH_3)(CH_3)$. Preferred species are represented by the following structures:

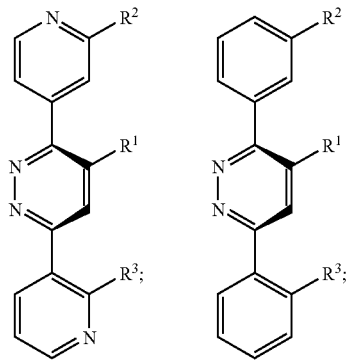

-continued

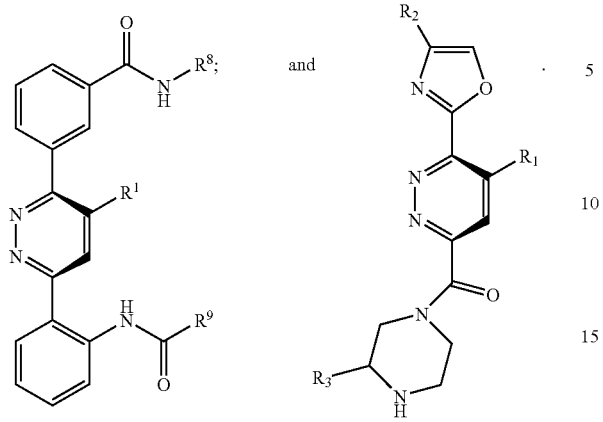

and

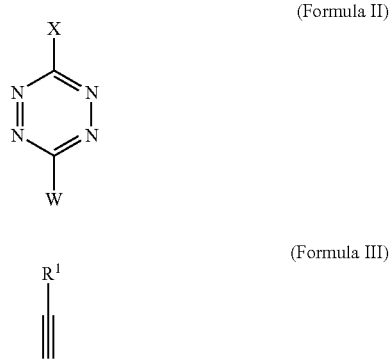

(Formula II)

Another aspect of the invention is directed to a pharmaceutical composition comprising a therapeutically effective amount of the compound of Formula I and a pharmaceutically acceptable carrier.

Another aspect of the invention is directed to a method for binding a compound to an alpha-helix-binding receptor or protein. The method comprises the step of contacting the alpha-helix-binding receptor or protein with the compound of Formula I. In a preferred mode of this aspect of the invention, the alpha-helix binding receptor is the galanin receptor. In another preferred mode, the alpha-helix binding protein is the Bcl-$x_L$ protein.

Another aspect of the invention is directed to a method for treating a biological condition mediated by an alpha-helix-binding receptor or protein. The method comprises the step of administering to a subject in need thereof an effective amount of the compound of Formula I. In a preferred mode of this aspect of the invention, the biological condition is pain or cancer. In another preferred mode, the alpha-helix-binding receptor is the galanin receptor. In another preferred mode, the alpha-helix-binding receptor is the galanin receptor 1 and the biological condition is pain. In another preferred mode, the alpha-helix-binding protein is the Bcl-$x_L$ protein and the biological condition is cancer. In another preferred mode, the cancer is pancreatic, ovarian, liver, skin, bladder, breast, prostate, colorectal and adrenal cancer, B-cell lymphoma, B-cell leukemia, chronic lymphocytic leukemia, multiple myeloma, malignant melanoma, or non-small cell lung carcinoma.

Another aspect of the invention is directed to a method of disrupting protein-protein interactions. The method comprises the step of contacting an alpha-helix-binding protein with an effective amount of the compound of Formula I for preventing or lessening the binding of the alpha-helix binding protein to an alpha-helical region of an alpha-helix containing protein. In a preferred mode of this aspect of the invention, the alpha-helix-binding protein is the galanin receptor. In another preferred mode, the alpha-helix-binding protein is the Bcl-$x_L$ protein.

Another aspect of the invention is directed to a method of preparing a compound of Formula I. The method comprises the step of reacting a compound of Formula II with a compound of Formula III, optionally in the presence of a solvent, to form a compound of Formula I. Formula II and Formula III are represented as follows:

(Formula III)

X, W, and $R^1$ are as defined in Formula I. In a preferred mode of this aspect of the invention, the solvent is diethyl ether, pentane, toluene, chloroform, dioxane, carbon tetrachloride, nitrobenzene, dichloromethane, ethyl acetate, THF, benzene, acetonitrile, dimethyl ether, 1,2-dichloroethane, xylene, acetone, chlorobenzene, DMSO, methanol, mesitylene, or mixtures thereof.

Another aspect of the invention is directed to a method for preparing a compound of Formula I. The method comprises the step of reacting a compound of Formula II with a compound of Formula IV, optionally in the presence of a solvent, to form a compound of Formula I. Formula II and Formula IV are represented as follows:

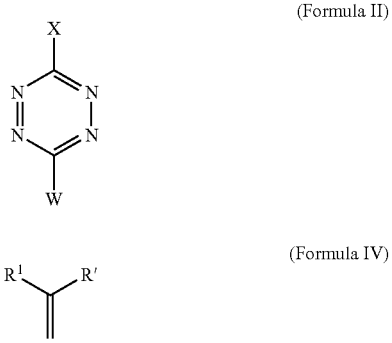

(Formula II)

(Formula IV)

X, W, and $R^1$ are as defined in Formula I; R' is a leaving group. In a preferred mode of this aspect of the invention, the leaving group is O-TMS, —SO-phenyl, morpholino, or pyrrolidino. In another preferred mode, the solvent is diethyl ether, pentane, toluene, chloroform, dioxane, carbon tetrachloride, nitrobenzene, dichloromethane, ethyl acetate, THF, benzene, acetonitrile, dimethyl ether, 1,2-dichloroethane, xylene, acetone, chlorobenzene, DMSO, methanol, mesitylene, or mixtures thereof.

Another aspect of the invention is directed to a method for preparing a compound of Formula I. The method comprises the step of reacting a compound of Formula II with a compound of Formula V, optionally in the presence of a solvent, to form a compound of Formula Ib. Formula II, Formula V, and Formula Ib are represented as follows:

(Formula II)

(Formula V)

(Formula Ib)

In the above structures, X and W are as defined in Formula I; n is 1-3. In a preferred mode of this aspect of the invention, the solvent is diethyl ether, pentane, toluene, chloroform, dioxane, carbon tetrachloride, nitrobenzene, dichloromethane, ethyl acetate, THF, benzene, acetonitrile, dimethyl ether, 1,2-dichloroethane, xylene, acetone, chlorobenzene, DMSO, methanol, mesitylene, or mixtures thereof.

Another aspect of the invention is directed to a method of preparing a compound of Formula I. The method comprises the step of reacting a compound of Formula II with a compound of Formula VI, in the presence of a base and a solvent, to form a compound of Formula I. Formula II and Formula VI are represented as follows:

(Formula II)

(Formula VI)

X, W, and $R^1$ are as defined in Formula I. In a preferred mode of this aspect of the invention, the base is KOH, NaOH, LiOH, KOtBu, NaOMe, NaOEt, or NaH. In another preferred mode, the solvent is dioxane, THF or ether.

Another aspect of the invention is directed to a method of preparing a compound of Formula I, wherein one of $R^2$ and $R^3$ is —C(O)—NH—$R^8$ and the other is —NH—C(O)—$R^9$. The method includes converting one of $R^X$ or $R^W$ of Formula VII to —NH—C(O)-$R^9$ and converting the other of $R^X$ or $R^W$ of Formula VII to —C(O)—NH—$R^8$. Formula VII has the structure:

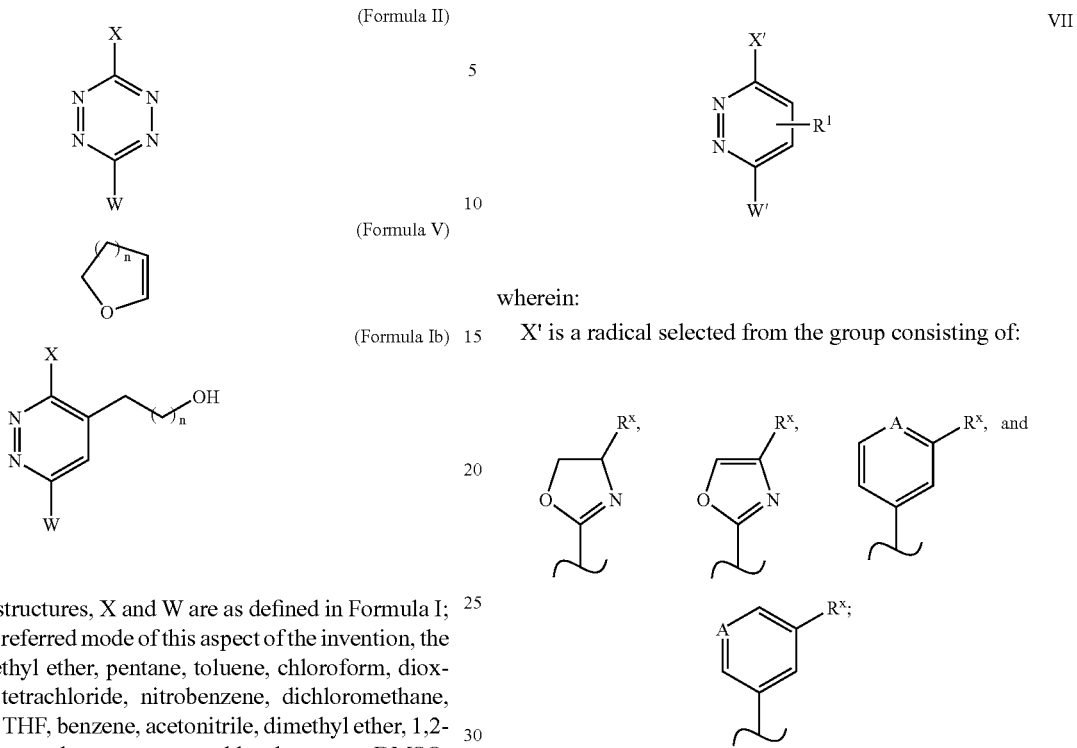

VII wherein:

X' is a radical selected from the group consisting of:

wherein A is either carbon or nitrogen, and Z is either hydrogen or ($C_{1-6}$) alkyl.

W' is a radical selected from the group consisting of:

wherein B is either carbon or nitrogen. $R^1$ is selected from the group consisting of side chains of amino acids other than glycine; a substituted or unsubstituted aralkyl or heterocyclylalkyl group; and a $C_{1-10}$ alkyl group, optionally comprising one or more unsaturated bonds within the alkyl chain, and optionally substituted with —$OR^4$, —$C(O)R^4$, —$COOR^4$, —$S(O)_qR^4$, —$NR^4R^5$, —$C(Y)NR^4R^5$, —$N(R^4)C(Y)OR^5$, —$NR^6C(Y)NR^4R^5$, —$NR^6C(NR^7)NR^4R^5$, —$C(NR^6)NR^4R^5$, —$C(Y)NR^4OR^5$, —$S(O)_2NR^4R^5$, or —$NR^4$—$SO_2$—$R^5$, wherein Y is O or S. One of $R^X$ and $R^W$ is —$NO_2$ and the other is —COOR". R" is independently hydrogen or a substituted or unsubstituted $C_{1-8}$ alkyl, $C_{2-6}$ alkenyl, or ($C_{0-6}$ alkylene)($C_{6-10}$ aryl). Formula VII includes stereoisomers thereof, tautomers thereof, solvates thereof, prodrugs thereof, and pharmaceutically acceptable salts thereof. The method is carried out such that only —$NO_2$ is converted to —NH—C(O)—$R^9$, and only —COOR" is converted to —C(O)—NH—$R^8R^X$.

In some embodiments of the method, one of $R^X$ and $R^W$ is $NO_2$ and is converted to —NH—C(O)—$R^9$ by hydrogenolysis in the presence of hydrogen and a transition metal catalyst, followed by acylation with $R^9$C(O)L wherein L is a leaving group for acylation. Suitable catalysts include palladium on carbon. Suitable leaving groups include —F, —Cl, —Br, —$N_3$, N-oxysuccinimide, 1-oxybenzotriazole, 1-oxy-7-azabenzotriazole, N-imidazolyl, or —$OCH_3$. In other embodiments, R" is hydrogen, benzyl, allyl, trimethylsilylethyl, 2,2, 2-trichloroethyl, or an unsubstituted $C_{1-6}$ alkyl group. Preferably, R" is methyl or ethyl and —COOR" is hydrolyzed to —COOH in the presence of a base, activated for amidation and reacted with $R^8NH_2$. Typical bases that may be employed include LiOH, NaOH, and KOH. In preferred embodiments, the —COOH group is activated with a coupling agent or by conversion to an acyl halide, acyl azide, or an active ester. Exemplary coupling agents include but are not limited to HATU, EDCI, and the like.

Still another aspect of the invention is directed to intermediates used in the synthesis of compounds of Formula I. Thus, the invention is directed to compounds of Formula II, Formula VIII, and Formula IX:

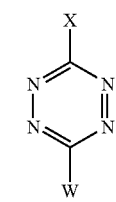

II

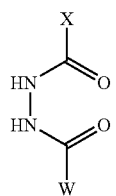

VIII

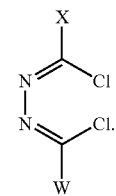

IX

In compounds of Formula II, VII, and VIII, X is a radical selected from the group consisting of:

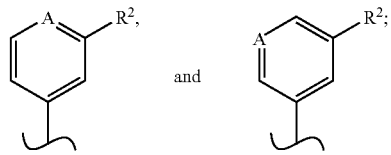

wherein A is either carbon or nitrogen, and Z is either hydrogen or ($C_{1-6}$) alkyl. W is a radical selected from the group consisting of:

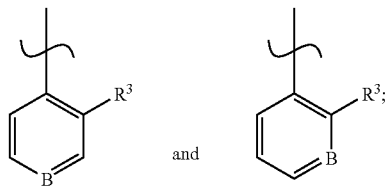

wherein B is either carbon or nitrogen. $R^2$ and $R^3$ are independently selected from the group consisting of —$COOR^4$; —$NO_2$; —$NH_2$; —$NR^4R^5$; —$N(R^4)C(Y)OR^5$; —$N(R^4)C(Y)OR^5$; side chains of amino acids other than glycine; a substituted or unsubstituted aralkyl or heterocyclylalkyl group; a $C_{1-10}$ alkyl group, optionally comprising one or more unsaturated bonds within the alkyl chain, and optionally substituted with —$OR^4$, —$C(O)R^4$, —$COOR^4$, —$S(O)_qR^4$, —$NR^4R^5$, —$C(Y)NR^4R^5$, —$N(R^4)C(Y)OR^5$, —$NR^6C(Y)NR^4R^5$, —$NR^6C(NR^7)NR^4R^5$, —$C(NR^6)NR^4R^5$, —$C(Y)NR^4OR^5$, —$S(O)_2NR^4R^5$, or —$NR^4$—$SO_2$—$R^5$, wherein Y is O or S; —C(O)—NH—$R^8$; and —NH—C(O)—$R^9$. $R^4$, $R^5$, $R^6$, and $R^7$, at each occurrence, are independently hydrogen or a substituted or unsubstituted $C_{1-8}$ alkyl, $C_{2-6}$ alkenyl, ($C_{0-6}$ alkylene)($C_{6-10}$ aryl), or ($C_{0-6}$ alkylene)($C_{1-9}$ heterocyclyl) group; or $R^6$ and $R^7$, together with the N to which they are attached, form a substituted or unsubstituted heterocyclyl group. $R^8$ and $R^9$, at each occurrence, are independently a side chain of an amino acid other than glycine; a substituted or unsubstituted aralkyl or heterocyclylalkyl group; a $C_{1-10}$ alkyl group, optionally comprising one or more unsaturated bonds within the alkyl chain, and optionally substituted with —$OR^4$, —$C(O)R^4$, —$COOR^4$, —$S(O)_qR^4$, —$NR^4R^5$, —$C(Y)NR^4R^5$, —$N(R^4)C(Y)OR^5$, —$NR^6C(Y)NR^4R^5$, —$NR^6C(NR^7)NR^4R^5$, —$C(NR^6)NR^4R^5$, —$C(Y)NR^4OR^5$, —$S(O)_2NR^4R^5$, or —$NR^4$—$SO_2$—$R^5$, wherein Y is O or S; and each q is independently 0-2. Intermediates of Formulas II, VII, and VIII include stereoisomers thereof, tautomers thereof, solvates thereof, prodrugs thereof, and pharmaceutically acceptable salts thereof.

In another aspect, the invention is directed to intermediates having the Formula XA or XB:

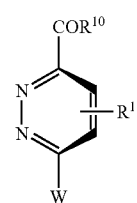

XA

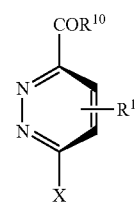

XB

In compounds of Formula XA and XB, X is a radical selected from the group consisting of:

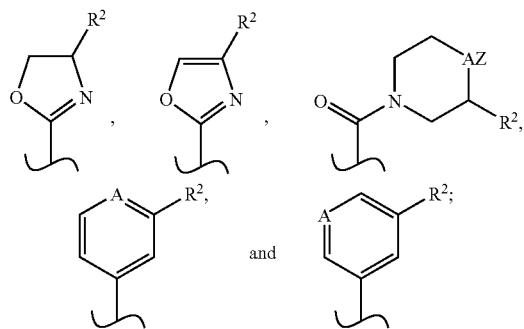

wherein A is either carbon or nitrogen, and Z is either hydrogen or (C$_{1-6}$) alkyl. W is a radical selected from the group consisting of:

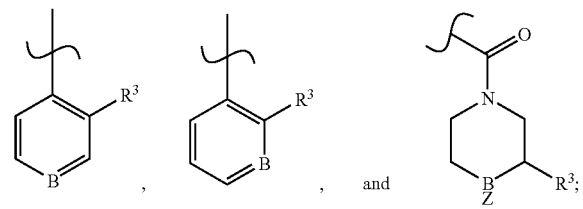

wherein B is either carbon or nitrogen. R$^1$ is selected from the group consisting of side chains of amino acids other than glycine; a substituted or unsubstituted aralkyl or heterocyclylalkyl group; and a C$_{1-10}$ alkyl group, optionally comprising one or more unsaturated bonds within the alkyl chain, and optionally substituted with —OR$^4$, —C(O)R$^4$, —COOR$^4$, —S(O)$_q$R$^4$, —NR$^4$R$^5$, —C(Y)NR$^4$R$^5$, —N(R$^4$)C(Y)OR$^5$, —NR$^6$C(Y)NR$^4$R$^5$, —NR$^6$C(NR$^7$)NR$^4$R$^5$, —C(NR$^6$)NR$^4$R$^5$, —C(Y)NR$^4$OR$^5$, —S(O)$_2$NR$^4$R$^5$, or —NR$^4$—SO$_2$—R$^5$, wherein Y is O or S. R$^2$ and R$^3$ are independently selected from the group consisting of side chains of amino acids other than glycine; a substituted or unsubstituted aralkyl or heterocyclylalkyl group; a C$_{1-10}$ alkyl group, optionally comprising one or more unsaturated bonds within the alkyl chain, and optionally substituted with —OR$^4$, —C(O)R$^4$, —COOR$^4$, —S(O)$_q$R$^4$, —NR$^4$R$^5$, —C(Y)NR$^4$R$^5$, —N(R$^4$)C(Y)OR$^5$, —NR$^6$C(Y)NR$^4$R$^5$, —NR$^6$C(NR$^7$)NR$^4$R$^5$, —C(NR$^6$)NR$^4$R$^5$, —C(Y)NR$^4$OR$^5$, —S(O)$_2$NR$^4$R$^5$, or —NR$^4$—SO$_2$—R$^5$, wherein Y is O or S; —C(O)—NH—R$^8$; and —NH—C(O)—R$^9$. R$^4$, R$^5$, R$^6$, and R$^7$, at each occurrence, are independently hydrogen or a substituted or unsubstituted C$_{1-8}$ alkyl, C$_{2-6}$ alkenyl, (C$_{0-6}$ alkylene)(C$_{6-10}$ aryl), or (C$_{0-6}$ alkylene)(C$_{1-9}$ heterocyclyl) group; or R$^6$ and R$^7$, together with the N to which they are attached, form a substituted or unsubstituted heterocyclyl group. R$^8$ and R$^9$, at each occurrence, are independently a side chain of an amino acid other than glycine; a substituted or unsubstituted aralkyl or heterocyclylalkyl group; a C$_{1-10}$ alkyl group, optionally comprising one or more unsaturated bonds within the alkyl chain, and optionally substituted with —OR$^4$, —C(O)R$^4$, —COOR$^4$, —S(O)$_q$R$^4$, —NR$^4$R$^5$, —C(Y)NR$^4$R$^5$, —N(R$^4$)C(Y)OR$^5$, —NR$^6$C(Y)NR$^4$R$^5$, —NR$^6$C(NR$^7$)NR$^4$R$^5$, —C(NR$^6$)NR$^4$R$^5$, —C(Y)NR$^4$OR$^5$, —S(O)$_2$NR$^4$R$^5$, or —NR$^4$—SO$_2$—R$^5$, wherein Y is O or S. R$^{10}$ is OH, unsubstituted C$_{1-6}$ alkoxy, benzyloxy, NHNH$_2$, or a leaving group, and each q is independently 0-2. Compounds of Formula XA and XB include stereoisomers thereof, tautomers thereof, solvates thereof, prodrugs thereof, and pharmaceutically acceptable salts thereof. Exemplary leaving groups of R$^{10}$ include —N$_3$, N-hydroxysuccinimidyl, p-nitrophenolate, pentafluorophenolate, —OC(O)OR$^{11}$, or N-oxybenzotriazole, wherein R$^{11}$ is unsubstituted C$_{1-6}$ alkyl.

DETAILED DESCRIPTION OF THE INVENTION

Figure 1:
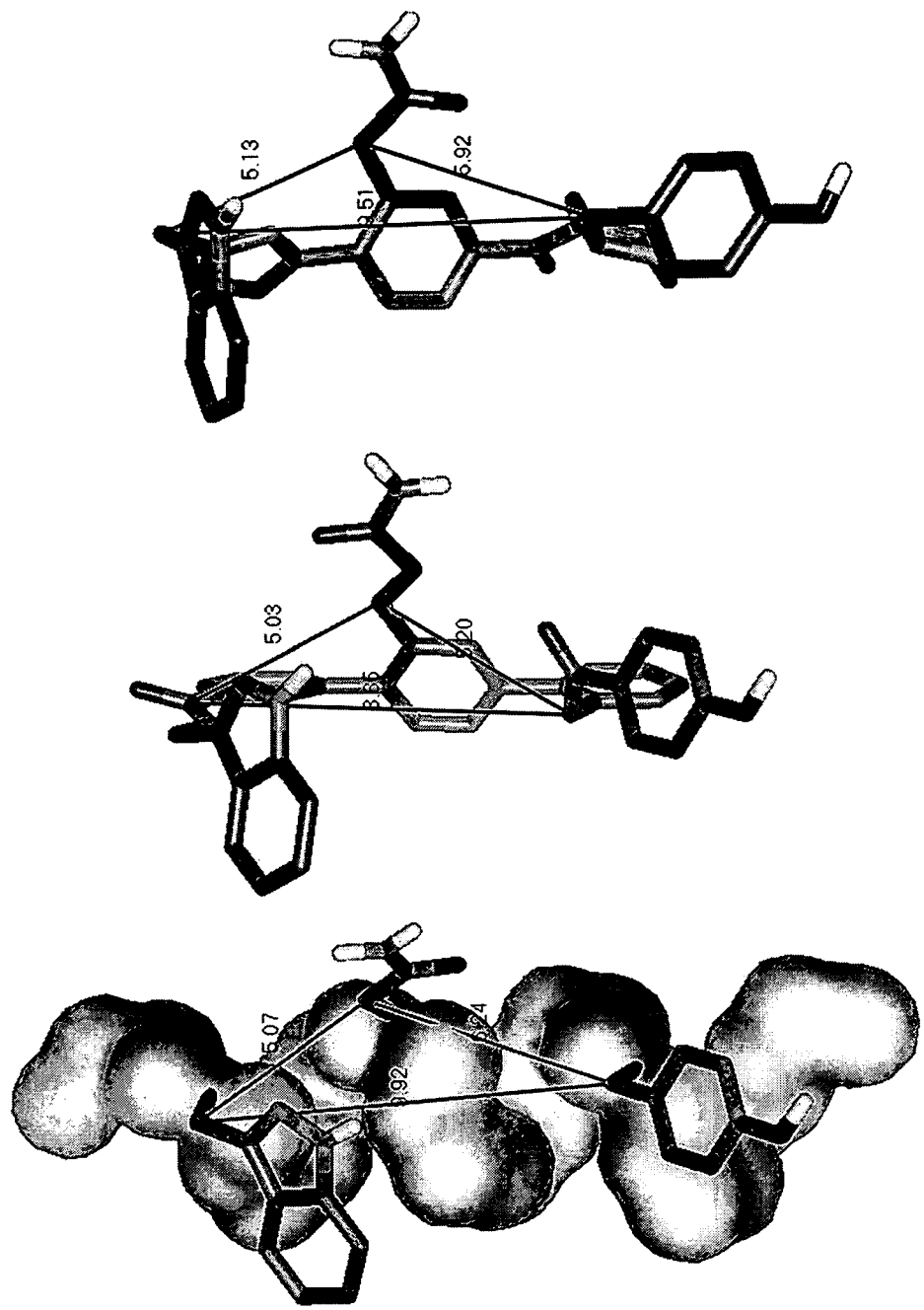
FIG. 1 illustrates a comparison of the configuration of an α-helical scaffold with an α-helical peptide.

The following definitions are used throughout this specification.

Generally, reference to a certain element such as hydrogen or H is meant to include all isotopes of that element. For example, if an R group is defined to include hydrogen or H, it also includes deuterium and tritium.

Alkyl groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, and isopentyl groups. Representative substituted alkyl groups may be substituted one or more times with, for example, amino, carboxy, carboxamido, thio, hydroxy, alkoxy, and/or halo groups such as F, Cl, Br, and I groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which may be substituted with, for example, alkyl, alkoxy, amino, thio, hydroxy, cyano, and/or halo groups.

Cycloalkyl alkyl groups are alkyl groups as defined above in which a hydrogen or carbon bond of an alkyl group is replaced with a bond to a cycloalkyl group as defined above.

Alkenyl groups are straight chain, branched or cyclic alkyl groups having 2 to about 20 carbon atoms, and further including at least one double bond. In some embodiments alkenyl groups have from 2 to 12 carbons, or, typically, from 2 to 8 carbon atoms. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others.

Alkynyl groups are straight chain or branched alkyl groups having 2 to about 20 carbon atoms, and further including at least one triple bond. In some embodiments alkynyl groups have from 2 to 12 carbons, or, typically, from 2 to 8 carbon atoms. Exemplary alkynyl groups include, but are not limited to, ethynyl, propynyl, and butynyl groups.

Aryl groups are cyclic aromatic hydrocarbons that do not contain heteroatoms. Thus, aryl groups include, but are not limited to, phenyl, azulenyl, heptalenyl, biphenylenyl, indacenyl, phenanthrenyl, triphenylenyl, pyrenyl, naphthacenyl, chrysenyl, biphenyl, anthracenyl, and naphthenyl groups. Although the phrase "aryl groups" includes groups containing fused rings, such as fused aromatic-aliphatic ring systems (e.g., indanyl, tetrahydronaphthyl, and the like) and fused aromatic-unsaturated ring systems (e.g., indenyl, fluorenyl, and the like). It does not include aryl groups that have other groups, such as alkyl or halo groups, bonded to one of the ring members. Rather, groups such as tolyl are referred to as substituted aryl groups. Representative substituted aryl groups may be mono-substituted or substituted more than once, such as, but not limited to, 2-, 3-, 4-, 5-, or 6-substituted phenyl or naphthyl groups, which may be substituted with groups including, but not limited to, amino, nitro, carboxy, carboxamido, hydroxy, thio, alkoxy, alkyl, cyano, and/or halo.

Aralkyl groups are alkyl groups as defined above in which a hydrogen or carbon bond of an alkyl group is replaced with a bond to an aryl group as defined above. Representative aralkyl groups include benzyl groups and fused (cycloalkylaryl)alkyl groups such as 4-ethyl-indanyl.

Heterocyclyl groups include aromatic and non-aromatic ring compounds containing 3 or more ring members, of which, one or more is a heteroatom such as, but not limited to, N, O, and S. In some embodiments, heterocyclyl groups include 3 to 20 ring members, whereas other such groups have 3 to 15 ring members. The phrase "heterocyclyl group" includes mono-, bi-, and polycyclic ring systems. Heterocyclyl groups thus include fused ring species including those comprising fused aromatic and non-aromatic groups. The phrase also includes bridged polycyclic ring systems containing one or more heteroatoms such as, but not limited to, quinuclidyl. However, the phrase does not include heterocyclyl groups that have other groups, such as alkyl or halo groups, bonded to one of the ring members. Rather, these are referred to as "substituted heterocyclyl groups". Heterocyclyl groups include, but are not limited to, pyrrolidinyl, piperidinyl, piperazinyl, morpholinyl, pyrrolyl, pyrazolyl, triazolyl, imidazolyl, imidazolidinyl, tetrazolyl, oxazolyl, oxazolinyl, oxazolidinyl, isoxazolyl, isoxazolinyl, isoxazolidinyl, thiazolyl, pyridinyl, pyridazinyl, pyrazinyl, pyrimidinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups may be mono-substituted or substituted more than once, such as, but not limited to, pyridazinyl, pyridinyl, oxazolidinyl, oxazolinyl, or oxazolyl groups, which are 2-, 3-, 4-, 5-, or 6-substituted, or disubstituted with groups including, but not limited to, amino, hydroxyl, thio, alkoxy, alkyl, cyano, and/or halo.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, imidazolyl, triazolyl, tetrazolyl, oxazolyl, oxazolinyl, oxazolidinyl, isoxazolyl, isoxazolinyl, isoxazolidinyl, thiazolyl, pyridinyl, pyridazinyl, pyrazinyl, pyrinidinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydroindolyl, the phrase does not include heteroaryl groups that have other groups bonded to one of the ring members, such as alkyl groups. Rather, heteroaryl groups with such substitution are referred to as "substituted heteroaryl groups". Representative substituted heteroaryl groups may be substituted one or more times with groups including, but not limited to, amino, alkoxy, alkyl, thio, hydroxy, cyano, and/or halo.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridin-3-yl methyl, tetrahydrofuran-2-yl ethyl, indol-2-yl methyl, and indol-2-yl propyl.

Heteroaralkyl groups are alkyl groups as defined above in which a hydrogen or carbon bond of an alkyl group is replaced with a bond to a heteroaryl group as defined above.

In general, "substituted" refers to a group as defined above in which one or more bonds to a hydrogen atom contained therein are replaced by a bond to non-hydrogen atoms such as, but not limited to, a halogen atom such as F, Cl, Br, and I; an oxygen atom in groups such as hydroxyl groups, alkoxy groups, aryloxy groups, aralkoxy groups, and ester groups; a sulfur atom in groups such as thiol groups, alkyl and aryl sulfide groups, sulfone groups, sulfonyl groups, sulfonamide, and sulfoxide groups; a nitrogen atom in groups such as nitro groups, amines, amides, alkylamines, dialkylamines, arylamines, alkylarylamines, diarylamines, N-oxides, imides, ureas, guanidines, amidines and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups and others also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles.

Substituted ring systems such as, but not limited to, substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with alkyl groups, alkenyl groups, or alkynyl groups as defined above.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethylchlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

Side chains of amino acids are the groups attached to the alpha carbon of alpha-amino acids. For example the side chains of glycine, alanine, and phenylalanine are hydrogen, methyl, and benzyl, respectively. The side chains may be of any naturally occurring or synthetic alpha amino acid. Naturally occurring alpha amino acids include those found in naturally occurring peptides, proteins, hormones, neurotransmitters, and other naturally occurring molecules. Synthetic alpha amino acids include any non-naturally occurring amino acid known to those of skill in the art. Representative amino acids include, but are not limited to, glycine, alanine, serine, threonine, arginine, lysine, ornithine, aspartic acid, glutamic acid, asparagine, glutamine, phenylalanine, tyrosine, tryptophan, leucine, valine, isoleucine, cysteine, methionine, histidine, 4-trifluoromethyl-phenylalanine, 3-(2-pyridyl)-alanine, 3-(2-furyl)-alanine, 2,4-diaminobutyric acid, and the like.

Pharmaceutically acceptable salts include a salt with an inorganic base, organic base, inorganic acid, organic acid, or basic or acidic amino acid. As salts of inorganic bases, the invention includes, for example, alkali metals such as sodium or potassium, alkali earth metals such as calcium and magnesium or aluminum, and ammonia. As salts of organic bases, the invention includes, for example, trimethylamine, triethylamine, pyridine, picoline, ethanolamine, diethanolamine, triethanolamine. As salts of inorganic acids, the instant invention includes, for example, hydrochloric acid, boric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, lactic acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

Certain compounds within the scope of Formula I are derivatives referred to as prodrugs. The expression "prodrug" denotes a derivative of a known direct acting drug, e.g. esters and amides, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology* 112:309-323 (1985); Bodor, N., "Novel Approaches in Prodrug Design," *Drugs of the Future* 6:165-182 (1981); and Bundgaard, H., "Design of Prodrugs: Bioreversible-Derivatives for Various Functional Groups and Chemical Entities," in *Design of Prodrugs* (H. Bundgaard, ed.), Elsevier, N.Y. (1985), Goodman and Gilmans, *The Pharmacological Basis of Therapeutics*, 8th ed., McGraw-Hill, Int. Ed. 1992. The preceding references are hereby incorporated by reference in their entirety.

Tautomers refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, ketones are typically in equilibrium with their enol forms. Thus, ketones and their enols are referred to as tautomers of each other. As readily understood by one skilled in the art, a wide variety of functional groups and other structures may exhibit tautomerism, and all tautomers of compounds having Formula I are within the scope of the present invention.

Compounds of the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

"Treating" within the context of the instant invention, means an alleviation, in whole or in part, of symptoms associated with a disorder or disease, or halt of further progression or worsening of those symptoms, or prevention or prophylaxis of the disease or disorder. Similarly, as used herein, a "therapeutically effective amount" of a compound of the invention refers to an amount of the compound that alleviates, in whole or in part, symptoms associated with a disorder or disease, or halts of further progression or worsening of those symptoms, or prevents or provides prophylaxis for the disease or disorder. Treatment may also include administering the pharmaceutical Formulations of the present invention in combination with other therapies. For example, the compounds of the invention can also be administered in conjunction with other therapeutic agents against bone disease or agents used for the treatment of metabolic disorders.

Also provided are methods for preparing compounds of the invention. In general, the invention provides methods for the preparation of compounds of Formula I, by a reverse electron demand Diels Alder reaction of a 1,2,4,5-tetrazine as the key step to forming the pyridazine structures [Boger D. L. et al. *J. Org. Chem.* 1984 49, 4405; Boger D. L. *Tetrahedron* 1983 39, 2869]. Typically, the Diels Alder reaction is performed in an organic solvent such as diethyl ether, pentane, toluene, chloroform, dioxane, carbon tetrachloride, nitrobenzene, dichloromethane, ethyl acetate, THF, benzene, acetonitrile, dimethyl ether, 1,2-dichloroethane, xylene, acetone, chlorobenzene, DMSO, methanol, mesitylene and the like, or mixtures thereof. The reaction can be performed at room temperature, or can be heated to between 80-140° C. Typically the reaction is performed at 80-100° C. Scheme 1 illustrates a typical procedure to obtain intermediates to compounds of Formula I, wherein $R^1$ is as defined herein. The starting dimethyl 1,2,4,5-tetrazine-dicarboxylate is prepared by known methods [Boger, D. L. et al. *Org. Synth.* 1992, 70, 79; Spencer et al. *J. Chem. Phys.* 1961, 35, 1939; Sauer J. et al. *Chem. Ber.* 1965, 98, 1435].

Scheme 1

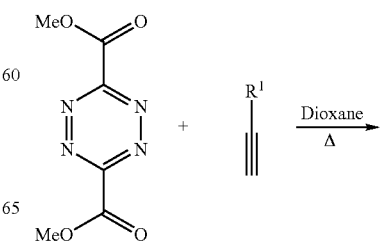

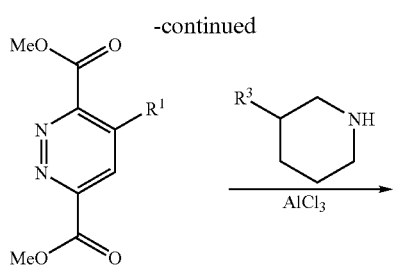

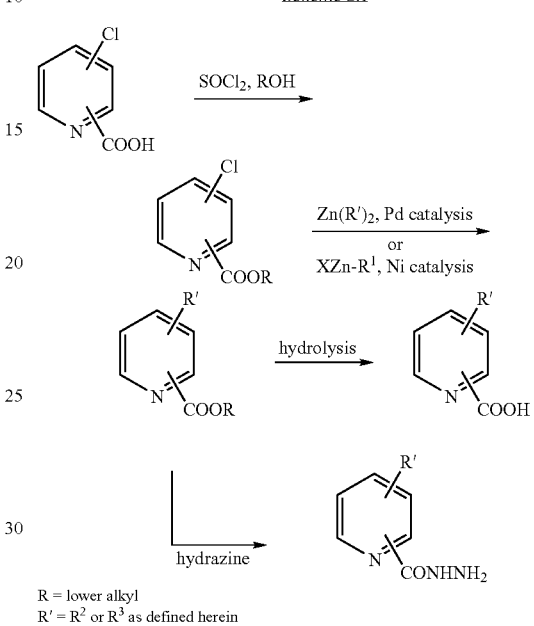

For compounds of Formula I, wherein X and W are as defined herein, the starting 1,2,4,5-tetrazine is synthesized as shown in Scheme 2A. Activation of the starting X—C(O)—OH acid can be achieved by methods known in the art, and result in the formation of activated carbonyls in which A is either —F, —Cl, —Br, —I, —N₃, N-hydroxysuccinimide, 1-hydroxybenzotriazole, pentafluorophenol, pentachlorophenol, or para-nitrophenol. Activation is followed by coupling with the hydrazide-derivative of W, which can be similarly prepared from W—C(O)—OH. Activation with PCl₅, reaction with a second hydrazine and oxidation yields the target 1,2,4,5-tetrazines.

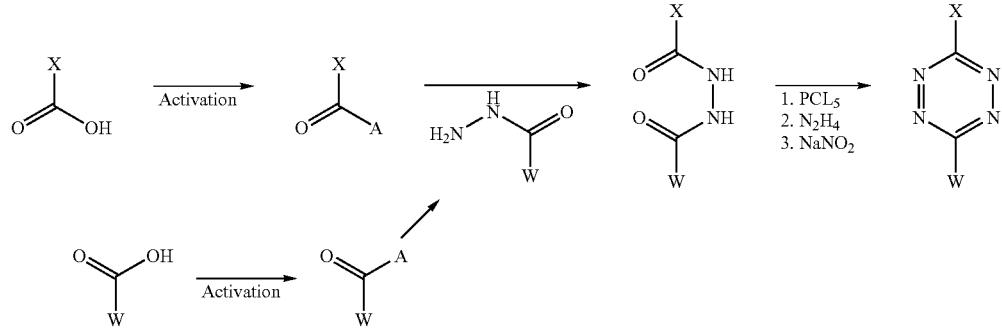

Carboxylic acid derivatives of X and W for use in Scheme 2A are readily available commercially or can be made by methods known to those of skill in the art. For example, when X and/or W are pyridine derivatives, they may be prepared as illustrated in Scheme 2B. A chloropyridine carboxylic acid is protected as an ester such as methyl or ethyl ester. Such esters may be prepared by any suitable method such as, but not limited to thionyl chloride in the chosen alcohol. The side chain may be added using various organometallic cross-coupling methods such as Negishi coupling or the nickel catalyzed reaction of the zincate under inert atmosphere. The resulting substituted pyridine carboxylic ester may be hydrolyzed with LiOH, NaOH or the like. Alternatively, in the case of methyl ester, the compound may be directly converted to the hydrazide by reaction with hydrazine. Those of skill in the art will readily understand that any regioisomer of substituted pyridine carboxylates may be prepared according to such procedures. Similarly, substituted benzoic acids for use in Scheme 2A may also be prepared by cross-coupling reactions.

The reverse electron demand Diels Alder reaction with 1,2,4,5-tetrazine to form diazines of Formula I can also be performed with alkenes substituted with a leaving group, such as O-TMS, —SO-phenyl, morpholino, or pyrrolidino and the like (see Boger D. L. *Tetrahedron* 1983 39, 2869), by essentially the same procedures as described in Scheme 1. Additionally, enolates, which can be generated in situ by reaction with aldehydes in the presence of a base (such as KOH, NaOH, LiOH, KOtBu, NaOMe, NaOEt, or NaH) can be used as reaction partners in the Diels Alder reaction. Scheme 3 shows an additional application, in which the Diels Alder reaction is performed with dihydrofuran or dihydropyran derivatives, yielding compounds of Formula I, wherein X and W are as a defined herein and n is 1, 2 or 3.

Scheme 3

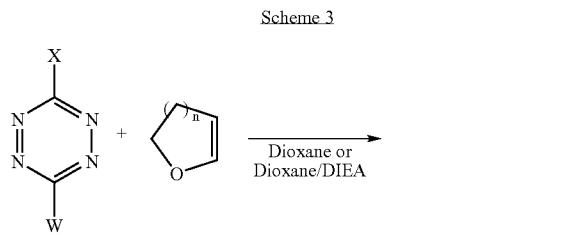

The compounds obtained from the Diels Alder reaction can be further derivatized to provide additional compounds of Formula I. In Scheme 4, the final compound obtained in Scheme 1 is further functionalized by standard methods to yield compounds of Formula I, wherein $R^1$, $R^2$ and $R^3$ are as defined previously. As exemplified, the methyl ester is transformed into the acyl hydrazide and subsequently diazotized. The azide leaving group can then be displaced by an α-amino alcohol, which can optionally be substituted. A variety of α-amino alcohols are readily available from amino acids, both natural and unnatural. Cyclization then leads to a compound of Formula I.

Scheme 4

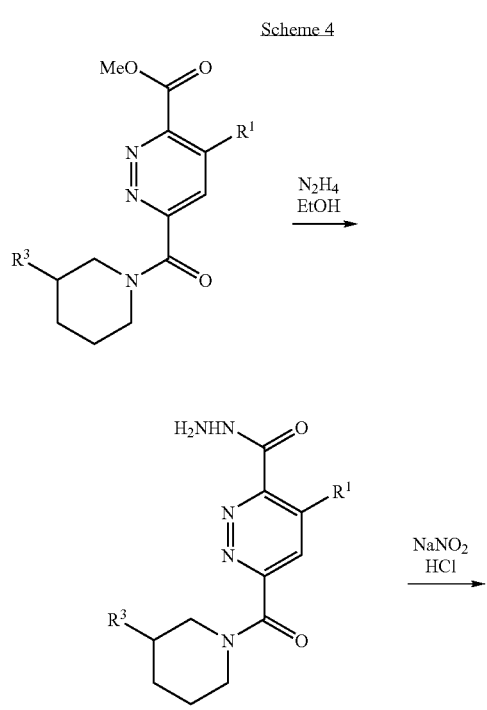

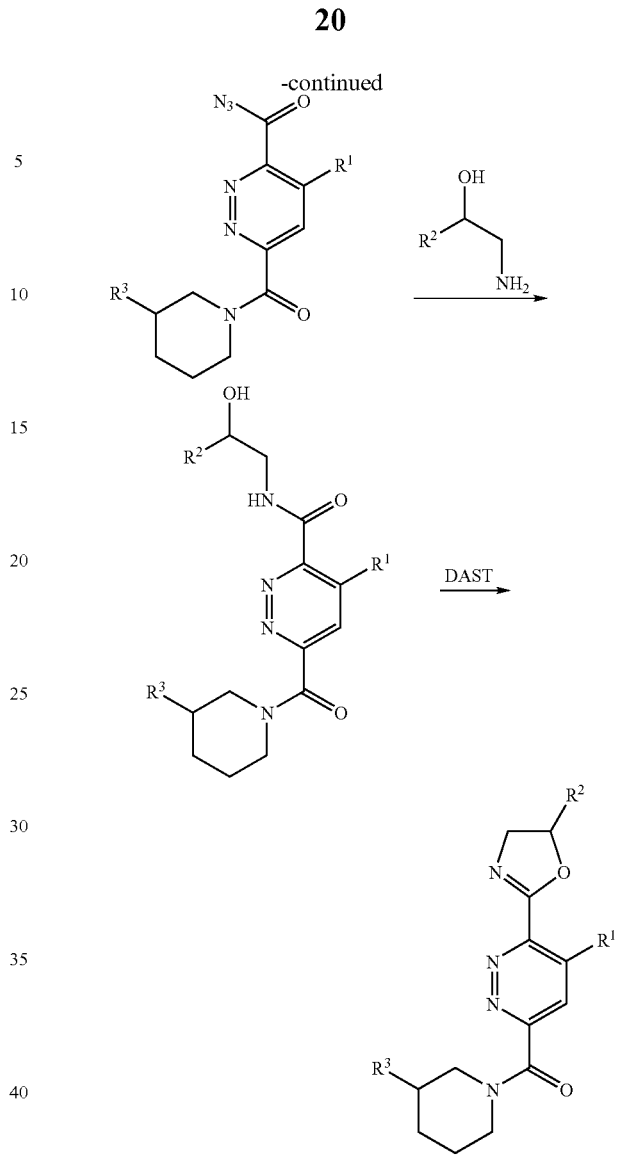

As illustrated in the schemes above, the methods allow for the synthesis of a wide variety of compounds of Formula I. The synthesis approach is highly modular and amenable to parallel synthesis techniques, allowing for incorporation of a wide array of functionality and hence the mimicking of the side-chains of many different alpha-helical proteins by compounds of Formula I. For screening purposes a "universal" library of all alpha-helix mimetics with three sites may be desirable and is accessible with the described methods. The compounds of the present invention will therefore find applicability in a wide range of alpha-helix mediated interactions and disorders.

The instant invention also provides for pharmaceutical compositions which may be prepared by mixing one or more compounds of the invention, pharmaceutically acceptable salts thereof, stereoisomers thereof, tautomers thereof, or solvates thereof, with pharmaceutically acceptable carriers, excipients, binders, diluents or the like to treat or ameliorate a variety of disorders mediated by calcitonin and/or amylin receptors. The compositions of the invention may be used to create Formulations and prevent or treat disorders mediated by calcitonin and/or amylin receptors such as bone and metabolic diseases. Such compositions can be in the form of, for example, granules, powders, tablets, capsules, syrup, suppositories, injections, emulsions, elixirs, suspensions or solutions. The instant compositions can be formulated for various routes of administration, for example, by oral administration, by nasal administration, by rectal administration, subcutaneous injection, intravenous injection, intramuscular injections, or intraperitoneal injection. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical Formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension Formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension Formulations.

For nasal administration, the pharmaceutical Formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol Formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical Formulation and/or medicament may also be a powder suitable for reconstitution with an appropriate solution as described above. Examples of these include, but are not limited to, freeze dried, rotary dried or spray dried powders, amorphous powders, granules, precipitates, or particulates. For injection, the Formulations may optionally contain stabilizers, pH modifiers, surfactants, bioavailability modifiers and combinations of these.

For rectal administration, the pharmaceutical Formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of Formulations of the soft gelatin type and suppositories. Water, saline, aqueous dextrose and related sugar solutions, and glycerols may be employed in the preparation of suspension Formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The Formulations of the invention may be designed to be short-acting, fast-releasing, long-acting, and sustained-releasing as described below. Thus, the pharmaceutical Formulations may also be Formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical Formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective amount of a compound of the present invention may vary depending upon the route of administration and dosage form. The typical compound or compounds of the instant invention is a Formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

The present invention, thus generally described, will be understood more readily by reference to the following examples, which are provided by way of illustration and are not intended to be limiting of the present invention.

EXAMPLES

The following abbreviations are used throughout the application:
AcOH: Acetic acid
BuOH: Butanol
cHex: Cyclohexane
DAST: N,N-Diethylaminosulfur trifluoride
DCM: Dichloromethane
DIEA: N,N-Diisopropylethylamine
DMF: N,N-Dimethylformamide
DMSO: Dimethylsulfoxide
EDCI: 1-ethyl-3-(3'-dimethylaminopropyl)carbodiimide hydrochloride
EtOAc: Ethyl acetate
Et$_3$N, TEA: Triethylamine
HATU: 2-(7-Aza-1H-benzotriazole-1-yl)-1,1,3,3-tetramethyluronium hexafluorophosphate
Hex: Hexanes
HOBt: 1-Hydroxybenzotriazole
MeOH: Methanol
m.p.: Melting point
NMR: Nuclear magnetic resonance
r.t.: Room temperature
TFA: Trifluoroacetic acid
THF: Tetrahydrofuran
TMS: Trimethylsilyl

Example 1

4-Isobutyl-6-(piperidine-1-carbonyl)-pyridazine-3-carboxylic acid methyl ester (5)

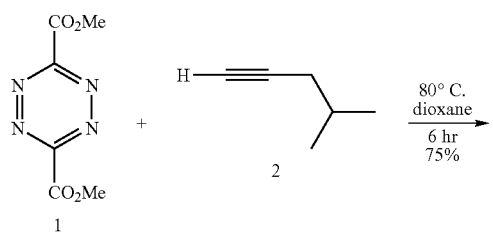

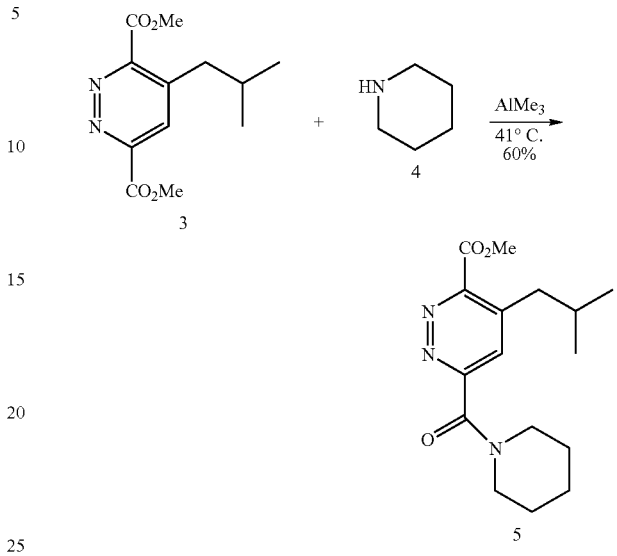

4-Isobutyl-pyridazine-3,6-dicarboxylic acid dimethyl ester (3). Tetrazine 1 (obtained as described in Boger, D. L. et al. Org. Synth. 1992, 70, 79; Spencer et al. J. Chem. Phys. 1961, 35, 1939; Sauer J. et al. Chem. Ber. 1965, 98, 1435) (500 mg, 2.52 mmol) was dissolved in 12.5 mL anhydrous 1,4-dioxane. To this bright red solution was added 355 µL 4-methyl pentyne (234 mg, 2.85 mmol), the reaction vessel was then sealed and heated to 80° C. for 6 hours. The volatiles were removed under reduced pressure, and the crude product was purified via silica gel chromatography (9.5:0.5 CH$_2$Cl$_2$-EtOAc) to give 423 mg (67% yield) of a yellow solid. R$_f$: (9.5-0.5 CH$_2$Cl$_2$-EtOAc) 0.33; $^1$H NMR: (600 MHz, CDCl$_3$) δ 8.07 (s, 1H), 4.10 (s, 3H), 4.07 (s, 3H), 2.83 (d, J=7.3 Hz, 2H), 1.97 (m, 1H), 0.95 (d, J=6.6 Hz, 6H); $^{13}$C NMR: (150 MHz, CDCl$_3$) δ 165.4, 164.5, 154.8, 151.6, 142.6, 129.9, 53.7, 53.5, 40.8, 29.7, 22.5; MS: (MALDI-FTMS) MH$^+$ expected: 253.1183, found 253.1187.

4-Isobutyl-6-(piperidine-1-carbonyl)-pyridazine-3-carboxylic acid methyl ester (5). An oven dried, nitrogen cooled two-necked 25 mL round bottom flask was charged with a solution of 78 µL piperidine (0.793 mmol, 68 mg) in 4.0 mL anhydrous DCM. Trimethyl aluminum was added slowly (2.0M/toluene, 436 µL, 0.872 mmol). The resulting mixture was stirred for twenty minutes at room temperature. To this solution was added 200 mg of the diester 3 (0.793 mmol) dissolved in 2.0 mL anhydrous DCM. The flask was sealed and heated to 41° C. for 15 hours. The reaction was allowed to cool to room temperature and quenched with slow addition of 1M HCl. The product was extracted three times with DCM, the organic fractions collected, washed with brine, dried over magnesium sulfate and evaporated to give a brownish/yellow oil. The crude mixture was applied to a column of silica gel and eluted with a 2:1 hexane-ethyl acetate solution (R$_f$=0.16) to give 132 mg of product (54% yield) as a yellow oil. MS: (ESI-TOF) MH$^+$ expected: 306.1812, found: 306.1807.

Example 2

4-Isobutyl-6-(piperidine-1-carbonyl)-pyridazine-3-carboxylic acid ((S)-1-hydroxymethyl-2-methyl-propyl)-amide (8)

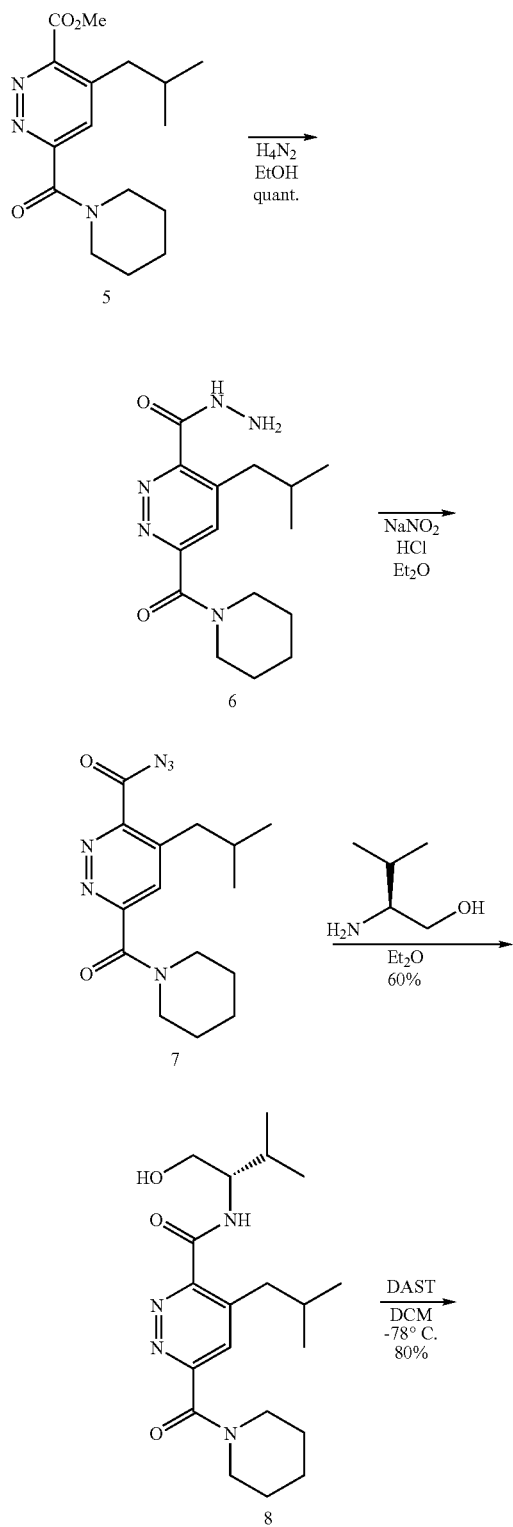

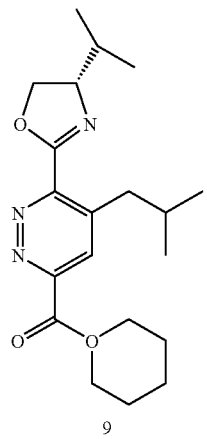

4-Isobutyl-6-(piperidine-1-carbonyl)-pyridazine-3-carboxylic acid hydrazide (6). The mono-methyl ester 5 (10 mg, 0.033 mmol) was dissolved in 3.5 mL anhydrous ethanol (dried over 4 Å molecular sieves). Hydrazine hydrate was added (55 μL, 1.65 mmol, 53 mg), and the reaction was stirred for 5.5 hours at room temperature under an atmosphere of nitrogen. The volatiles were evaporated under reduced pressure, and the product oil was triturated three times with ca. 3 mL diethyl ether. The bright yellow oil was dried under high vacuum to produce a 10 mg (quant.) of a pale yellow solid. MS: (ESI-TOF) MH$^+$ expected: 306.1924, found: 306.1923.

4-Isobutyl-6-(piperidine-1-carbonyl)-pyridazine-3-carboxylic acid ((S)-1-hydroxymethyl-2-methyl-propyl)-amide (8). Sodium nitrite (12 mg, 0.164 mmol) was dissolved in 7.5 mL H$_2$O. The solution was cooled to 0° C., and 150 μL 1.2M HCl (0.180 mmol) was added slowly. The mixture was allowed to stir for 10 minutes, at which time a solution of 50 mg hydrazide 6 (0.164 mmol) in 9 mL ethyl ether was added dropwise. The mixture was stirred vigorously for another 10 minutes at 0° C. (the more non-polar acyl-azide can be visualized by TLC, 2:2:0.4 Hex-EtOAc-MeOH). The aqueous layer was removed, and a pre-cooled solution of L-valinol (18.5 mg, 0.180 mmol) in 2 mL ethyl ether was added slowly. The reaction was allowed to warm to room temperature. The reaction mixture was diluted with ethyl ether, and the organic solution was washed with 1M HCl (3×5 mL), saturated NaHCO$_3$ (3×5 mL), brine (1×5 mL), dried over MgSO$_4$ and evaporated under reduced pressure to give a yellow oil. The crude product was purified using silica gel chromatography (4:4:0.4 Hex-EtOAc-MeOH, R$_f$: 0.21) to give 20 mg (32%) of a colorless oil. MS: (ESI-TOF) MH$^+$ expected: 377.2547, found: 377.2539.

5-Isobutyl-6-((S)-4-isopropyl-4,5-dihydro-oxazol-2-yl)-pyridazin-3-yl]-piperidin-1-yl-methanone (9). β-Hydroxy amide 8 (5 mg, 0.013 mmol) was dissolved in 250 μL anhydrous DCM and cooled to −78° C. (CO$_2$/acetone). DAST (2.0 μL, 0.014 mmol, 2.3 mg) was added, and the reaction mixture was stirred at −78° C. for 1 hour. Potassium carbonate (3 mg, 0.020 mmol) was added in one portion, and the solution was allowed to warm to room temperature. A solution of saturated sodium bicarbonate was added (0.5 mL), and the product was extracted with DCM (3×1 mL). The organic fractions were collected, washed with brine (1×2 mL), dried over Na$_2$SO$_4$, and evaporated to dryness. The crude product was purified using preparatory silica gel chromatography (10 cm×20 cm ×250 µm; 2:2:0.4 EtOAc-Hex-MeOH) to give 3 mg (64% yield) of pure oxazoline. MS: (ESI-TOF) MH+ expected: 359.2441, found: 359.2444.
Example 3
((S)-3-sec-Butyl-4-methyl-piperazin-1-yl)-[5-isobutyl-6-((S)-4-isopropyl-4,5-dihydro-oxazol-2-yl)-pyridazin-3-yl]-methanone (17)
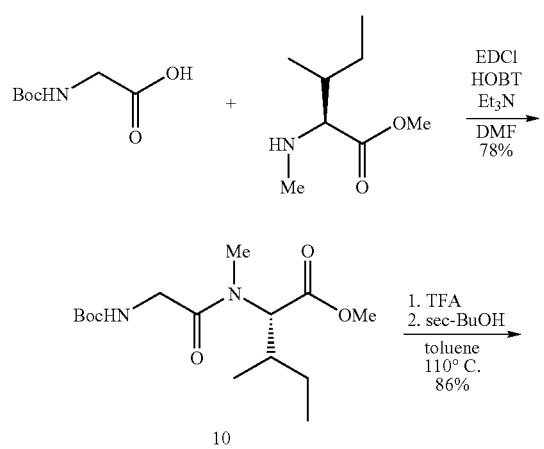
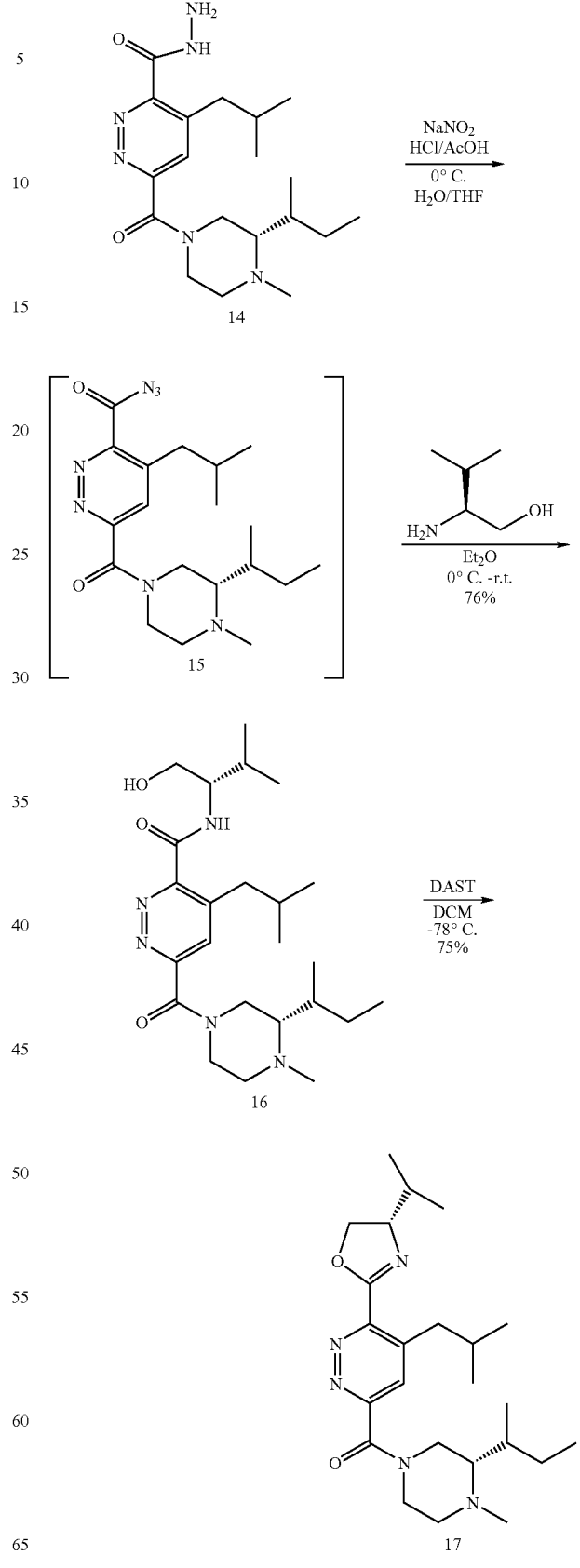

(S)-2-[(2-tert-Butoxycarbonylamino-acetyl)-methyl-amino]-3-methyl-pentanoic acid methyl ester (10). Boc-glycine (1.52 g, 8.49 mmol), N(Me)-Ile-OMe (1.10 g, 5.65 mmol), EDCl (1.6 g, 8.49 mmol) and HOBt (1.15 g, 8.49 mmol) were dissolved in 30 mL anhydrous DMF and the solution was cooled to −40° C. (acetonitrile/$CO_2$). Triethylamine (6.0 mL, 4.3 g, 42 mmol) was added slowly. The reaction mixture was allowed to warm to room temperature and stirred under nitrogen for 20 hours. The solvent was evaporated under reduced pressure, the crude oil was brought up in ethyl acetate and washed with 1M NaOH, 1M HCl, brine, dried over magnesium sulfate and evaporated to dryness. The crude product was purified using silica gel chromatography (eluent: 6:4 Hex-EtOAc) to give 1.4 g of a colorless oil (78% yield). $R_f$: (6:4 Hex-EtOAc) 0.3; MS: (MALDI-FTMS) $MNa^+$ expected: 339.1896, found: 339.1894.

(S)-6-sec-Butyl-1-methyl-piperazine-2,5-dione (11). Dipeptide 10 (1.4 g, 4.42 mmol) was dissolved in 44 mL anhydrous DCM. Trifluoroacetic acid (11 mL) was added slowly and the reaction was stirred under nitrogen for 30 minutes. The volatiles were evaporated under reduced pressure to give the TFA-dipeptide in quantitative yield. The resulting residue was then dissolved in 150 mL sec-BuOH and 100 mL toluene. The reaction was heated to 110° C. for 5 hours with ventilation. Any evaporated solvents were replaced with fresh sec-BuOH throughout the course of the reaction. The reaction was allowed to cool to room temperature and the volatiles were removed to give the crude diketopiperazine. The product was purified by silica gel chromatography (25:1 DCM-MeOH) to give 701 mg (86%) of a white solid. $R_f$: (25:1 DCM-MeOH) 0.25; MS: (MALDI-FTMS) $MH^+$ expected: 185.1284, found: 185.1284.

(S)-2-sec-Butyl-1-methyl-piperazine (12). An oven-dried, nitrogen purged flask was charged with 124 mg $LiAlH_4$ (3.26 mmol) and suspended in 2.0 mL anhydrous THF. Diketopiperazine 11 (200 mg, 1.09 mmol) was added dropwise as a solution in 7.0 mL anhydrous THF. The reaction was stirred at room temperature for 1.5 hours, followed by heating at 40° C. for 5 hours. The reaction was allowed to cool to room temperature, diluted with ca. 10 mL diethyl ether, quenched with sequential addition of 60 µL $H_2O$, 120 µL 10% NaOH, 180 µL $H_2O$, and the resulting aluminum salts filtered off. The organic solution was dried over $MgSO_4$ and evaporated to dryness under reduced pressure to yield 140 mg (82% yield) of product piperazine as a slightly brown oil which was used immediately without further purification. MS (ESI-TOF) $MH^+$ expected: 157.1699, found: 157.1703.

6-((S)-3-sec-Butyl-4-methyl-piperazine-1-carbonyl)-4-isobutyl-pyridazine-3-carboxylic acid methyl ester (13). A 25 mL oven dried schlenk flask was cooled under an atmosphere of nitrogen and charged with 70 mg piperazine 17 as a solution in 2.5 mL anhydrous DCM. $AlMe_3$ (224 µL, 2.0M solution in hexanes, 0.448 mmol) was added slowly, and the mixture was allowed to stir at room temperature for approximately ten minutes (until methane evolution had ceased). To the aluminum-amide solution was added slowly 113 mg of diazene 3 (0.448 mmol) as a solution in 2.5 mL anhydrous DCM. The schlenk flask was sealed, and the yellow solution was heated to 41° C. After 24 hours, the now orange solution was cooled to room temperature, and quenched with slow addition of 1M HCl (ca. 1 mL) with vigorous stirring. The reaction mixture was neutralized with saturated sodium bicarbonate (5 mL), the gummy precipitate filtered, and extracted with DCM (3×5 mL). The organic fractions were collected, dried over $MgSO_4$, and evaporated to dryness under reduced pressure. The crude reaction mixture was applied to a column of silica gel, and eluted with 9.6:0.4:0.1% DCM-MeOH-$Et_3N$ to give 94 mg (56%) of product (mixture of conformational isomers around the amide bond) as a yellow oil. $R_f$: (9.6:0.4:0.1% DCM-MeOH-$Et_3N$) 0.24; MS: (ESI-TOF) $MH^+$ expected: 377.2547, found: 377.2544.

6-((S)-3-sec-Butyl-4-methyl-piperazine-1-carbonyl)-4-isobutyl-pyridazine-3-carboxylic acid hydrazide (14). Diazene-methyl ester 13 (40 mg, 0.106 mmol) was dissolved in 10.5 mL ethanol, followed by the slow addition of 130 µL hydrazine hydrate (65% hydrazine, 2.65 mmol, 85 mg). The reaction mixture was stirred at room temperature under nitrogen for 20 hours, and the volatiles removed under reduced pressure. The crude product was purified using silica gel chromatography (9.5:0.5:0.1% DCM-MeOH-$Et_3N$) to give the acylhydrazide as 30 mg (75% yield) of a yellow oil. $R_f$: (9.5:0.5:0.1% DCM-MeOH-$Et_3N$) 0.28; MS: (ESI-TOF) $MH^+$ expected: 377.2659, found: 377.2654.

6-((S)-3-sec-Butyl-4-methyl-piperazine-1-carbonyl)-4-isobutyl-pyridazine-3-carboxylic acid ((S)-1-hydroxymethyl-2-methyl-propyl)-amide (16). A 7 mL glass vial was charged with 500 µL water and cooled to 0° C. Sodium nitrite (1.8 mg, 0.026 mmol, 180 µL of 10 mg/mL aqueous solution), 1M hydrochloric acid (52 µL, 0.052 mmol) and acetic acid (0.039 mmol, 2.3 mg, 230 µL of 10 mg/mL aqueous solution) were added sequentially and stirred for ca. five minutes. A solution of acyl hydrazide 14 (5 mg in 500 µL THF:200 µL $H_2O$, 0.013 mmol) was added slowly and the reaction mixture was stirred at 0° C. for 10 minutes. The acidic solution was neutralized with saturated sodium bicarbonate (2 mL) and extracted with cold diethyl ether (3×2 mL). The organic fractions were collected in a second 20 mL vial at 0° C., and 270 µL of a cold, ethereal solution of L-valinol (10 mg/mL, 0.026 mmol, 2.7 mg) was added slowly. The reaction was allowed to warm to room temperature, and stirred overnight. The solvent was evaporated, and the product was purified by silica gel chromatography (9.4:0.6:0.1% DCM:MeOH:$Et_3N$, $R_f$=0.35) to give 5 mg (86% yield) of a colorless oil. MS: (ESI-TOF) $MH^+$ expected: 448.3282, found: 448.3283.

((S)-3-sec-Butyl-4-methyl-piperazin-1-yl)-[5-isobutyl-6-((S)-4-isopropyl-4,5-dihydro-oxazol-2-yl)-pyridazin-3-yl]-methanone (17). β-Hydroxy amide 16 (8 mg, 0.018 mmol) was dissolved in 500 µL DCM and cooled to −78° C. DAST (3 µL, 0.020 mmol, 3.2 mg) was added slowly and the reaction mixture was stirred for 1 hour at −78° C. The reaction was quenched with the addition of ca. 4 mg $K_2CO_3$ (0.027 mmol) and allowed to warm to room temperature. Saturated sodium bicarbonate was added (1 mL), the product was extracted with DCM (3×1 mL), washed with brine (1×1 mL), dried over magnesium sulfate and evaporated to give a yellow oil. The product was purified by prep plate chromatography (250 µm×20 cm×20 cm; 9.8:0.2:0.1% DCM-MeOH-$Et_3N$, $R_f$=0.20) to give 5 mg (65%) of a colorless oil.

Example 4

3-Methyl-benzoic acid N'-(2-benzyl-benzoyl)-hydrazide

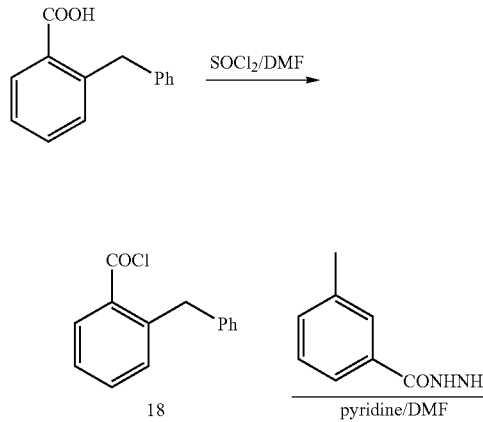

Example 6

N-[Chloro-(3-methyl-phenyl)methylene]-N'-[chloro-(2-benzyl-phenyl)methylene]hydrazine (20) and 2-(2-benzyl-phenyl)-5-m-tolyl-[1,3,4]-oxadiazole (21)

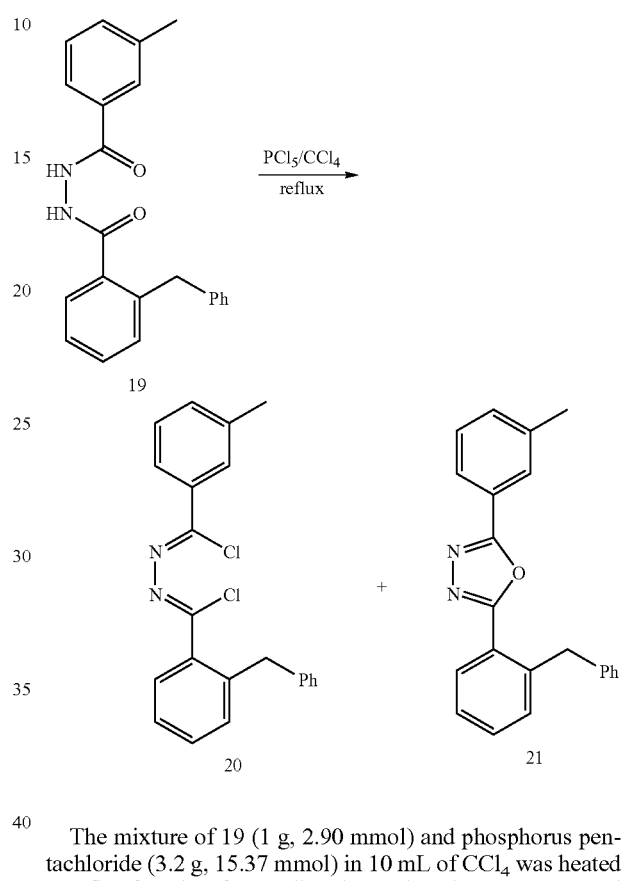

2-Benzyl-benzoyl chloride (18). To a solution of α-phenyl-o-toluic acid (4 g, 18.28 mmol) in dry $CH_2Cl_2$ (30 mL) was added thionyl chloride (5 mL, 68.50 mmol), followed by a drop of dry DMF. The reaction mixture was refluxed for 5 hr. The solvent and excess $SOCl_2$ was removed in vacuo to give 2-benzyl-benzoyl chloride 18 as a pale yellow oil which was used directly in next step.

3-Methyl-benzoic acid N'-(2-benzyl-benzoyl)-hydrazide (19). To a solution of 3-methylbenzoic hydrazine (2.7 g, 17.98 mmol) in a mixture pyridine (3 mL) and DMF (5 mL) was added 2-benzyl-benzoyl chloride 18 (prepared as above) dropwise. The reaction mixture was stirred overnight and then poured on ice water (20 mL). The precipitate was collected, and washed with water. The crude solid product was purified by flash column chromatography (2-4% MeOH in $CH_2Cl_2$) to give compound 19 (5.15 g, 83% yield) as a white solid, m.p. 149-150° C.; HRMS (MALDI-FTMS) calcd for $C_{22}H_{20}N_2O_2+H^+$: 345.1597, found 345.1601.

The mixture of 19 (1 g, 2.90 mmol) and phosphorus pentachloride (3.2 g, 15.37 mmol) in 10 mL of $CCl_4$ was heated to reflux for 8 h. After cooling down, the mixture was poured into ice water and then extracted with EtOAc. The organic phase is washed with water to neutral, dried over anhydrous magnesium sulfate and evaporated. The crude product is purified by flash column chromatography (2% EtOAc in n-hexane for 20 and 8-10% EtOAc in n-hexane for 21) to give N-[Chloro-(3-methyl-phenyl)methylene]-N'-[chloro-(2-benzyl-phenyl)methylene]hydrazine 20 (803 mg, 2.11 mmol, 73% yield) and 2-(2-benzyl-phenyl)-5-m-tolyl-[1,3,4]-oxadiazole 21 (223 mg, 0.68 mmol, 23% yield).

Compound 20: Yellow oil, $^1$H NMR (599 MHz, acetone-$d_6$, 300° K) δ 7.93 (s, 1H), 7.90 (t, J=2.6 Hz, 1H), 7.75 (d, J=7.6 Hz, 1H), 7.47 (t, J=7.7 Hz, 1H), 7.43-7.40 (m, 3H), 7.32 (d, J=7.7 Hz, 1H), 7.26 (t, J=7.6 Hz, 2H), 7.21 (d, J=7.3 Hz, 2H), 7.17 (t, J=7.5 Hz, 1H), 4.41 (s, 2H), 2.42 (s, 3H); $^{13}$C NMR (150 MHz, acetone-$d_6$, 300° K) δ 144.2, 143.2, 141.4, 140.9, 139.5, 135.2, 134.0, 133.8, 131.9, 131.8, 130.8, 129.9 (2C), 129.6, 129.5, 129.2 (2C), 127.4, 126.9, 126.5, 39.4, 21.3; HRMS (MALDI-FTMS) calcd for $C_{22}H_{18}N_2Cl_2+H^+$: 381.0920, found 381.0925.

Compound 21: Pale yellow solid, m.p. 87-88° C.; $^1$H NMR (599 MHz, acetone-$d_6$, 300° K) δ 8.08 (d, J=7.2 Hz, 1H), 7.85 (d, J=7.6 Hz, 1H), 7.84 (s, 1H), 7.52 (t, J =7.5 Hz, 1H), 7.46-7.37 (m, 4H), 7.25-7.19 (m, 4H), 7.15 (t, J=7.2 Hz, 1H), 4.58 (s, 2H), 2.40 (s, 3H); $^{13}$C NMR (150 MHz, acetone-$d_6$, 300° K) δ 165.1, 164.9, 141.5, 139.8, 133.2, 132.6, 132.2, 130.3, 129.9, 129.6 (2C), 127.9, 127.7, 126.8, 124.73, 124.67, 124.1, 40.0, 21.2.

Example 7

2-(2-Benzyl-phenyl)-5-m-tolyl-[1,3,4]-oxadiazole (21)

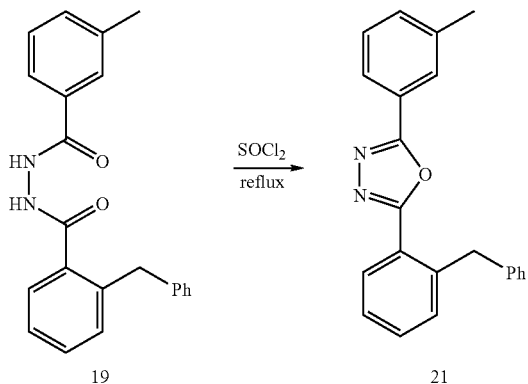

To a solution of 19 (1.1 g, 3.194 mmol) in 4 mL benzene was added SOCl₂ (2.2 mL, 30.13 mmol). The mixture was heated to reflux overnight and then solvent and excess SOCl₂ were evaporated. The yellow residue was dissolved in EtOAc. The organic layer was washed with saturated NaHCO₃ aqueous solution, H₂O and brine, dried over MgSO₄ and concentrated. The crude product was purified by flash column chromatography (8-10% EtOAc in n-hexane) to give 2-(2-benzyl-phenyl)-5-m-tolyl-[1,3,4]-oxadiazole 21 (1.0 g, 3.064 mmol, 96% yield).

Example 7

3-(2-Benzyl-phenyl)-6-m-tolyl-1,2-dihydro-[1,2,4,5] tetrazine (22)

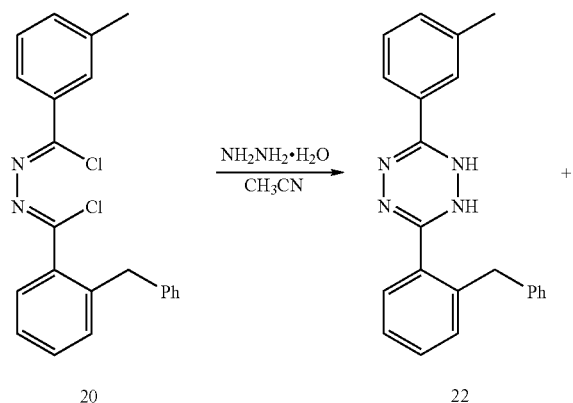

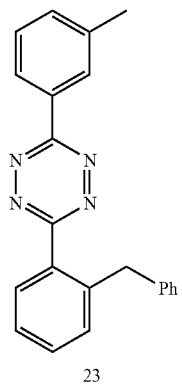

To a solution of dichloride 20 (750 mg, 1.97 mmol) in acetonitrile (10 mL) absolute hydrazine hydrate (74 μL, 2.065 mmol) was added dropwise and the mixture was stirred for 1 hr. at 40-50° C. The yellow precipitate was collected by filtration, washed with acetonitrile and degassed water to yield 3-(2-Benzyl-phenyl)-6-m-tolyl-1,2-dihydro-[1,2,4,5] tetrazine 22 (285 mg, 0.837 mmol, 43% yield) as yellow solid, m.p. 162-163° C.; ¹³C NMR (150 MHz, acetone-d₆, 300° K) δ 150.1, 148.6, 142.0, 141.5, 139.0, 132.5, 131.7, 131.6, 131.3, 130.4, 130.0 (2C), 129.9, 129.2, 129.1 (2C), 127.5, 127.1, 126.8, 124.0, 39.1, 21.3.

Example 8

3-(2-Benzyl-phenyl)-6-m-tolyl-[1,2,4,5] tetrazine (23)

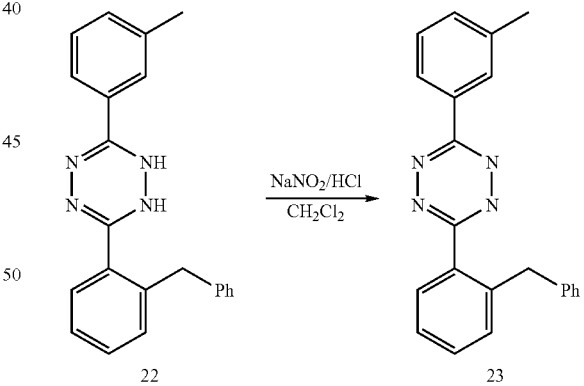

Method A: A solution of 6N NaNO₂ in water (1 mL, 5.876 mmol) was added dropwise to conc. HCl (0.7 mL, 7.05 mmol). The resulting nitrous gases were bubbled through a suspension of 22 (200 mg, 0.588 mmol) in CH₂Cl₂ cooled to 0° C. for 1 hr. The solvent was removed in vacuo. The purple residue was purified by flash column chromatography (2% EtOAc in n-hexane) to give 3-(2-Benzyl-phenyl)-6-m-tolyl-[1,2,4,5] tetrazine 23 (198 mg, 0.585 mmol, 100% yield). m.p. 90-91° C.; HRMS (MALDI-FTMS) calcd for C₂₂H₁₈N₄+H⁺: 339.1604, found 339.1597.

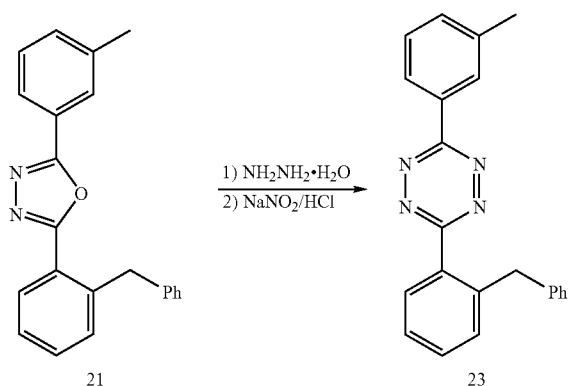

Method B: To a solution of [1,3,4]-oxadiazole 21 (200 mg, 0.613 mmol) in acetonitrile (4 mL) absolute hydrazine hydrate (44 μL, 1.226 mmol) was added dropwise and the mixture was stirred for 2 hr. at 40-50° C. Then a solution of 6N NaNO$_2$ in water (1 mL, 6.0 mmol) was added dropwise to conc. HCl (0.7 mL, 7.1 mmol). The resulting nitrous gases were bubbled through the above reaction mixture at room temperature for 1 h. The solvent was removed in vacuo. The residue was purified by flash column chromatography (2% EtOAc in n-hexane) to give 3-(2-Benzyl-phenyl)-6-m-tolyl-[1,2,4,5] tetrazine 23 (53 mg, 0.157 mmol, 39% yield) as a purple solid.

Example 9

3-[N'-(2-Nitro-benzoyl)-hydrazinocarbonyl]-benzoic acid methyl ester (26)

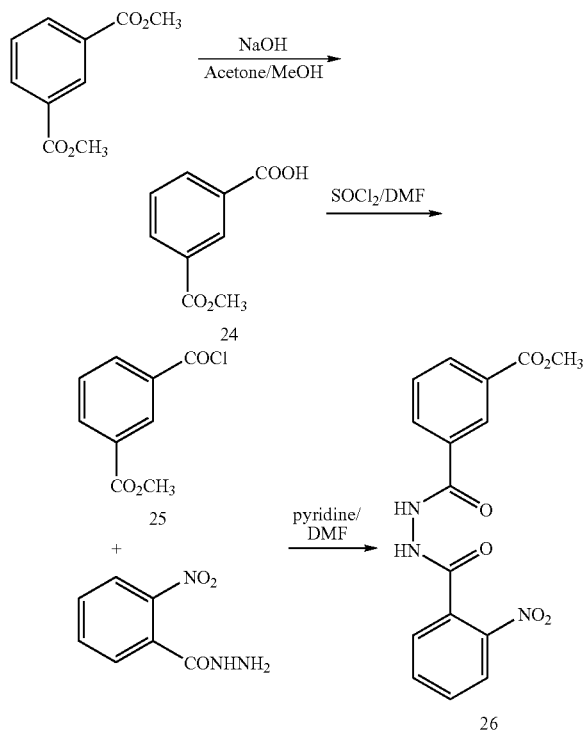

Isophthalic acid monomethyl ester (24). A solution of dimethyl isophthalate (25 g, 128.75 mmol) was dissolved in acetone (250 mL) and a solution of NaOH (5.4 g, 135 mmol) in methanol (50 mL) was added dropwise. A white precipitated was observed and the slurry was stirred for 18 h at room temperature. Then powdered NaOH (0.5 g) was added. The acetone was evaporated until dryness and the white residue was dissolved in water (250 mL), extracted with diethylether (2×100 mL). The aqueous solution was acidified with concentrated HCl to pH 4~5 and the white precipitate was filtered, dried under vacuum and the desired monoacid obtained (17 g, 94.36 mmol, 73% yield) as a white solid.

3-Chlorocarbonyl-benzoic acid methyl ester (25). SOCl$_2$ (15 mL) and dry DMF (2 drops) were added to monomethyl isophthalate (5 g, 17.7 mmol), and the reaction mixture was refluxed at 80° C. for 6 hr. The SOCl$_2$ was removed in vacuo, and a colorless oil was obtained and used directly in the next step.

3-[N'-(2-Nitro-benzoyl)-hydrazinocarbonyl]-benzoic acid methyl ester (26). The same procedure as used for 19 was applied, affording the target compound in 76% yield, as a white solid, m.p. 183-184° C.; HRMS (MALDI-FTMS) calcd for C$_{16}$H$_{13}$N$_3$O$_6$+H$^+$: 366.0697, found 366.0697.

Example 10

N-[Chloro-(3-methoxy carbonyl-phenyl)methylene]-N'-[chloro-(2-nitro-phenyl)methylene]hydrazine (27) and 3-[5-(2-nitro-phenyl)-[1,3,4] oxadiazol-2-yl]-benzoic methyl ester (28)

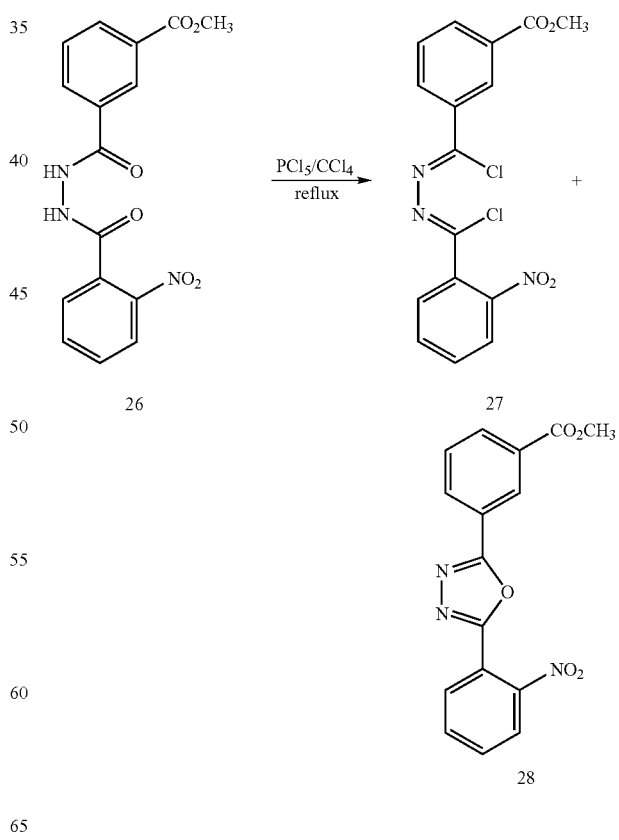

The same procedure as applied for 20 and 21 was employed.

Compound 27: 58% yield, white solid, m.p. 100° C.; $^1$H NMR (599 MHz, acetone-d$_6$, 300° K) δ 8.71 (s, 1H), 8.36 (d, J=7.8 Hz, 1H), 8.24 (d, J=8.3 Hz, 1H), 8.17 (d, J=8.1 Hz, 1H), 7.99 (d, J=7.6 Hz, 1H), 7.97 (t, J=7.6 Hz, 1H), 7.90 (t, J=8.1 Hz, 1H), 7.41 (t, J=7.8 Hz, 1H), 3.95 (s, 3H); $^{13}$C NMR (150 MHz, DMSO-d$_6$, 300° K) δ 166.3, 148.8, 144.7, 140.6, 134.6, 134.4, 133.8, 133.4 (2C), 132.1, 132.0, 130.3, 130.1, 129.8, 125.7, 52.7; HRMS (MALDI-FTMS) calcd for C$_{16}$H$_{11}$Cl$_2$N$_3$O$_4$+H$^+$: 380.0199, found 380.0183.

Compound 28: 23% yield, white solid, m.p.; $^1$H NMR (599 MHz, acetone-d$_6$, 300° K) δ 8.66 (s, 1H), 8.32 (d, J=8.0 Hz, 1H), 8.24 (d, J=7.7 Hz, 1H), 8.20 (d, J=8.1 Hz, 1H), 8.18 (d, J=7.8 Hz, 1H), 8.00 (t, J=7.2 Hz, 1H) 7.97 (t, J=7.6 Hz, 1H), 7.78 (t, J=7.7 Hz,1H), 3.95 (s, 3H); $^{13}$C NMR (150 MHz, acetone-d$_6$, 300° K) δ 166.2, 165.4, 162.2, 134.3, 134.1, 133.5, 132.4, 132.3, 131.8, 130.8, 128.3, 125.6, 125.0, 118.7, 52.7; HRMS (MALDI-FTMS) calcd for C$_{16}$H$_{11}$N$_3$O$_5$+H$^+$: 326.0771, found 326.0775.

Example 11

3-(2-Nitro-phenyl)-6-(3-benzoic acid methyl ester)-[1,2,4,5] tetrazine (29)

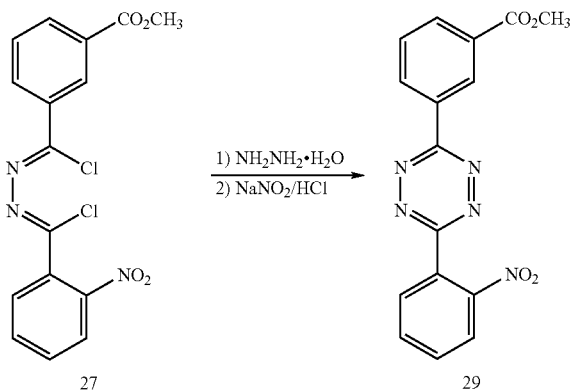

The preparation followed the same procedure (method B) as used for compound 23. (63% yield, based on recovered starting material 27), red solid, m.p. 170-171° C.; LRMS (ESI): m/z 338 (MH$^+$), 360 (MNa$^+$).

Example 12

Diels-Alder Reactions

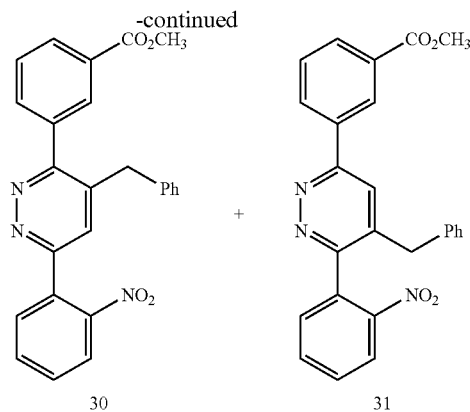

3-[4-Benzyl-6-(2-nitro-phenyl)-pyridazin-3-yl]-benzoic acid methyl ester (30) and 3-[5-Benzyl-6-(2-nitro-phenyl)-pyridazin-3-yl]-benzoic acid methyl ester (31). Tetrazine 29 (68 mg, 0.2016 mmol) and the appropriate aldehyde (61 mg, 0.4146 mmol) were mixed with dry peroxide-free THF (2 mL) at room temperature. A solution (200 μL) of 2.5% KOH in MeOH was added to the above mixture. After 2 min., the color of the reaction mixture turned from red to brown. The solvent was evaporated. The resulting residue was dissolved in EtOAc, washed with water, brine and dried over MgSO$_4$ and concentrated. The crude product was purified by flash column chromatography (from EtOAc:Hex:CH$_2$Cl$_2$=2:49:49 to EtOAc:Hex:CH$_2$Cl$_2$=8:46:46) to give 3-[4-Benzyl-6-(2-nitro-phenyl)-pyridazin-3-yl]-benzoic acid methyl ester 30 and 3-[5-Benzyl-6-(2-nitro-phenyl)-pyridazin-3-yl]-benzoic acid methyl ester 31 (69.9 mg, 0.16 mmol, 81% yield, 30/31=1.6:1).

Compound 30: white solid, m.p. 130° C.; $^1$H NMR (599 MHz, CDCl$_3$, 300° K) δ 8.22 (s, 1H), 8.11 (d, J=7.7 Hz, 1H), 7.98 (d, J=8.1 Hz, 1H), 7.74 (d, J=7.4 Hz, 1H), 7.66 (t, J=7.4 Hz, 1H), 7.61 (d, J=7.3 Hz, 1H), 7.55 (t, J=7.7 Hz, 1H), 7.52 (t, J=7.5 Hz, 1H), 7.25 (s, br, 1H), 7.22 (t, J=7.4 Hz, 2H), 7.17 (t, J=7.2 Hz, 1H), 6.94 (d, J=7.7 Hz, 2H), 4.10 (s, 2H), 3.86 (s, 3H); LRMS (ESI): m/z 426 (MH$^+$), 424 [M−H]$^-$, 460 [M+Cl]$^-$. The structure was further confirmed by X-ray crystallographic analysis.

Compound 31, white solid, $^1$H NMR (599 MHz, CDCl$_3$, 300° K) δ 8.62 (s,1H), 8.27 (d, J=7.8 Hz, 1H), 8.19 (d, J=7.9 Hz, 1H), 8.10 (d, J=7.6 Hz, 1H) 7.65-7.59 (m, 3H), 7.54 (t, J=7.6 Hz, 1H), 7.29 (d, J=7.3 Hz, 1H), 7.17 (t, J=7.4 Hz, 3H), 6.90 (d, J=7.3 Hz, 2H), 3.89 (s, 3H), 3.8 (s, 2H); LRMS (ESI): m/z 426 (MH$^+$), 424 [M−H]$^-$, 460 [M+Cl]$^-$. The structure was further confirmed by GOSY NMR experiment.

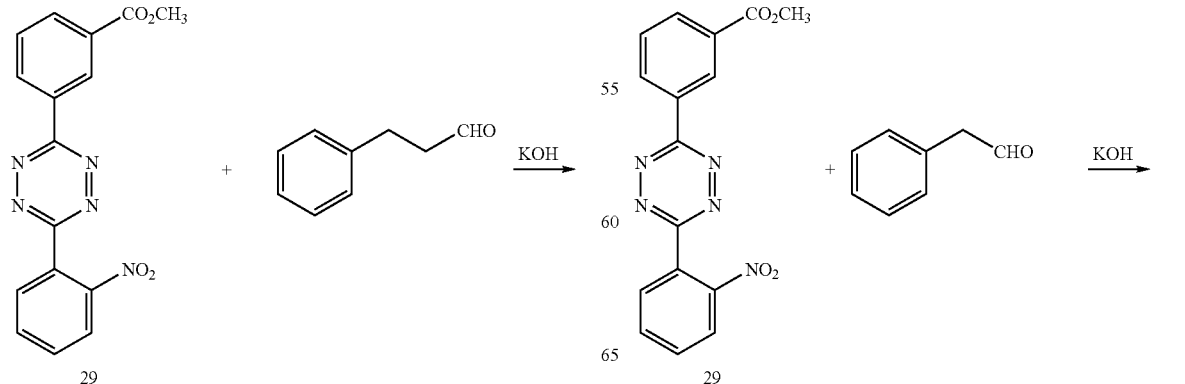

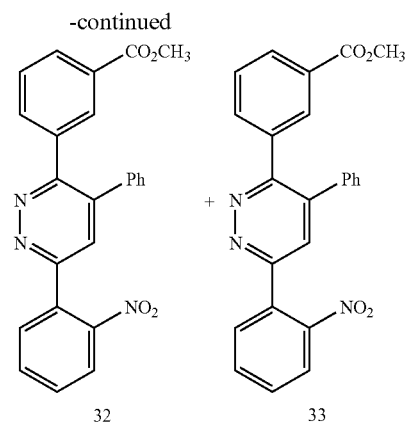

3-[6-(2-Nitro-phenyl)-4-phenyl-pyridazin-3-yl]-benzoic acid methyl ester (32)/(33). The preparation followed the same procedure for as used for compounds (30)/(31). White solid, 95% yield (32/33 =6:1). Compound 32: $^1$H NMR (599 MHz, CDCl$_3$, 300° K) δ 8.28 (s, 1H), 8.09 (d, J=8.1 Hz, 1H), 8.04 (d, J =7.8 Hz, 1H), 7.79 (t, J=8.0 Hz, 2H), 7.67 (t, J=7.4 Hz, 1H), 7.62 (d, J=7.8 Hz, 1H), 7.61 (s, 1H), 7.37 (t, J=7.6 Hz, 2H), 7.34 (t, J=7.5 Hz, 2H), 7.23 (d, J =7.1 Hz, 2H), 3.87 (s, 3H); $^{13}$C NMR (150 MHz, CDCl$_3$, 300° K) δ 166.5, 157.8, 157.3, 148.7, 139.2, 136.7, 136.0, 134.4, 133.1, 132.4, 131.9, 131.4, 130.4, 130.3, 130.1, 129.1(2C), 128.9 (2C), 128.2, 127.3, 124.9, 52.1; LRMS (ESI): m/z 412 (MH$^+$).

3-[4-(2-Hydroxy-ethyl)-6-(2-nitro-phenyl)-pyridazin-3-yl]-benzoic acid methyl ester (34) and 3-[4-(2-Hydroxy-ethyl)-6-(2-nitro-phenyl)-pyridazin-3-yl]-benzoic acid methyl ester (35). Tetrazine (29) (12.4 mg, 0.0368 mmol) and 2,3-dihydrofuran (7.7 mg, 0.1104 mmol ) in 1,4-dioxane (75 μL) were heated to 100° C. under N$_2$ for 5 mins. The color of reaction mixture turned from red to yellow. The solvent was evaporated and the residue was purified by flash column chromatography (4% MeOH in CH$_2$Cl$_2$) to give (34/35) (13.8 mg, 0.0364 mmol, 99% yield, 34/35=1.5:1) as a mixture.

Compound 34: $^1$H NMR (599 MHz, CDCl$_3$, 300° K) δ 8.21 (s, 1H), 8.08 (t, J=7.7 Hz, 1H), 7.97 (d, J=8.1 Hz, 1H), 7.75 (d, J=7.4 Hz, 1H), 7.69-7.51 (m, 4H), 7.61 (s, 1H), 3.86 (s, 3H), 3.76 (t, J=6.1 Hz, 2H), 2.88 (t, J=6.1 Hz, 2H); HRMS (MALDI-FTMS) calcd for C$_{20}$H$_{17}$N$_3$O$_5$+H$^+$: 380.1241, found 380.1238; LRMS (ESI): m/z 380 (MH$^+$), 402 (MNa$^+$), 414 [M+Cl]$^-$.

Compound 35: $^1$H NMR (599 MHz, CDCl$_3$, 300° K) δ 8.63 (s, 1H), 8.14 (d, J=8.2 Hz, 1H), 8.08 (t, J=7.7 Hz, 1H), 7.92 (s, 1H), 7.69-7.51 (m, 4H), 7.44 (d, J=7.4 Hz, 1H); 3.89 (s, 3H), 3.76 (t, J=5. Hz, 2H), 2.71 (t, J=5.9 Hz, 2H); HRMS (MALDI-FTMS) calcd for C$_{20}$H$_{17}$N$_3$O$_5$+H$^+$: 380.1241, found 380.1238; LRMS (ESI): m/z 380 (MH$^+$), 402 (MNa$^+$), 414 [M+Cl]$^-$.

The following compounds were prepared by the same protocol.

Pyridazines (36a/b), (37a/b) and (38a/b)

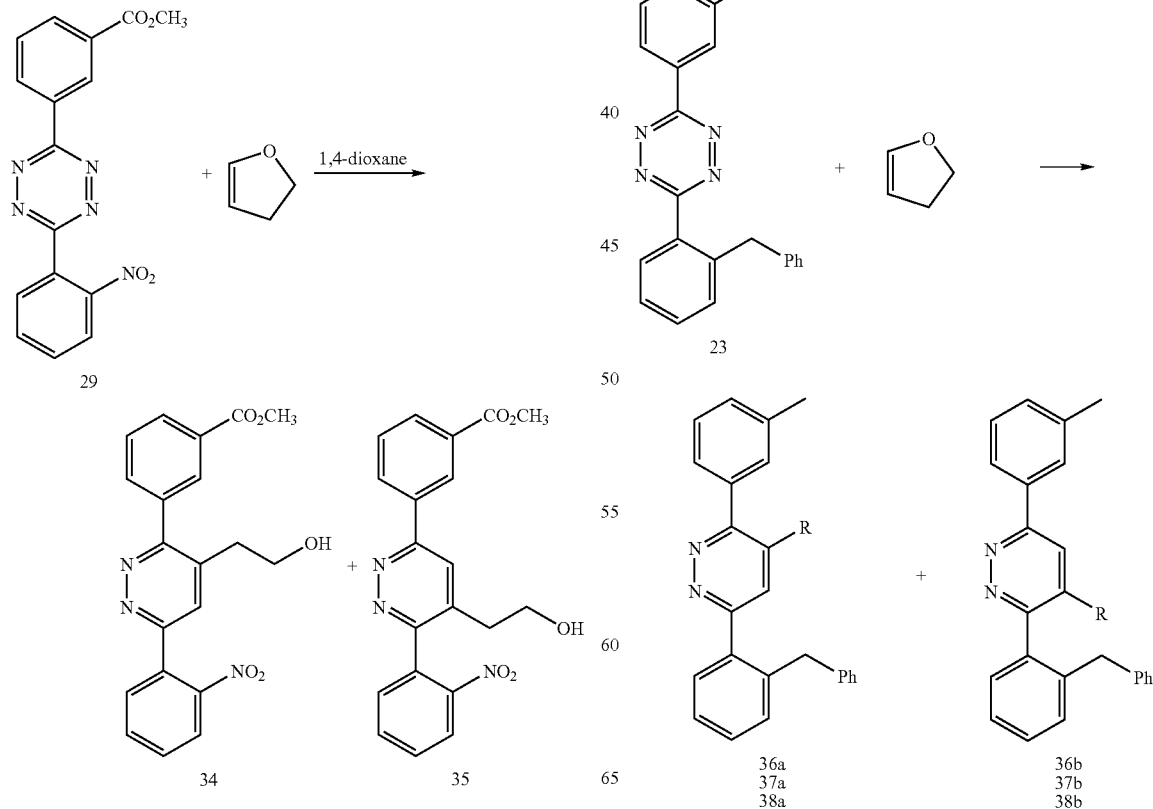

-continued

36 R = 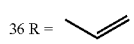

37 R = 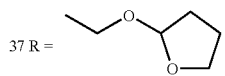

38 R = 

Compounds 36/a/b: a mixture of two regioisomers, 11% yield, white semi-solid. HRMS (MALDI-FTMS) calcd for $C_{26}H_{22}N_2+H^+$: 363.1856, found 363.1859; LRMS (ESI): m/z 363 ($MH^+$), 385 ($MNa^+$), 361 $[M-H]^-$, 397 $[M+Cl]^-$.

Compound 37a: 44% yield, white semi-solid; HRMS (MALDI-FTMS) calcd for $C_{30}H_{30}N_2O_2+H^+$: 451.2380, found 451.2379; LRMS (ESI): m/z 451 ($MH^+$), 473 ($MNa^+$), 485$[M+Cl]^-$.

Compound 37b: 26% yield, white semi-solid, HRMS (MALDI-FTMS) calcd for $C_{30}H_{30}N_2O_2+H^+$: 451.2380, found 451.2380; LRMS (ESI): m/z 451 ($MH^+$), 449$[M-H]^-$.

Compound 38a: white semi-solid. 17% yield, HRMS (MALDI-FTMS) calcd for $C_{26}H_{24}N_2O+H^+$: 381.1961, found 381.1955. The structure was further confirmed by GOSY NMR experiment.

Compound 38b: 11% yield, LRMS (ESI): m/z 381 ($MH^+$), 403 ($MNa^+$), 415$[M+Cl]^-$.

3-(2-Benzyl-phenyl)-6-m-tolyl-pyridazine (40)

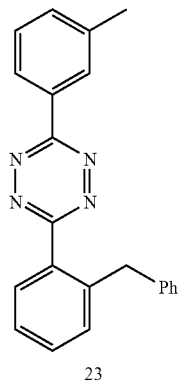

23

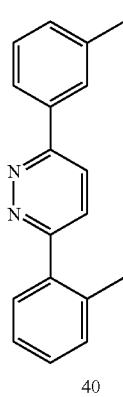

40

Compound 40: 74% yield, white solid; HRMS (MALDI-FTMS) calcd for $C_{24}H_{20}N_2+H^+$: 337.1699, found 337.1699.

Pyridazines (41a/b) and (42a/b)

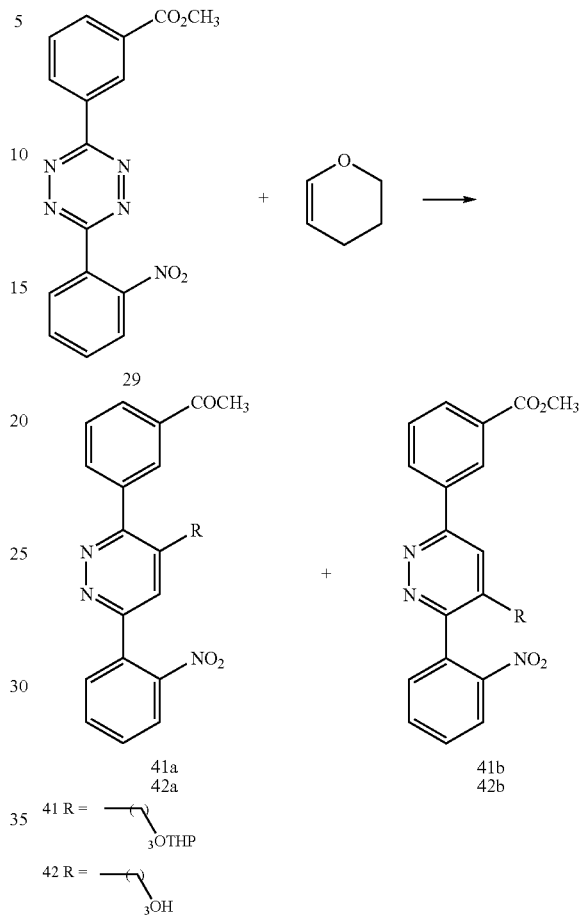

41a
42a 41b
42b

41 R = ⟶(⟩₃OTHP

42 R = ⟶(⟩₃OH

Compounds 41a/b: a mixture of two regio-isomers, 86% yield (41a/b=1.5:1), HRMS (MALDI-FTMS) calcd for $C_{26}H_{27}N_3O_6+H^+$: 478.1980, found 478.1993; LRMS (ESI): m/z 478 ($MH^+$), 500 ($MNa^+$), 476 $[M-H]^-$, 512 $[M+Cl]^-$.

Compound 41a: $^1$H NMR (599 MHz, CDCl$_3$, 300° K) δ 8.25 (s, 1H), 8.11 (t, J=7.4 Hz, 1H), 8.00 (d, J=8.2 Hz, 1H), 7.78 (d, J=7.7 Hz, 1H), 7.73-7.54 (m, 4H), 7.49 (s, 1H), 4.39 (d, J=3.3 Hz, 1H), 3.87 (s, 3H), 3.67-3.60 (m, 2), 3.37-3.34 (m, 1H), 3.28-3.25 (m, 1H), 2.81-2.77 (m, 2H), 1.81-1.36 (m, 8H).

Compound 41b: $^1$H NMR (599 MHz, CDCl$_3$, 300° K) δ 8.66 (s, 1H), 8.39 (d, J=7.6 Hz, 1H), 8.11 (t, J=7.4 Hz, 1H), 7.85 (s, 1H), 7.73-7.54 (m, 4H), 7.46 (d, J=7.5 Hz, 1H), 4.39 (d, J=3.3 Hz, 1H), 3.91 (s, 3H), 3.67-3.60 (m, 2H), 3.37-3.34 (m, 1H), 3.28-3.25 (m, 1H), 2.60-2.57 (m, 2H), 1.81-1.36 (m, 8H).

Compounds 42a/b: a mixture of two regio-isomers, 12% yield (42a/b=1.5:1), HRMS (MALDI-FTMS) calcd for $C_{21}H_{19}N_3O_5+H^+$: 394.1397, found 394.1403; LRMS (ESI): m/z 394 ($MH^+$), 428 $[M+Cl]^-$.

Compound 42a: $^1$H NMR (599 MHz, CDCl$_3$, 300° K) δ 8.24 (s, 1H), 8.11 (t, J=7.1 Hz, 1H), 8.01 (d, J=8.2 Hz, 1H), 7.81 (d, J=7.6 Hz, 1H), 7.72-7.54 (m, 4H), 7.47 (s, 1H), 3.88 (s, 3H), 3.54 (t, J=5.9 Hz, 2H), 2.80 (t, J=7.5 Hz, 2H), 1.79-1.73 (m, 2H).

Compound 42b: $^1$H NMR (599 MHz, CDCl$_3$, 300° K) δ 8.65 (s, 1H), 8.39 (d, J=7.6 Hz, 1H), 8.11 (t, J=7.1 Hz, 1H), 7.83 (s, 1H), 7.72-7.54 (m, 4H), 7.45 (d, J =7.5 Hz, 1H), 3.91 (s, 3H), 3.54 (t, J=5.9 Hz, 2H), 2.59 (t, J=7.5 Hz, 2H), 1.79-1.73 (m, 2H).

The regio-isomers were separated by HPLC:

Compound 42a: semi-solid, $^1$H NMR (599 MHz, CDCl$_3$, 300° K) δ 8.30 (s, 1H), 8.17 (d, J=7.9 Hz, 1H), 8.06 (d, J=8.2 Hz, 1H), 7.86 (d, J=7.5 Hz, 1H), 7.77-7.73 (m, 2H), 7.65 (t, J=7.3 Hz, 1H), 7.61 (t, J=8.1 Hz, 1H), 7.54 (s, 1H), 3.94 (s, 3H), 3.59 (t, J=5.9 Hz, 2H), 2.85 (t, J=7.7 Hz, 2H), 1.80 (quintet, J=6.2 Hz, 2H); $^{13}$C NMR (150 MHz, CDCl$_3$, 300° K) δ 166.6, 160.3, 157.3, 148.7, 140.0, 136.9, 133.7, 133.1, 132.6, 131.9, 130.38, 130.36, 130.21, 130.18, 128.8, 127.1, 124.8, 61.2, 52.3, 32.0, 28.2; HRMS (MALDI-FTMS) calcd for C$_{21}$H$_{19}$N$_3$O$_5$+H$^+$: 394.1397, found 394.1403; LRMS (ESI): m/z 394 (MH$^+$), 428 [M+Cl]$^-$.

Method B for Preparation of pyridazines (42a/b)

Tetrazine 29 (16.2 mg, 0.048 mmol), 2,3-dihydropyran (20.2 mg, 0.240 mmol) and DIEA (8.4 μL, 0.048 mmol) in 1,4-dioxane (100 μL) were heated to 100° C. under N$_2$ for 8 hr. The color of reaction mixture turned from red to yellow. The solvent was evaporated and the residue was purified by flash column chromatography (2% MeOH in CH$_2$Cl$_2$) to give (42a/b) (17.1 mg, 0.0435 mmol, 91% yield, 42a/b=1.5:1) as a mixture.

Example 13

Deprotection of THF and DHP Ethers

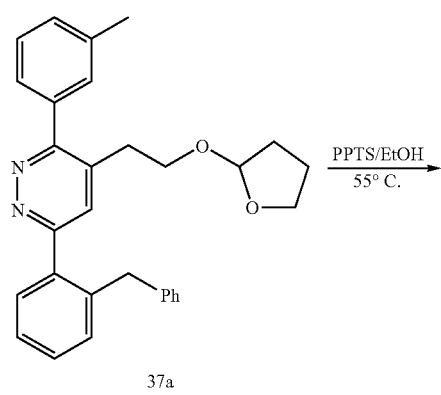

37a

2-[6-(2-Benzyl-phenyl)-3-m-tolyl-pyridazin-4-yl]-ethanol (38a). A solution of 37a (10.2 mg, 0.0226 mmol) and PPTS (5.8 mg, 0.0226 mmol) in ethanol (1.5 mL) was stirred at 50° C. for 12 hr. The solvent was evaporated, and the residue was purified by flash column chromatography (1% MeOH in CH$_2$Cl$_2$) to give 38a (7.6 mg, 0.0200 mmol, 88% yield) as a white solid.

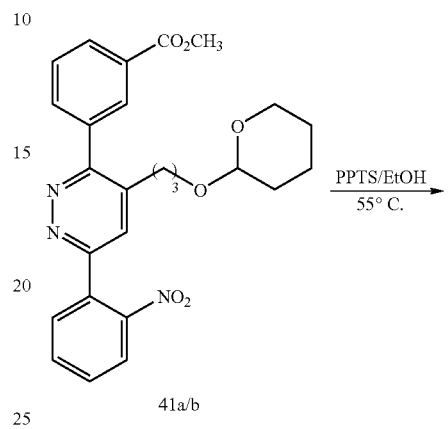

41a/b

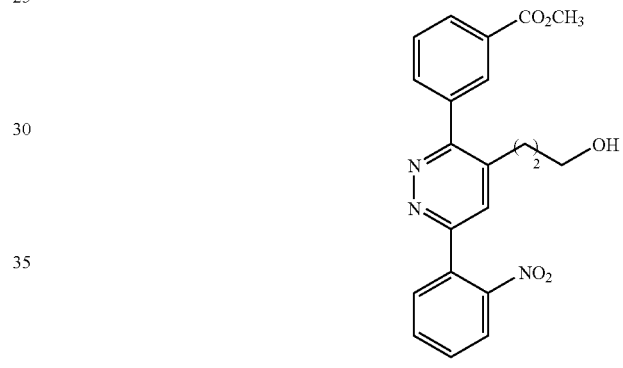

42a/b

3-[4-(Hydroxy-propyl)-6-(2-nitro-phenyl)-pyridazin-3-yl]-benzoic acid methyl ester (42). Deprotection of the THP ether followed the same procedure as used for deprotection of the THF ether above 95% yield.

Example 14

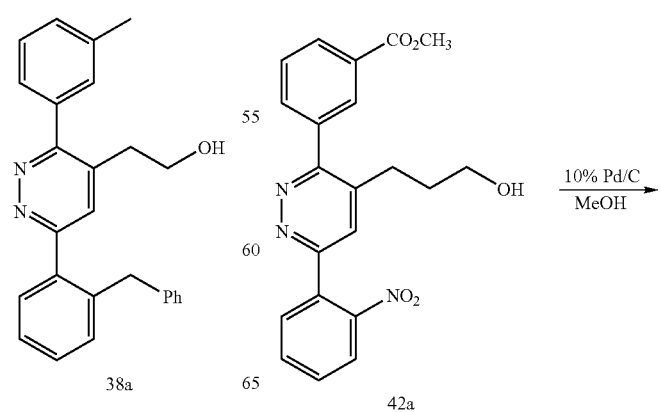

42a

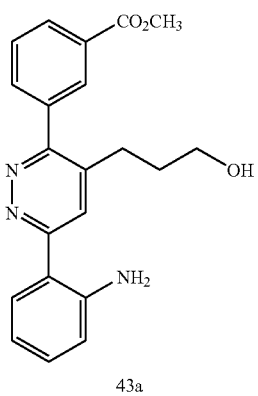

43a

3-[6-(2-Amino-phenyl)-4-(3-hydroxy-propyl)-pyridazin-3-yl]-benzoic acid methyl ester (43a). To a solution of nitro compound 42a (69 mg, 0.175 mmol) suspended in MeOH (1 mL), was added 10% Pd/C in one portion. The reaction was carried out in a hydrogenation flask at 50 psig for 8 hr. The catalyst was filtered off, and the filtrate was evaporated under reduced pressure to afford 43a (63 mg, 0.173 mmol, 99% yield) as pale yellow solid. m.p. 141° C.; LRMS (ESI): m/z 364.2 (MH$^+$), 386.2 (MNa$^+$) 362.1 [M−H]$^−$, 398.1 [M+Cl]$^−$.

Example 15

Template Derivatization I

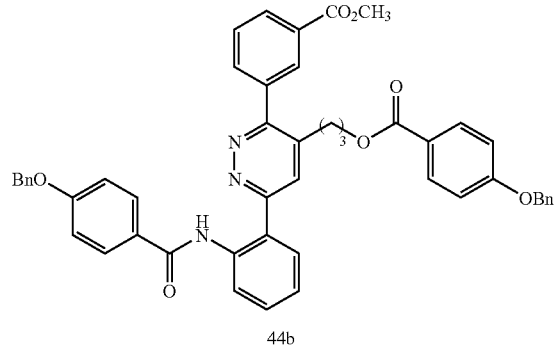

44b

Step 1: To a solution of 4-benzyloxy-benzoyl chloride (1.3 g, 5.270 mmol) in 10 mL dry $CH_2Cl_2$ was transferred (43a/b) (736 mg, 2.025 mmol) in $CH_2Cl_2$ (5 mL). Then 1.6 mL of pyridine was added to the reaction mixture. The reaction was stirred at room temperature for 8 hr. It was diluted with EtOAc and washed by water, dried over $MgSO_4$ and, evaporated. The crude product is purified by flash column chromatography (2-5% EtOAc in $CH_2Cl_2$ for 44a and 8-10% EtOAc in n-hexane for 44b) to give 44a (889 mg, 1.134 mmol, 56% yield) and 44b (554 mg, 0.707 mmol, 23% yield).

Compound 44a: pale yellow solid, HRMS (MALDI-FTMS) calcd for $C_{49}H_{41}N_3O_7+H^+$: 784.3017, found 784.3002; LRMS (ESI): m/z 784.3 (MH$^+$), 806.4 (MNa$^+$), 782.2 [M−H]$^−$, 818.2 [M+Cl]$^−$.

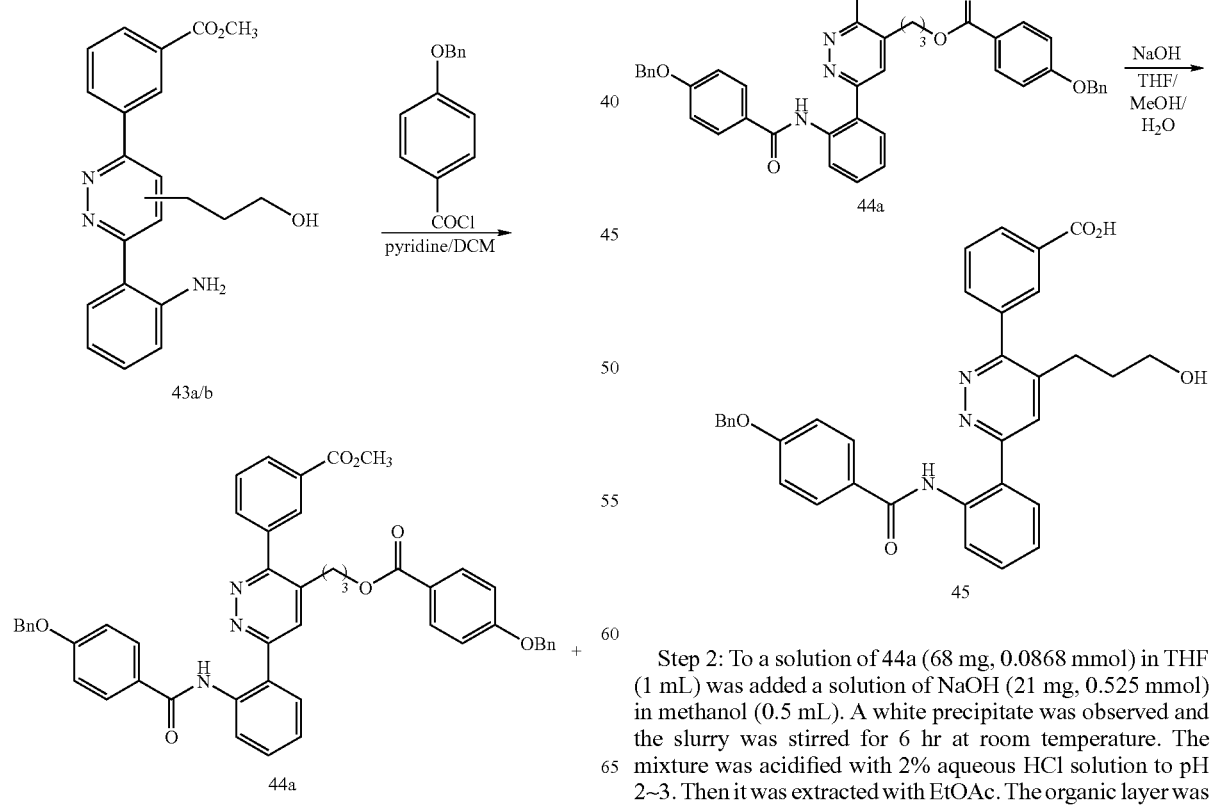

Step 2: To a solution of 44a (68 mg, 0.0868 mmol) in THF (1 mL) was added a solution of NaOH (21 mg, 0.525 mmol) in methanol (0.5 mL). A white precipitate was observed and the slurry was stirred for 6 hr at room temperature. The mixture was acidified with 2% aqueous HCl solution to pH 2~3. Then it was extracted with EtOAc. The organic layer was washed with brine, dried over $MgSO_4$ and concentrated. The crude product was purified by flash column chromatography (10% MeOH in EtOAc) to give 45 (40 mg, 0.715 mmol, 82% yield) as a pale yellow solid, m.p. 112-115° C.; HRMS (MALDI-FTMS) calcd for $C_{34}H_{29}N_3O_5$+H: 560.2180, found 560.2177; LRMS (ESI): m/z 560.3 (MH$^+$), 582.2 (MNa$^+$), 558.1 [M−H]$^-$.

Compound 48: 99% yield, pale yellow solid, 92-93° C.; HRMS (MALDI-FTMS) calcd for $C_{38}H_{38}N_4O_4$+H: 615.2966, found 615.2965; LRMS (ESI): m/z 615 (MH$^+$), 637 (MNa$^+$).

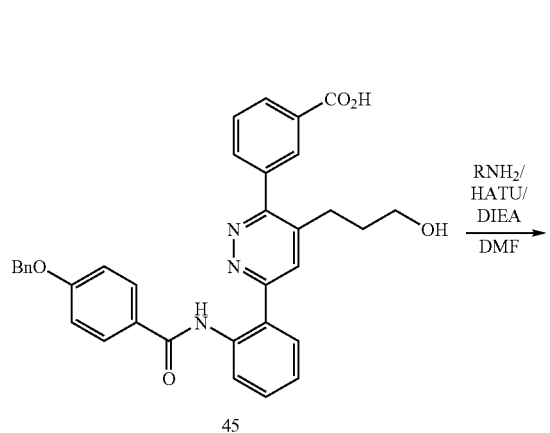

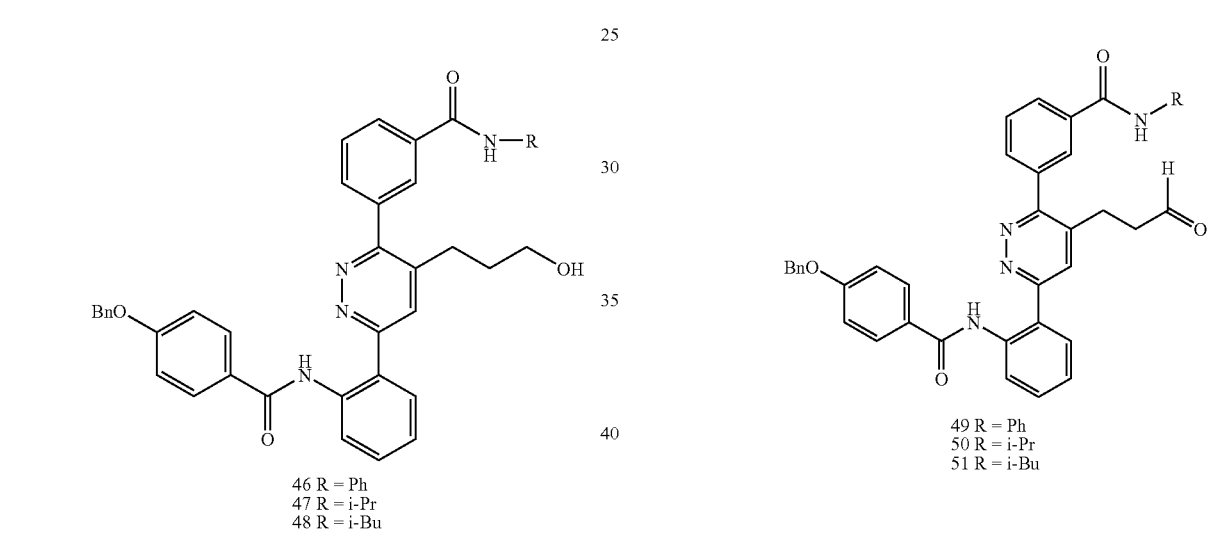

Step 3: To a mixture of 45 (281 mg, 0.5021 mmol) and HATU (420 mg, 1.1046 mmol) in DMF was added DIEA (348 uL, 2.0 mmol) and amine RNH$_2$. The reaction was stirred for 10 hr. The mixture was diluted with EtOAc and washed with water. The organic layer was dried over MgSO$_4$ and concentrated. The crude product was purified by column chromatography (15-20% EtOAc in CH$_2$Cl$_2$) to give compound the target compounds.

Compound 46: (237 mg, 0.37 mmol, 74% yield) as pale yellow solid. HRMS (MALDI-FTMS) calcd for $C_{40}H_{34}N_4O_4$+H: 635.2653, found 635.2662; LRMS (ESI): m/z 635.4 (MH$^+$), 657.4 (MNa$^+$), 633.2 [M−H]$^-$, 669.2 [M+Cl]$^-$.

Compound 47: 99% yield, pale yellow solid, 193-194° C.; HRMS (MALDI-FTMS) calcd for $C_{37}H_{36}N_4O_4$+H: 601.2809, found 601.2829; LRMS (ESI): m/z 601 (MH$^+$), 623 (MNa$^+$).

Step 4: To a solution of oxalylchloride (2.0M in DCM, 232 uL, 0.4648 mmol) at −78° C. was added 5 mL CH$_2$Cl$_2$ solution of DMSO (66 uL, 14.081 mmol). 10 min later, a solution of 46 (118 mg, 0.1859 mmol) in CH$_2$Cl$_2$ (5 mL) was transferred to the above reaction mixture. It was stirred at −78° C. for an additional 30 min. TEA (0.52 mL, 3.718 mmol) was added at once. The reaction mixture was maintained at this temperature for 15 min, then slowly warmed up to room temperature. The reaction mixture was diluted with EtOAc and washed with water, brine, dried over MgSO$_4$ and concentrated. The residue was purified by flash column chromatography (5-10% EtOAc in CH$_2$Cl$_2$) to give 49 (63 mg, 0.0996 mmol, 54% yield) as yellow solid. m.p. 131° C.; HRMS (MALDI-FTMS) calcd for $C_{40}H_{32}N_4O_4$+H: 633.2496, found 633.2508; LRMS (ESI): m/z 633.2 (MH$^+$), 631.2 [M−H]$^-$.

Compounds 50 and 51 were obtained similarly.

Compound 50: 60% yield, yellow solid; HRMS (MALDI-FTMS) calcd for $C_{38}H_{36}N_4O_4$+H: 613.2809, found 613.2822; LRMS (ESI): m/z 613 (MH$^+$), 611 [M−H]$^-$.

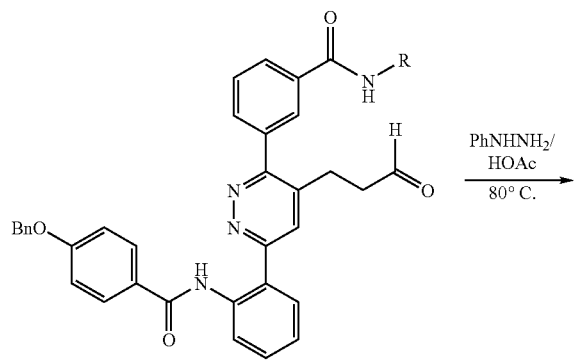

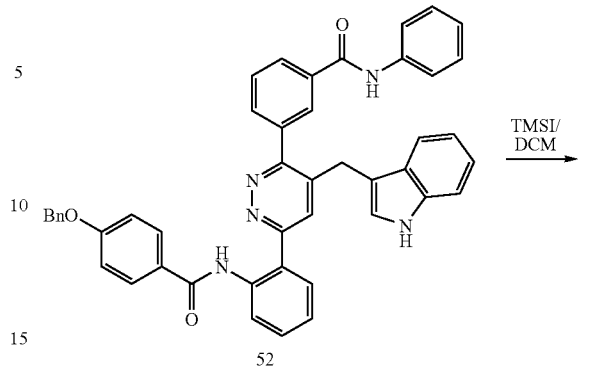

49 R = Ph
50 R = i-Pr
51 R = i-Bu

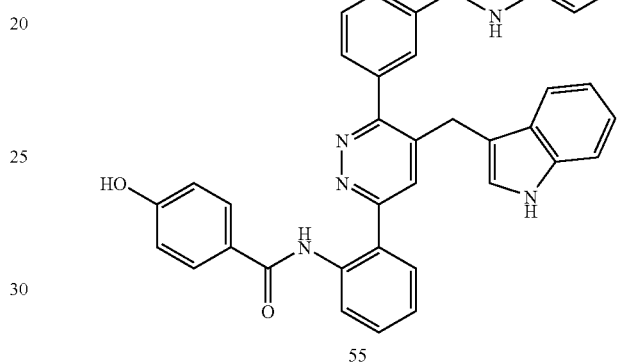

52 R = Ph
53 R = i-Pr
54 R = i-Bu

55

Step 5: To a solution of aldehyde 49 (102 mg, 0.1612 mmol) in AcOH (2 mL) was added phenylhydrazine hydrochloride (35 mg, 0.2418 mmol) under $N_2$ atmosphere. The reaction was stirred at room temperature for 10 mins. Then it was warmed up to 80° C. for 3 hr. The reaction mixture was cooled down and diluted with EtOAc. The combined organic layer was washed with water, sodium bicarbonate solution and brine to neutral condition. Then it was dried over $MgSO_4$ and concentrated. The residue was purified by flash column chromatography (5% EtOAc in $CH_2Cl_2$) to give 52 (45 mg, 0.0638 mmol, 40% yield) as a pale yellow solid. HRMS (MALDI-FTMS) calcd for $C_{46}H_{35}N_5O_3$+H: 706.2813, found 706.2837; LRMS (ESI): m/z 706.3 (MH$^+$), 740.3 [M+Cl]$^-$.

Compounds 53 and 54 were obtained similarly.

Compound 53: 50% yield, pale yellow solid. HRMS (MALDI-FTMS) calcd for $C_{43}H_{37}N_5O_3$+H: 672.2969, found 672.2940; LRMS (ESI): m/z 672 (MH$^+$), 694 (MNa$^+$), 670 [M−H]$^-$, 706 [M+Cl]$^-$.

Compound 54: 38% yield, pale yellow solid. HRMS (MALDI-FTMS) calcd for $C_{44}H_{39}N_5O_3$+H: 686.3126, found 686.3115; LRMS (ESI): m/z 686 (MH$^+$), 708 (MNa$^+$), 720 [M+Cl]$^-$.

Step 6: To a solution of pyridazine compound 52 (6.9 mg, 0.0098 mmol) suspended in $CH_2Cl_2$ (0.5 mL), was added iodotrimethylsilane (14 μL, 0.098 mmol) under argon atmosphere. The color of the reaction turned from yellow to orange immediately and a precipitate formed. The reaction mixture was stirred for 48 hr. at rt. MeOH (100 μL) was added to quench the reaction and the mixture was then diluted with ether. Then reaction mixture was washed with water and brine, dried over $MgSO_4$ and concentrated to yield the crude product, which was purified by flash column chromatography (1-2% MeOH in $CH_2Cl_2$) to yield 55 (4.1 mg, 0.0067 mmol, 68% yield) as a pale yellow solid. HRMS (MALDI-FTMS) calcd for $C_{39}H_{29}N_5O_3$+H: 616.2343, found 616.2360; LRMS (ESI): m/z 616.2 (MH$^+$), 638.2 (MNa$^+$), 614.3 [M−H]$^-$, 650.2 [M+Cl]$^-$.

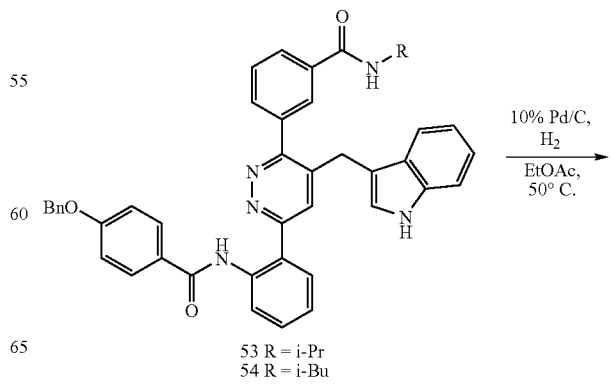

53 R = i-Pr
54 R = i-Bu

-continued

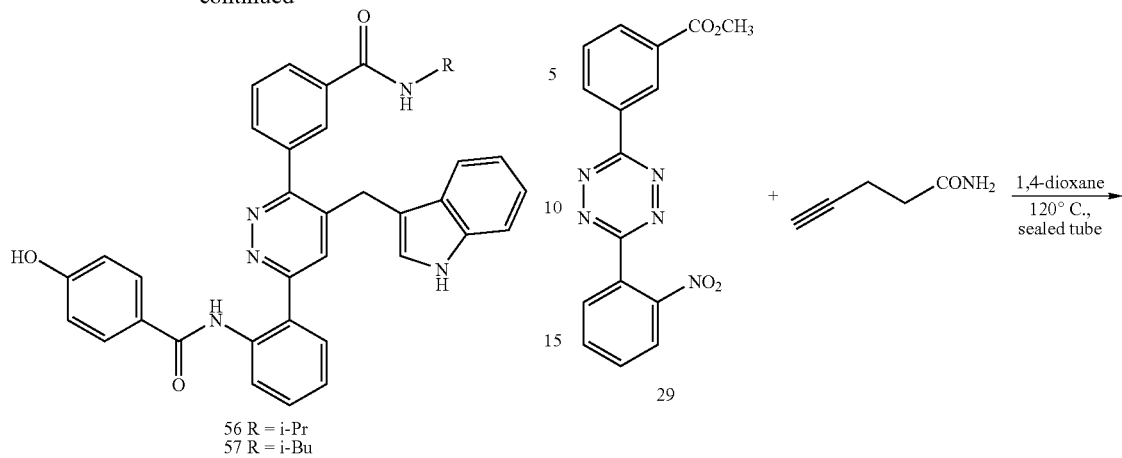

56 R = i-Pr
57 R = i-Bu

Step 7: To a solution of compound 53 (19 mg, 0.0283 mmol) suspended in EtOAc (1 mL), was added 10% Pd/C in one portion. The mixture was stirred for 8 hr. at 50° C. under an atmosphere of $H_2$. The catalyst was filtered off through a pad of celite, and the filtrate was evaporated under reduced pressure. The crude product was purified by flash column chromatography (2% MeOH in $CH_2Cl_2$) to afford 56 (13.8 mg, 0.0237 mmol, 84% yield) as pale yellow solid. HRMS (MALDI-FTMS) calcd for $C_{36}H_{31}N_5O_3$+H: 582.2500, found 582.2511; LRMS (ESI): m/z 582 (MH$^+$), 604 (MNa$^+$), 580 [M−H]$^−$, 616 [M+Cl]$^−$.

Compound 57 was obtained similarly.

Compound 57: 72% yield, pale yellow solid. HRMS (MALDI-FTMS) calcd for $C_{37}H_{33}N_5O_3$+H: 596.2656, found 596.2656; LRMS (ESI): m/z 596 (MH$^+$), 618 (MNa$^+$), 594 [M−H]$^−$, 630 [M+H]$^−$.

Example 16

Template Derivatization II

A. Template Generation

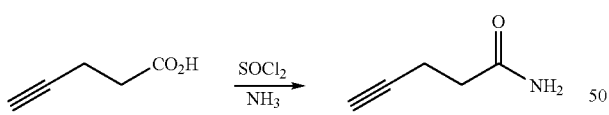

4-Pentynoic Acid Amide. A solution of 2.2 g (21.3 mmol) of 4-pentynoic acid in 20 mL of dry benzene was treated with 1.7 mL (23.4 mmol) of $SOCl_2$, and the reaction mixture was heated at reflux for 4 hr. At the end of this period, the excess $SOCl_2$ and benzene were removed under reduced pressure, and the residue was taken up in 10 mL of anhydrous THF, cooled to −78° C., and treated with 1.5 mL of dry $NH_3$ condensed from a cylinder. The reaction mixture was then allowed to slowly warm up to room temperature and was then stirred for an additional 8 hr. The THF was removed under reduced pressure, the residue was dissolved in 100 mL EtOAc and Washed with water, brine then dried over $Mg_2SO_4$ and concentrated under reduced pressure. The residue was crystallized from EtOAc to afford 486 mg (5.0 mmol, 23% yield) of 4-pentynoic acid amide as a colorless crystals.

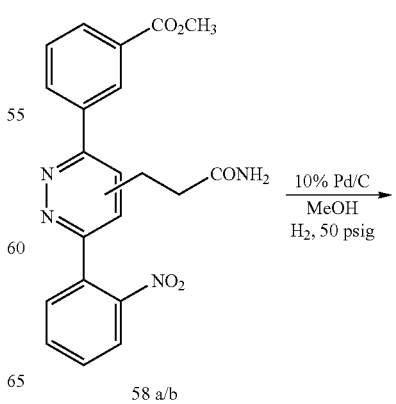

Diels Alder reaction. Tetrazine 29 (200 mg, 0.593 mmol) and 4-pentynoic acid amide (132 mg, 1.359 mmol) in 1,4-dioxane (600 μL) were heated to 120-130° C. in a sealed tube for 27 hr. The color of the reaction mixture turned from red to brown. The solvent was evaporated and the resulting residue was purified by flash column chromatography (2% to 3% MeOH in DCM) to give 58a/b (229 mg, 0.563 mmol, 95% yield) as a mixture of two region-isomers (~1:1 ratio). HRMS (MALDI-FTMS) calcd for $C_{21}H_{18}N_4O_5$+H: 407.1350, found 407.1353.

-continued

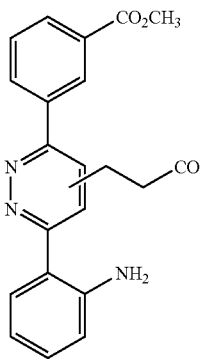

59 a/b

Nitro group reduction. To a solution of nitro compound 58a/b (367 mg, 0.903 mmol) suspended in MeOH (1 mL), was added 10% Pd/C in one portion. The reaction was carried out in hydrogenation flask at 50 psig for 20 hr. The catalyst was filtered off, and the filtrate was evaporated under reduced pressure to afford 59a/b (218 mg, 0.0983 mmol, 94% yield) as a pale yellow cotton like solid, which was used in the next step without further purification. HRMS (MALDI-FTMS) calcd for $C_{21}H_{20}N_4O_3$+H: 377.1608, found 377.1612.

B. Template Derivatization

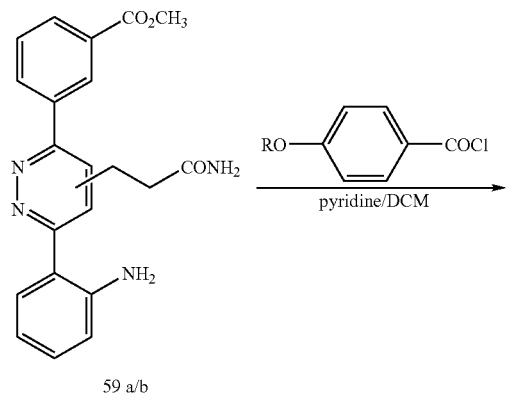

59 a/b

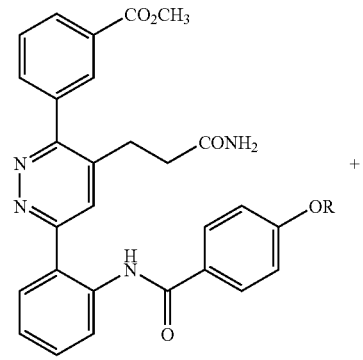

60a R = Bn
61a R = Ac

-continued

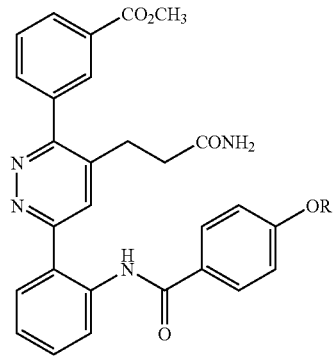

60b R = Bn
61b R = Ac

Step 1: Acylation. To a solution of 59a/b (300 mg, 0.797 mmol) in DCM (2 mL) was added 4-benzyloxy-benzoyl chloride (271 mg, 0.876 mmol) in 2 mL dry DCM. Then 0.5 mL of pyridine was added to the reaction mixture. The reaction mixture was stirred at room temperature for 12 hr. It was diluted with EtOAc, washed with water, dried over $MgSO_4$ and evaporated. The crude product was purified by flash column chromatography (10-15% acetone in DCM) to give 60a (126 mg, 0.215 mmol, 27% yield) and 60b (112 mg, 0.191 mmol, 24% yield).

Compound 60a: $^1$H NMR (599 MHz, DMF-$d_7$, 300° K) δ 13.1 (s, 1H), 8.78 (d, J=8.1 Hz, 1H), 8.41 (s, 1H), 8.33 (s, 1H), 8.19 (d, J=7.7 Hz, 1H), 8.11 (d, J=7.7 Hz, 1H), 8.08 (d, J=8.6 Hz, 2H), 8.07 (d, J=7.7 Hz, 1H), 7.78 (t, J=7.7 Hz, 1H), 7.61 (t, J=7.7 Hz, 1H), 7.52 (d, J=7.7 Hz, 2H), 7.41 (t, J=7.7 Hz, 2H), 7.36-7.34 (m, 2H), 7.20 (d, J=8.7 Hz, 2H), 6.82 (s, 1H), 5.23 (s, 2H), 3.95 (s, 3H), 3.09 (t, J=7.5 Hz, 2H), 2.65 (t, J=7.5 Hz, 2H); $^{13}$C NMR (150 MHz, DMF-$d_7$, 300° K) δ172.7, 166.8, 165.3, 162.0, 160.3, 160.0, 141.0, 138.9, 137.3, 137.0, 133.9, 131.3, 131.1, 130.6, 130.5, 129.6 (2C), 129.4, 129.3, 128.9 (2C), 128.4, 128.0, 127.9 (2C), 127.1, 124.0, 123.5, 122.6, 115.1 (2C), 70.5, 52.6, 34.6, 27.7; HRMS (MALDI-FTMS) calcd for $C_{35}H_{30}N_4O_5$+H$^+$: 587.2289, found 587.2286.

Compound 60b: $^1$H NMR (599 MHz, $CD_2Cl_2$, 300° K) δ 9.72 (s, 1H), 8.62 (s, 1H), 8.23 (d, J=7.6 Hz, 1H), 8.09 (d, J=7.6 Hz, 1H), 7.95 (d, J=8.2 Hz, 1H), 7.90 (s, 1H), 7.77 (d, J=8.7 Hz, 2H), 7.54 (t, J=7.8 Hz, 1H), 7.48 (t, J=7.7 Hz, 1H), 7.38-7.33 (m, 5H), 7.31-7.28 (m, 2H), 6.94 (d, J=8.7 Hz, 2H), 5.88 (s, 1H), 5.29 (s, 1H), 5.04 (s, 2H), 3.93 (s, 3H), 2.98 (t, J=7.4 Hz, 2H), 3.29 (t, J=7.4 Hz, 2H); $^{13}$C NMR (150 MHz, $CD_2Cl_2$, 300° K) δ 173.2, 166.8, 165.9, 162.1, 159.9, 157.4, 141.5, 136.9, 136.7, 136.4, 131.5, 131.4, 131.2, 130.3, 130.2, 129.6 (2C), 129.5, 128.9 (2C), 128.5, 128.3, 127.9 (2C), 127.0, 126.5, 125.7, 125.5, 115.0 (2C), 70.4, 52.6, 34.4, 28.1.

Compounds 61a/b were obtained similarly.

Compound 61a: 41% yield. HRMS (MALDI-FTMS) calcd for $C_{30}H_{26}N_4O_6$+H$^+$: 539.1925, found 539.1923.

Compound 61b: 31% yield.

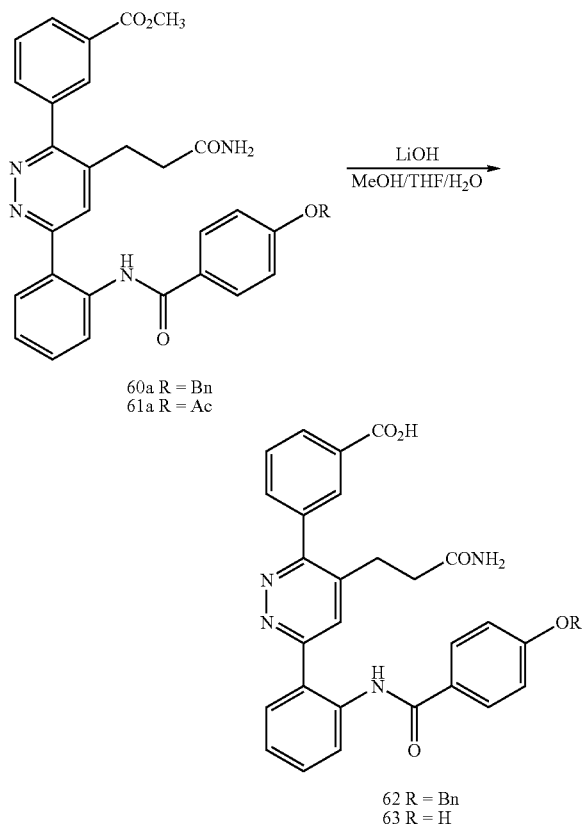

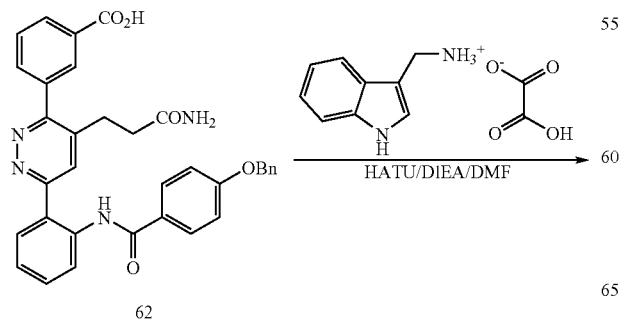

Step 2: Saponification. To a solution of 60a (44.4 mg, 0.0757 mmol) in THF (0.5 mL) and MeOH (0.5 mL) was added a solution of LiOH (4 mg, 0.167 mmol) in $H_2O$ (0.2 mL). A white precipitate was observed and the slurry was stirred for 12 hr. at room temperature. The mixture was diluted with EtOAc and acidified with 2% HCl aqueous solution to pH 2~3. Then it was extracted with EtOAc. The organic layer was washed with brine, dried over $MgSO_4$ and concentrated to give crude product 62 (42 mg, 0.0733 mmol, 97% yield) as yellow solid. HRMS (MALDI-FTMS) calcd for $C_{34}H_{28}N_4O_5+H^+$: 573.2132, found 573.2136.

Compound 63 was obtained similarly, with concurrent deprotection of the acetyl group.

Compound 63: 86% yield. Purified by HPLC (βsil $C_{18}$, 35% $H_2O$/0.1% TFA and 65% $CH_3CN$/0.1% TFA, 4 mL/min). HRMS (MALDI-FTMS) calcd for $C_{27}H_{22}N_4O_5+H^+$: 483.1663, found 483.1678.

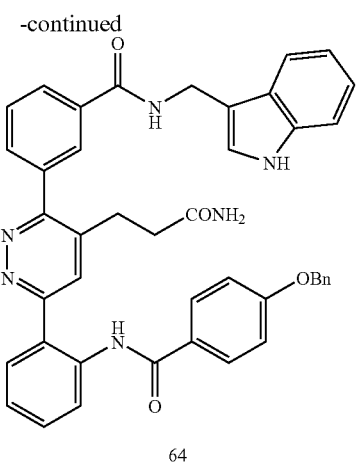

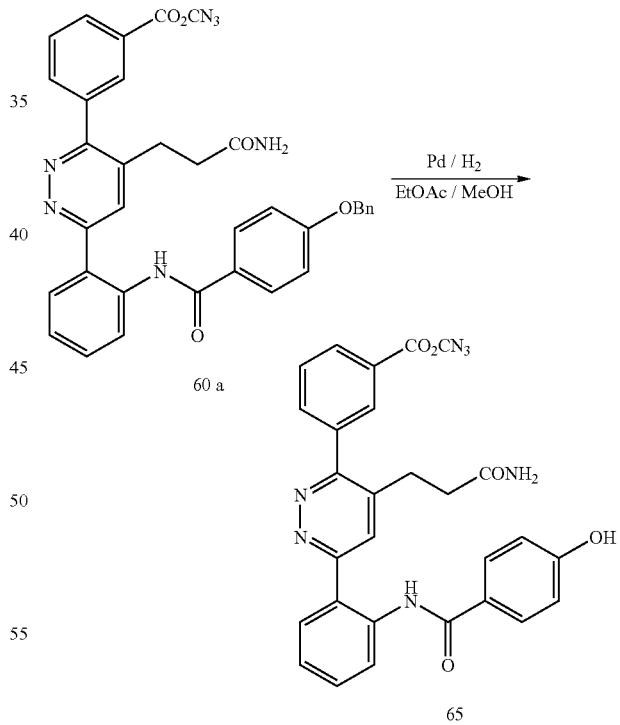

Step 3: Coupling reaction. To a mixture of 62 (17 mg, 0.0297 mmol), 1H-indol-3-ylmethylamine oxalate (7 mg, 0.0296 mmol) and HATU (23 mg, 0.060 mmol) in DMF (0.6 mL) was added DIEA (30 μL, 0.1722 mmol). The reaction was stirred for 12 hr. The mixture was diluted with EtOAc and washed with water. The organic layer was dried over $MgSO_4$ and concentrated. The crude product was purified by column chromatography (3-4% MeOH in $CH_2Cl_2$) to give compound 64 (11.7 mg, 0.0167 mmol, 56% yield) as a pale yellow solid. HRMS (MALDI-FTMS) calcd for $C_{43}H_{36}N_6O_4+H^+$: 701.2871, found 701.2876.

Step 4: Phenol deprotection. To a solution of compound 60a (81 mg, 0.138 mmol) suspended in EtOAc (15 mL) and MeOH (3 mL) was added 10% Pd/C in one portion. The mixture was stirred for 20 hr. at 50° C. under an atmosphere of $H_2$. The catalyst was filtered off through a pad of Celite™, and the filtrate was evaporated under reduced pressure. The crude product was purified by flash column chromatography (The silica gel was pre-washed with 1% $Et_3N$ in $CH_2Cl_2$, 30% to 40% acetone in $CH_2Cl_2$) to afford 65 (41.7 mg, 0.084 mmol, 61% yield) as pale yellow solid. HRMS (MALDI-FTMS) calcd for $C_{28}H_{24}N_4O_5+H^+$: 497.1819, found 497.1815.

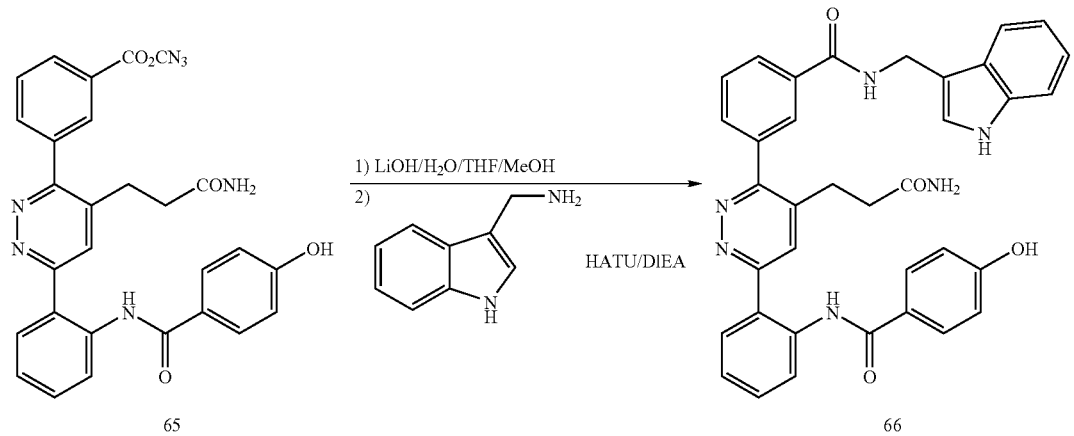

Steps 5 and 6. Final derivatization.

Example a: Ester deprotection and coupling. To a solution of 65 (15 mg, 0.0302 mmol) in THF (1 mL) and MeOH (200 μL) was added a solution of LiOH (1.5 mg, 0.0626 mmol) in H$_2$O (100 μL). The reaction mixture was stirred for 24 hr. at room temperature. It was diluted with EtOAc and acidified with 2% HCl aqueous solution to pH 2~3. Then it was extracted with EtOAc. The organic layer was washed with brine, dried over MgSO$_4$ and concentrated to give the crude acid (10 mg, 0.0207 mmol) as a yellow solid. The acid was dissolved in dry DMF under argon atmosphere. 1H-indol-3-yl-methylamine oxalate (10.3 mg, 0.0414 mmol) and HATU (16 mg, 0.0420 mmol) in DMF (0.6 mL) were added, followed by DIEA (30 μL, 0.1722 mmol). The reaction was stirred for 12 hr. The mixture was diluted with EtOAc and washed with water. The organic layer was dried over MgSO$_4$ and concentrated. The crude product was purified by HPLC (βsil C$_{18}$, 65% H$_2$O/0.1% TFA and 35% CH$_3$CN/0.1% TFA, 6 mL/min) to give compound 66 as a yellow solid. HRMS (MALDI-FTMS) calcd for $C_{36}H_{30}N_6O_4+H^+$: 611.2401, found 611.2390.

Example b.

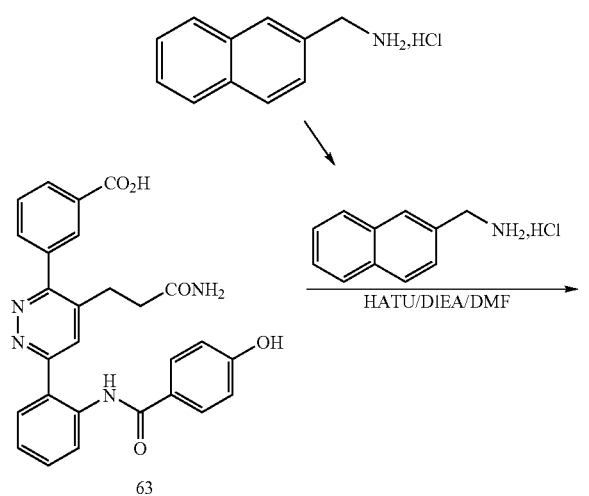

-continued

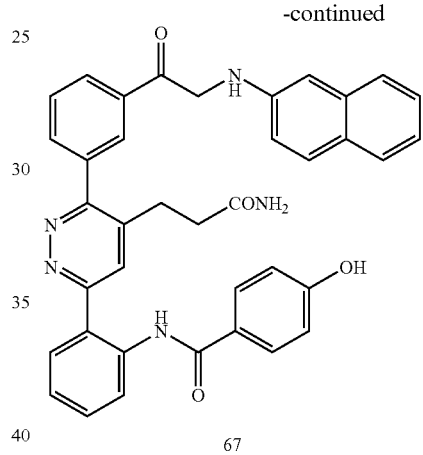

Step a: LiAlH$_4$ (0.4 g, 10 mmol) was added to naphthylnitrile (1.55 g, 10 mmol) in anhydrous THF at 0° C. in portions and mixture was stirred for 1 hr. The reaction was quenched with MeOH and then washed with water. The organic layer was then extracted with 1 N HCl. The aqueous solution was left to stand for 24 hr. at 4° C. to yield crystal of the desired amine.

Step b: Coupling reaction was performed as for 66.

Compound 67: HRMS (MALDI-FTMS) calcd for $C_{38}H_{31}N_5O_4+H^+$: 622.2449, found 622.2453.

Example 17

[6-(2-Benzyl-pyridin-3-yl)-3-(2-isobutyl-pyridin-4-yl)-pyridazin-4-yl]-ethanol

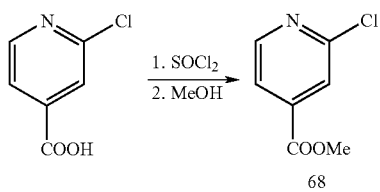

2-Chloro-isonicotinic acid methyl ester (68). 2-Chloro-isonicotinic acid (10 g, 63.5 mmol)) was refluxed in thionylchloride (40 mL) under argon for 6 hr. The SOCl$_2$ was evaporated under reduced pressure, twice toluene (30 mL) was added and evaporated. The residue was dried under high vacuum and set under argon. MeOH (50 mL) was added and the mixture was heated to reflux for 1 hr. and stirred overnight at r.t. The solvent was evaporated. To the residue were added saturated NaHCO$_3$ and ether. The etheral phase was separated, washed with water, brine, dried over MgSO$_4$ and evaporated. The residue was purified by column chromatography using CH$_2$Cl$_2$ as eluent to give 9.1 g (84%) of the white and crystalline product. R$_f$ (CH$_2$Cl$_2$)=0.51. $^1$H NMR (599 MHz, CDCl$_3$) δ 8.52 (d, 1H, J=5.26 Hz, pyridine), 7.87 (d, 1H, J=1.31 Hz, pyridine) 7.75 (dd, 1H, J=5.26, 1.31 Hz, pyridine), 3.95 (s, 3H, methyl ester). $^{13}$C NMR (150 MHz, CDCl$_3$) δ 164.5, 152.7, 150.8, 140.4, 124.3, 121.8, 53.2. HRMS (MALDI-FTMS): MH$^+$ calculated: 172.016; found: 172.0161

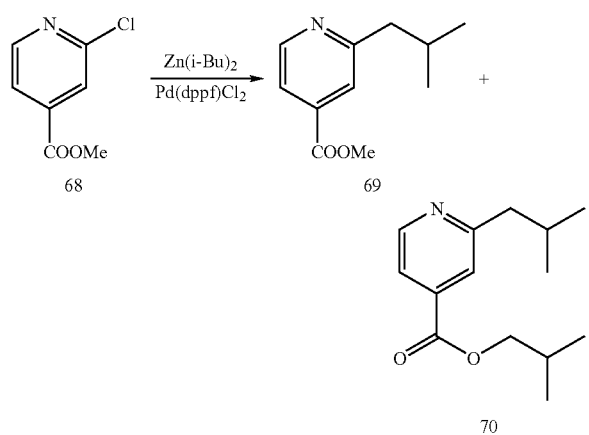

2-Isobutyl-isonicotinic acid methyl ester (69). Step 1: Preparation of Diisobutylzinc. Under Ar isobutylmagnesium chloride in THF (30 mL, 2 M, 60 mmol) was added to a stirred solution of ZnCl$_2$ in THF (61 mL, 0.5 M, 0.0305 mol) over a period of 10 min. The solution was stirred at r.t. for 2 hr. and 1,4-dioxane (22 mL) was added. The resulting white precipitate was filtered off under argon after stirring for 30 min. The obtained clear solution of di-isobutylzinc (n$_{max}$=0.028 mol, if quantitative) was carried on without further purification.

Step 2: Negishi Coupling. Under argon atmosphere 2-chloro-isonicotinic acid methyl ester (2 g, 11.7 mmol) and Pd(dppf)Cl$_2$ (0.8 g, 0.98 mmol) were dissolved in THF (30 mL) and the freshly prepared solution of Zn(i-Bu)$_2$ in THF (110 mL, n$_{max}$=0.028 mol) was added. The mixture was heated to 80° C. for 1.5 h, cooled to r.t., quenched with brine and extracted with EtOAc. The organic extracts were washed with water, brine, dried over MgSO$_4$ and evaporated. The residue wash purified by column chromatography using a gradient of EtOAc 20-50% in cHex and a mixture of two products (in about 1:1 ratio) was obtained in a combined yield of 2.01 g (80%).

Compound 69: R$_f$(cHex:EtOAc=1:1)=0.49. $^1$H NMR (599 MHz, CDCl$_3$) δ 8.65 (d, 1H, pyridine, J=5.0 Hz) 7.64 (d, 1H, pyridine, J=1.5 Hz), 7.63 (dd, 1H, pyridine, J=5.0, 1.5 Hz), 3.92 (s, 3H, methylester) 2.71 (d, 2H, isobutyl, J=6.6 Hz), 2.10 (m, 1H, isobutyl), 0.91 (d, 6H, isobutyl, J=6.6 Hz). $^{13}$C NMR (150 MHz, CDCl$_3$) δ 166.1, 163.0, 150.2, 137.5, 122.7, 120.2, 52.7, 47.7, 29.4, 22.5. HRMS (MALDI-FTMS): MH$^+$ calculated: 194.1175; found: 194.1175.

Compound 70: R$_f$(cHex:EtOAc=1:1)=0.58. $^1$H NMR (599 MHz, CDCl$_3$) δ 8.65 (d, 1H, pyridine, J=5.0 Hz) 7.64 (d, 1H, pyridine, J=1.5 Hz), 7.63 (dd, 1H, pyridine, J=5.0, 1.5 Hz), 4.11 (d, 2H, isobutylester, J=6.6 Hz) 2.71 (d, 2H, isobutyl, J=6.6 Hz), 2.08 (m, 2H, isobutylester, isobutyl), 1.00 (d, 6H, isobutylester, J=6.6 Hz) 0.92 (d, 6H, isobutyl, J=6.6 Hz). $^{13}$C NMR (150 MHz, CDCl$_3$) δ 165.7, 163.0, 150.2, 138.0, 122.8, 120.3, 71.8, 47.7, 29.4, 28.0, 22.6, 19.3. HRMS (MALDI-FTMS): MH$^+$ calculated: 236.1645; found: 236.1637

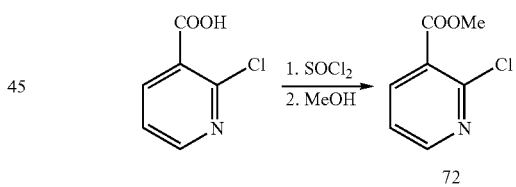

69 R = Me
70 R = iBu

2-Isobutyl-isonicotinic acid (71). The ester mixture (4 g, ~18 mmol) was dissolved in THF (19 mL)/MeOH (19 mL) and NaOH (1.5 g, 36 mmol) in water (19 mL) was added. The resulting solution was stirred at r.t. for 12 hr. The organic solvents were evaporated under reduced pressure and the pH was adjusted to pH=6. The solution was extracted with EtOAc and pH was adjusted to pH=2 and the solution again was extracted with EtOAc. The extracts were washed with acidified (1M HCl) brine, dried over MgSO$_4$ and evaporated to give 2.3 g (70%) of a white crystalline product. R$_f$ (10% MeOH:CHCl$_3$+2 drops AcOH)=0.1. $^1$H NMR (599 MHz, d$_6$ DMSO) δ 8.73 (d, 1H, J=5 Hz, pyridine) 7.79 (s, 1H, pyridine), 7.76 (d, 1H, J=5 Hz, pyridine), 2.76 (d, 2H, J=7 Hz, benzyl), 2.1(m, 1H, alkyl), 0.88 (d, 6H, J=6.5 Hz, alkyl). HRMS (MALDI-FTMS): MH$^+$ calculated: 180.1019; found: 180.1020

2-Chloro-nicotinic acid methyl ester (72). 2-Chloro-nicotinic acid (10 g, 63.5 mmol) was refluxed in thionylchloride (40 mL) under argon for 8 hr. The SOCl$_2$ was evaporated under reduced pressure, twice toluene (30 mL) was added and evaporated. The residue was dried under high vacuum and set under argon. MeOH (50 mL) was added and the mixture was heated to reflux for 1 hr. and stirred overnight at r.t. The solvent was evaporated. To the residue were added saturated NaHCO$_3$ and ether. The etheral phase was separated, washed with water, brine, dried over MgSO$_4$ and evaporated. The residue was purified by column chromatography using CH$_2$Cl$_2$ as eluent to give 7.03 g (64%) of the clear oily product. R$_f$ (CH$_2$Cl$_2$)=0.33. $^1$H NMR (599 MHz, d$_6$ DMSO) δ 8.56 (dd, 1H, pyridine, J=4.82, 1.75 Hz), 8.22 (dd, 1H, pyridine, J=7.6, 1.75 Hz), 7.54 (dd, 1H, pyridine, J=7.6, 4.82 Hz), 3.86 9s, 3H, methyl). $^{13}$C NMR (150 MHz, d$_6$ DMSO) δ

164.5, 152.2, 147.9, 140.3, 126.7, 123.1, 52.8. HRMS (MALDI-FTMS): MH+ calculated: 172.016; found: 172.0161.

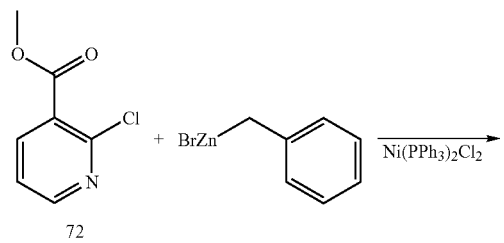

72

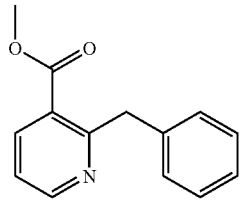

73

2-Benzyl-nicotinic acid methyl ester (73). Under argon atmosphere a solution of the ester 72 (0.396 g, 2.31 mmol) in THF (8 mL) was added to a solution of Ni(PPh$_3$)$_2$Cl$_2$ (0.253 g, 0.387 mmol) in THF (12 mL). The mixture was stirred at r.t. for 10 min. and a solution of benzyl zinc bromide in THF (4.62 mL, 0.5 M, 2.31 mmol) was added over 5 min. The mixture was stirred at r.t. for 3 days. Then it was poured into 10% aqueous NH$_4$Cl (25 mL) and stirred for 1 hr. The product was extracted with EtOAc (25 mL). The organic extract was washed with brine (3×25 mL) and dried over MgSO$_4$. The solvent was removed under reduced pressure. The residue was purified by flash column chromatography using a gradient of EtOAc 10-50% in cHex to give 0.398 g (76%) of the yellowish oily product. R$_f$ (cHex: EtOAc=1:1)=0.48. $^1$H NMR (599 MHz, d$_4$-methanol) δ 8.66 (dd, 1H, pyridine, J=4.82, 1.75 Hz), 8.29 (dd, 1H, pyridine, J=7.89, 1.75 Hz) 7.44 (dd, 1H, pyridine, J=7.89, 4.82 Hz), 7.24 (dd, 2H, phenyl, J=6.79), 7.16 (m, 3H, phenyl) 4.57 (s, 2H, benzylic CH$_2$), 3.86 (s, 3H, methyl ester). $^{13}$C NMR (150 MHz, d$_4$-methanol) δ 168.2, 162.3, 152.7, 140.8, 140.6, 129.9, 129.4, 127.9, 127.4, 123.3, 53.0, 42.9. HRMS (MALDI-FTMS): MH+ calculated: 228.1019; found: 228.1012.

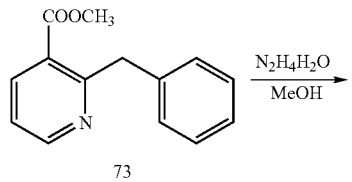

73

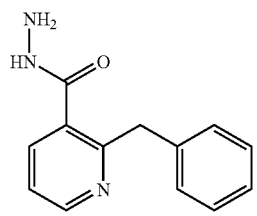

74

2-Benzyl-nicotinic acid hydrazide (74). 2-Benzyl-nicotinic acid methyl ester (1 g, 4.4 mmol), hydrazine (0.55 mL, 35.2 mmol) and MeOH (5 mL) were combined under argon and heated to reflux for 5 hr. As conversion was incomplete, further hydrazine (0.55 mL) was added and the mixture was refluxed for 1 more hour. After cooling to r.t. the solvent was evaporated under reduced pressure, water was added and the mixture was extracted with EtOAc. The organic extracts were washed with brine, dried over MgSO$_4$ and evaporated. The residue was purified by column chromatography using a gradient of 0-10% MeOH in CHCl$_3$ to give 0.41 g (38%) of a white crystalline product. R$_f$(5% MeOH in CHCl$_3$)=0.18. $^1$H NMR (599 MHz, d$_6$-DMSO) δ 9.63 (bs, 1H, NH) 8.52 (dd, 1H, pyridine, J=4.82, 1.75 Hz), 7.67 (dd, 1H, pyridine, J=7.89, 1.75 Hz) 7.27 (dd,1H, pyridine, J=7.89, 4.82 Hz), 7.24 (m, 4H, phenyl, J=6.79), 7.14 (m, 1H, phenyl), 4.51 (bs, 2H, NH$_2$) 4.20 (s, 2H, benzylic CH$_2$). $^{13}$C NMR (150 MHz, d$_6$ DMSO) δ 167.2, 157.9, 149.9, 139.7, 135.5, 130.6, 129.1, 128.0, 125.9, 121.1, 40.7. MS (ESI): MH− calculated: 242; found: 242.

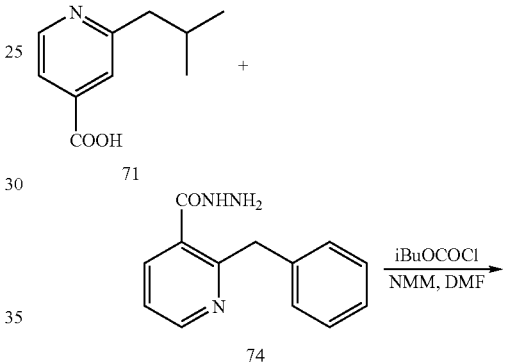

71

74

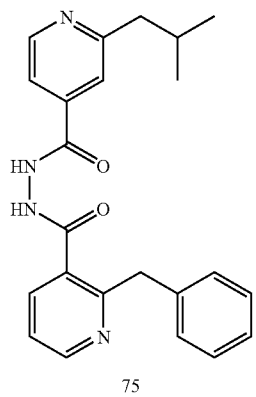

75

2-Isobutyl-isonicotinic acid N'-(2-benzyl-pyridine-3-carbonyl)-hydrazideAcid (75). Compound 71 (0.26 g, 1.45 mmol) was dissolved in DMF (10.5 mL) and the solution was cooled to −15° C. (using a mixture of 25 g CaCl$_2$ in 100 mL water and dry ice). NMM (0.16 mL, 1.45 mmol)) was added followed by isobutyl chloroformate (0.21 mL, 1.6 mmol). After stirring for 7 min. a solution of compound 74 (0.33 g, 1.45 mmol) in DMF (11 mL) was added over a period of 9 min. After stirring for 40 min. at −15° C. the mixture was allowed to warm to r.t. and stirred for 2.5 hr. The solvent was evaporated and the product was purified by silica gel column chromatography using a gradient of 2-5% MeOH:CHCl$_3$. R$_f$ (10% MeOH:CHCl$_3$)=0.45. HRMS (MALDI-FTMS): MH+ calculated: 388.1972; found: 388.1973.

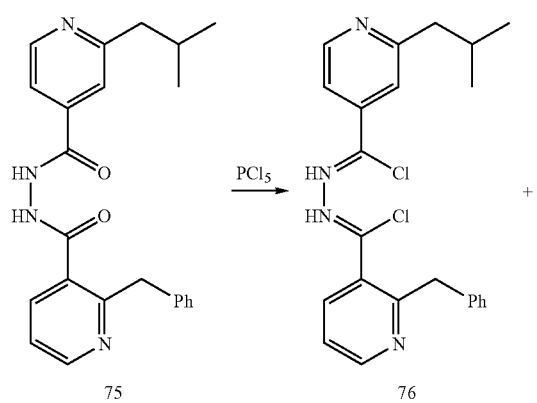

The mixture of 75 (141 mg, 0.363 mmol), phosphorus pentachloride (605 mg, 2.901 mmol) and molecular sieves 4 Å (181 mg) in 2 mL of toluene was heated to reflux for 5 hr. After cooling down, the mixture was poured into ice water and then extracted with ethyl acetate. The organic phase was washed with water to neutral, dried over anhydrous magnesium sulfate and evaporated. The crude product was purified by flash column chromatography (5-10% EtOAc in $CH_2Cl_2$ for 76 and 20-30% EtOAc in $CH_2Cl_2$ for 77) to give a yellow semi-solid dichloride 76 (21 mg, 0.0494 mmol, 14% yield) and yellow solid compound 77 (36 mg, 0.0972 mmol, 27% yield).

Compound 76: HRMS (MALDI-FTMS) calcd for $C_{23}H_{22}Cl_2N_4+H^+$: 425.1294, found 425.1280.

Compound 77: HRMS (MALDI-FTMS) calcd for $C_{23}H_{22}N_4O+H^+$: 371.1866, found 371.1862.

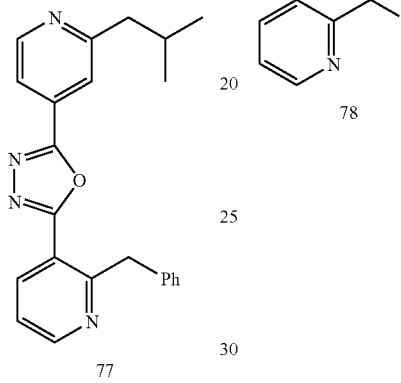

Tetrazine formation (78). Compound 78 was obtained by the procedures described for compound 29.

Compound 78: 90% yield. HRMS (MALDI-FTMS) calcd for $C_{23}H_{22}N_6+H^+$: 383.1979, found 383.1976.

Diels Alder reaction. Compounds 79a and 79b were obtained as described in Example 13.

Compound 79a: $^1$H NMR (599 MHz, $CD_2Cl_2/CD_3OD$, 300° K) δ 8.60 (s, 2H), 7.82 (d, J=7.6 Hz, 1H), 7.51 (br, 2H), 7.41 (s, 1H), 7.39 (dd, J=5.1, 7.4 Hz, 1H), 7.06 (t, J=7.4 Hz, 2H), 7.02 (t, J=7.3 Hz, 1H), 6.85 (d, J=7.5 Hz, 2H), 4.28 (s, 2H), 3.57 (t, J=6.4 Hz, 2H), 2.75 (d, J=7.0 Hz, 2H), 2.71 (t, J=6.4 Hz, 2H), 2.09-2.05 (m, 1H), 0.91 (d, J=6.7 Hz, 6H); $^{13}$C NMR (150 MHz, $CD_2Cl_2/CD_3OD$, 300° K) δ 161.6, 160.0, 159.2, 159.1, 149.8, 147.7, 147.5, 139.6, 139.2, 133.9, 129.6, 129.2 (2C), 128.7 (2C), 126.6, 125.6, 122.9, 122.7, 60.8, 46.6, 41.9, 34.7, 29.9, 22.3 (2C); HRMS (MALDI-FTMS) calcd for $C_{27}H_{28}N_4O+H^+$: 425.2336, found 425.2339.

Compound 79b: $^1$H NMR (599 MHz, $CD_2Cl_2/CD_3OD$, 300° K) δ 8.99 (d, J=5.4 HZ, 1H), 8.88 (br, 1H), 8.72 (s, 1H), 8.67 (d, J=4.3 Hz, 1H), 8.44 (s, 1H), 8.08 (d, J=7.3 Hz, 1H), 7.74 (dd, J=4.7, 7.3 Hz, 1H), 7.24-7.20 (m, 3H), 6.93 (d, J=7.2 Hz, 2H), 4.32 (br, 2H), 3.77 (br, 2H), 3.16 (d, J=7.3 Hz, 2H), 2.49 (br, 2H), 2.40-2.36 (m, 1H), 1.20 (d, J=6.6 Hz, 6H).

Example 18

Biological Assays

Galanin Assay: Compounds of the present invention are tested for binding affinity to GalR1 using the protocol described by Land, T.; et al., *Methods Neurosci*. 1991, 5, 225. Many compounds of the invention will demonstrate binding to GalR1. Compounds of the present invention are tested for ability to displace $^{125}$I Galanin from mice hippocampus membranes (which contain all of the Galanin receptors) also according to the procedure of Land. Many such compounds will demonstrate the ability to displace $^{125}$I Galanin from mice hippocampus membranes.

Bcl-$x_L$-Bak fluorescence polarization assay. The binding affinity of the molecules for Bcl-$x_L$ can be assessed by a fluorescence polarization assay using fluorescein-labeled 16-mer Bak-peptide [A. M. Petros et al. *Protein Science*. 2000, 9, 2528]. Displacement of this probe through competitive binding of the compounds into the hydrophobic cleft of Bcl-$x_L$ would lead to a decrease in its fluorescence polarization which in turn can be related to the known affinity of the 16-mer Bak/Bcl-$x_L$ complex.

Example 19

Formulations

Solution for Parenteral Administration: A solution is prepared from the following ingredients:

| | |
|---|---|
| Active compound | 5 g |
| Sodium chloride for injection | 6 g |
| Sodium hydroxide for pH adjustment at pH | 5-7 |
| Water for inj. | Up to 1000 mL |

The active constituent and the sodium chloride are dissolved in the water. The pH is adjusted with 2M NaOH to pH 3-9 and the solution is filled into sterile ampoules.

Tablets for Oral Administration: 1000 tablets are prepared from the following ingredients:

| | |
|---|---|
| Active compound | 100 g |
| Lactose | 200 g |
| Polyvinyl pyrrolidone | 30 g |
| Microcrystalline cellulose | 30 g |
| Magnesium stearate | 6 g |

The active constituent and lactose are mixed with an aqueous solution of polyvinyl pyrrolidone. The mixture is dried and milled to form granules. The microcrystalline cellulose and then the magnesium stearate are then admixed. The mixture is then compressed in a tablet machine giving 1000 tablets, each containing 100 mg of active constituent.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, any group having 1-3 atoms refers to groups having 1, 2, or 3 atoms. Similarly, a group having 1-5 atoms refers to groups having 1, 2, 3, 4, or 5 atoms, and so forth.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

While preferred embodiments have been illustrated and described, it should be understood that changes and modifications can be made therein in accordance with ordinary skill in the art without departing from the invention in its broader aspects as defined in the following claims.

What is claimed is:

1. A compound having Formula I:

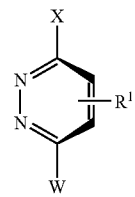

(Formula I)

wherein the pyridazine heterocycle is optionally atropisomeric with respect to X and/or W and wherein:

X is a radical selected from the group consisting of:

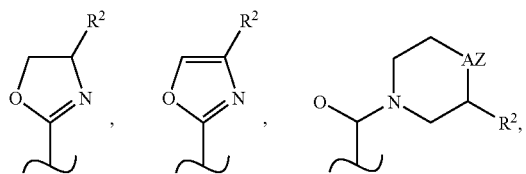

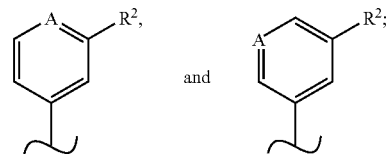

wherein A is either carbon or nitrogen, and Z is either hydrogen or ($C_{1-6}$) alkyl;

W is a radical selected from the group consisting of:

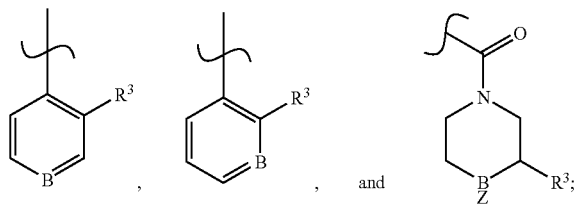

wherein B is either carbon or nitrogen; and

R¹ is selected from the group consisting of side chains of amino acids other than glycine; a substituted or unsubstituted aralkyl or heterocyclylalkyl group; and a $C_{1-10}$ alkyl group, optionally comprising one or more unsaturated bonds within the alkyl chain, and optionally substituted with —OR⁴, —C(O)R⁴, —COOR⁴, —S(O)$_q$R⁴, —NR⁴R⁵, —C(Y)NR⁴R⁵, —N(R⁴)C(Y)OR⁵, —NR⁶C(Y)NR⁴R⁵, —NR⁶C(NR⁷)NR⁴R⁵, —C(NR⁶)NR⁴R⁵, —C(Y)NR⁴OR⁵, —S(O)$_2$NR⁴R⁵, or —NR⁴—SO$_2$—R⁵, wherein Y is O or S;

R² and R³ are independently selected from the group consisting of side chains of amino acids other than glycine; a substituted or unsubstituted aralkyl or heterocyclylalkyl group; a $C_{1-10}$ alkyl group, optionally comprising one or more unsaturated bonds within the alkyl chain, and optionally substituted with —OR⁴, —C(O)R⁴, —COOR⁴, —S(O)$_q$R⁴, —NR⁴R⁵, —C(Y)NR⁴R⁵, —N(R⁴)C(Y)OR⁵, —NR⁶C(Y)NR⁴R⁵, —NR⁶C(NR⁷)NR⁴R⁵, —C(NR⁶)NR⁴R⁵, —C(Y)NR⁴OR⁵, —S(O)$_2$NR⁴R⁵, or —NR⁴—SO$_2$—R⁵, wherein Y is O or S; —C(O)—NH—R⁸; and —NH—C(O)—R⁹;

R⁴, R⁵, R⁶, and R⁷, at each occurrence, are independently hydrogen or a substituted or unsubstituted $C_{1-8}$ alkyl, $C_{2-6}$ alkenyl, ($C_{0-6}$ alkylene)($C_{6-10}$ aryl), or ($C_{0-6}$ alkylene)($C_{3-9}$ heterocyclyl) group; or R⁶ and R⁷, together with the N to which they are attached, form a substituted or unsubstituted heterocyclyl group;

R⁸ and R⁹, at each occurrence, are independently a side chain of an amino acid other than glycine; a substituted or unsubstituted aralkyl or heterocyclylalkyl group; a $C_{1-10}$ alkyl group, optionally comprising one or more unsaturated bonds within the alkyl chain, and optionally substituted with —OR⁴, —C(O)R⁴, —COOR⁴, —S(O)$_q$R⁴, —NR⁴R⁵, —C(Y)NR⁴R⁵, —N(R⁴)C(Y)OR⁵, —NR⁶C(Y)NR⁴R⁵, —NR⁶C(NR⁷)NR⁴R⁵, —C(NR⁶)NR⁴R⁵, —C(Y)NR⁴OR⁵, —S(O)$_2$NR⁴R⁵, or —NR⁴—SO$_2$—R⁵, wherein Y is O or S; and each q is independently 0-2; and stereoisomers thereof, tautomers thereof, and pharmaceutically acceptable salts thereof.

2. The compound according to claim 1, wherein R¹, R², and R³ are independently a substituted or unsubstituted aralkyl or heterocyclylalkyl group; or a $C_{1-10}$ alkyl group, optionally substituted with —OR⁴, —C(O)R⁴, —COOR⁴, —S(O)$_q$R⁴, —NR⁴R⁵,—C(Y)NR⁴R⁵, —N(R⁴)C(Y)OR⁵, —NR⁶C(Y)NR⁴R⁵, —NR⁶C(NR⁷)NR⁴R⁵,—C(NR⁶)NR⁴R⁵, —C(Y)NR⁴OR⁵, —S(O)$_2$NR⁴R⁵, or —NR⁴—SO$_2$—R⁵, and wherein Y is O or S.

3. The compound according to claim 2, wherein R¹, R², and R³ are independently substituted or unsubstituted aralkyl or heterocyclylalkyl group; or a $C_{1-10}$ alkyl group, optionally substituted with —OR⁴ or —C(O)NR⁴R⁵.

4. The compound according to claim 2, wherein R¹, R², and R³ are independently —CH₃, —CH₂CH₃, —(CH₂)₅C(O)OH, —(CH₂)₃NHC(NH)NH₂, —CH₂C(O)NH₂,—CH₂C(O)OH, benzyl, —(CH₂)₃NHC(O)NH₂, —CH₂-cyclohexyl, —CH₂SH, —(CH₂)₂C(O)OH, —(CH₂)₂C(O)NH₂, —CH₂-imidazolyl, —(CH₂)₂OH,CH(OH)CH₃, —CH(CH₃) CH₂CH₃,—CH₂CH(CH₃)CH₃, —(CH₂)₄NH₂, —(CH₂)₂ SCH₃, —(CH₂)₃CH₃, —(CH₂) ₂CH₃, —(CH₂)₃NH₂, —C(SH)(CH₃)CH₃, —CH₂OH, —CH₂-thienyl, —CH₂-indole, —CH₂-phenol, or —CH(CH₃)(CH₃).

5. The compound according to claim 2, wherein R¹, R², and R³ are independently benzyl, methylnaphthyl, methylindolyl, or a $C_{1-10}$ alkyl group,optionally substituted with —OH or —C(O)NH₂.

6. The compound according to claim 1, wherein R² and R³ are independently —C(O)—NH—R⁸ or —NH—C(O)—R⁹.

7. The compound according to claim 6, wherein R¹ is a substituted or unsubstituted aralkyl or heterocyclylalkyl group; or a $C_{1-10}$ alkyl group, optionally substituted with —OR⁴, —C(O)R⁴, —COOR⁴, —S(O)$_q$R⁴, —NR⁴R⁵, —C(Y)NR⁴R⁵,—N(R⁴)C(Y)OR⁵, —NR⁶C(Y)NR⁴R⁵, —NR⁶C(NR⁷)NR⁴R⁵, —C(NR⁶)NR⁴R⁵,—C(Y)NR⁴OR⁵, —S(O)$_2$NR⁴R⁵, or —NR⁴—SO$_2$—R⁵, and wherein Y is O or S.

8. The compound according to claim 1, wherein one of R² and R³ is —C(O)—NH—R⁸, and the other of R² and R³ is —NH—C(O)—R⁹.

9. The compound according to claim 1, wherein R⁸ and R⁹ are independently —CH₃, —CH₂CH₃, —(CH₂)₅C(O)OH, —(CH₂)₃NHC(NH)NH₂, —CH₂C(O)NH₂,—CH₂C(O)OH, benzyl, —(CH₂)₃NHC(O)NH₂, —CH₂-cyclohexyl, —CH₂SH, —(CH₂)₂C(O)OH, —(CH₂)₂C(O)NH₂, —CH₂-imidazolyl, —(CH₂)₂OH, CH(OH)CH₃, —CH(CH₃) CH₂CH₃,—CH₂CH(CH₃)CH₃, —(CH₂)₄NH₂, —(CH₂)₂ SCH₃, —(CH₂)₃CH₃,—(CH₂)₂CH₃, —(CH₂)₃NH₂,—C(SH)(CH₃)CH₃, —CH₂OH, —CH₂-thienyl, —CH₂-indolyl, —CH₂-phenol, or —CH(CH₃)(CH₃).

10. The compound according to claim 1 represented by the following structure:

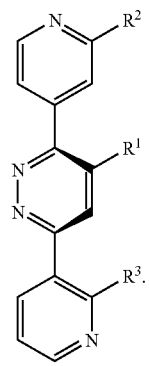

11. The compound according to claim 1 represented by the following structure:

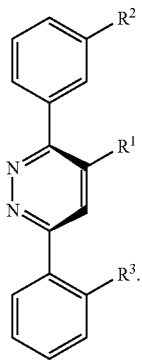

12. The compound according to claim 11 represented by the following structure:

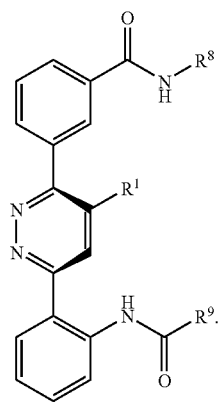

13. The compound according to claim 1 represented by the following structure:

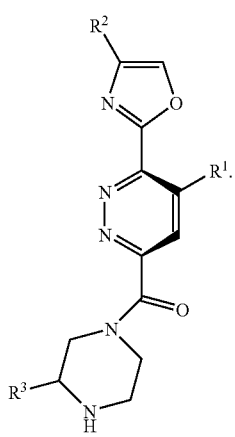

14. A pharmaceutical composition comprising a therapeutically effective amount of a compound of claim 1 and a pharmaceutically acceptable carrier.

15. The compound according to claim 1, wherein $R^2$ and $R^3$ are independently selected from the group consisting of side chains of amino acids other than glycine; a substituted or unsubstituted aralkyl or heterocyclylalkyl group; a $C_{1-10}$ alkyl group, optionally comprising one or more unsaturated bonds within the alkyl chain, and substituted with —$OR^4$, —$C(O)R^4$, —$COOR^4$, —$S(O)_qR^4$, —$NR^4R^5$, —$C(Y)NR^4R^5$, —$N(R^4)C(Y)OR^5$, —$NR^6C(Y)NR^4R^5$, $NR^6C(NR^7)NR^4R^5$, —$C(NR^6)NR^4R^5$, —$C(Y)NR^4OR^5$, —$S(O)_2NR^4R^5$, or —$NR^4$—$SO_2$—$R^5$, wherein Y is O or S; —C(O)—NH—$R^8$; and —NH—C(O)—$R^9$.

* * * * *

UNITED STATES PATENT AND TRADEMARK OFFICE
CERTIFICATE OF CORRECTION

| | | |
|---|---|---|
| PATENT NO. | : 7,579,350 B2 | Page 1 of 1 |
| APPLICATION NO. | : 11/368302 | |
| DATED | : August 25, 2009 | |
| INVENTOR(S) | : Rebek, Jr. et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 641 days.

Signed and Sealed this

Fourteenth Day of September, 2010

David J. Kappos
*Director of the United States Patent and Trademark Office*